US010792229B2

(12) United States Patent
Pratt et al.

(10) Patent No.: US 10,792,229 B2
(45) Date of Patent: Oct. 6, 2020

(54) APERTURED FIBROUS STRUCTURES AND METHODS FOR MAKING SAME

(71) Applicant: The Procter & Gamble Company, Cincinnati, OH (US)

(72) Inventors: Michael Sean Pratt, St. Bernard, OH (US); Min Mao, Deerfield Township, OH (US); David Charles Oertel, Cincinnati, OH (US); Janine Anne Flood, Cincinnati, OH (US); Tom Edward Dufresne, Loveland, OH (US); Paula A. Chmielewski, Cincinnati, OH (US); Andreas Josef Dreher, Cincinnati, OH (US); Alyssandrea Hope Hamad-Ebrahimpour, Cincinnati, OH (US)

(73) Assignee: The Procter & Gamble Company, Cincinnati, OH (US)

(*) Notice: Subject to any disclaimer, the term of this patent is extended or adjusted under 35 U.S.C. 154(b) by 199 days.

(21) Appl. No.: 14/879,154

(22) Filed: Oct. 9, 2015

(65) Prior Publication Data

US 2016/0101026 A1    Apr. 14, 2016

Related U.S. Application Data

(60) Provisional application No. 62/062,186, filed on Oct. 10, 2014.

(51) Int. Cl.
| *A61K 8/02* | (2006.01) |
| *A61L 9/012* | (2006.01) |
| *A61Q 5/00* | (2006.01) |
| *A61Q 11/00* | (2006.01) |
| *A61Q 19/00* | (2006.01) |
| *C11B 9/00* | (2006.01) |
| *C11D 17/04* | (2006.01) |
| *D01F 1/10* | (2006.01) |
| *D04H 1/42* | (2012.01) |

(52) U.S. Cl.
CPC ........... *A61K 8/027* (2013.01); *A61L 9/012* (2013.01); *A61Q 5/00* (2013.01); *A61Q 11/00* (2013.01); *A61Q 19/00* (2013.01); *C11B 9/00* (2013.01); *C11D 17/04* (2013.01); *D01F 1/10* (2013.01); *D04H 1/42* (2013.01)

(58) Field of Classification Search
CPC . A61K 8/027; D01F 1/10; D04H 1/42; D04H 1/70; D04H 1/72; D04H 13/00; Y10T 428/24132; A61L 9/012; A61Q 11/00; A61Q 19/00; A61Q 5/00; C11B 9/00; C11D 17/04
See application file for complete search history.

(56) References Cited

U.S. PATENT DOCUMENTS

| 4,588,630 A | * | 5/1986 | Shimalla | ........... D04H 1/56 15/209.1 |
| 4,637,859 A | * | 1/1987 | Trokhan | .......... D21H 25/005 162/109 |
| 4,741,941 A | * | 5/1988 | Englebert | ............ A47L 13/16 15/209.1 |
| 5,780,418 A | * | 7/1998 | Niinaka | ............... A61K 8/02 206/484 |
| 6,955,850 B1 | * | 10/2005 | Cabell | ................ B32B 5/26 428/221 |
| 2003/0203196 A1 | * | 10/2003 | Trokhan | ................ D01F 9/00 428/364 |
| 2012/0036733 A1 | | 2/2012 | Dehn | |
| 2012/0052036 A1 | * | 3/2012 | Glenn, Jr. | ........... C11D 17/041 424/70.11 |
| 2012/0237576 A1 | | 9/2012 | Gordon et al. | |
| 2013/0171421 A1 | | 4/2013 | Weisman et al. | |
| 2013/0167305 A1 | | 7/2013 | Weisman et al. | |
| 2013/0172226 A1 | * | 7/2013 | Dreher | ............ C11D 17/0039 510/220 |

FOREIGN PATENT DOCUMENTS

| WO | WO-9315701 A1 | * | 8/1993 | ....... A61F 13/15731 |
| WO | WO 03044153 A1 | * | 5/2003 | .......... A61K 8/0208 |

OTHER PUBLICATIONS

PCT International Search Report for PCT/US2015/053911 dated Dec. 18, 2015—4 pages.
PCT International Search Report for PCT/US2015/053956 dated Jan. 20, 2016—5 pages.
U.S. Appl. No. 14/879,131, filed Oct. 9, 2015, Matthew Lawrence Lynch, Brandon Philip Illie, Min Mao, David Charles Oertel, Andres Josef Dreher.

* cited by examiner

*Primary Examiner* — Robert A Wax
*Assistant Examiner* — Olga V. Tcherkasskaya
(74) *Attorney, Agent, or Firm* — C. Brant Cook

(57) ABSTRACT

Apertured fibrous structures and more particularly apertured fibrous structures containing one or more fibrous elements, for example filaments, containing one or more fibrous element-forming materials and one or more active agents that are releasable from the fibrous element when exposed to conditions of intended use, and methods for making same.

26 Claims, 14 Drawing Sheets

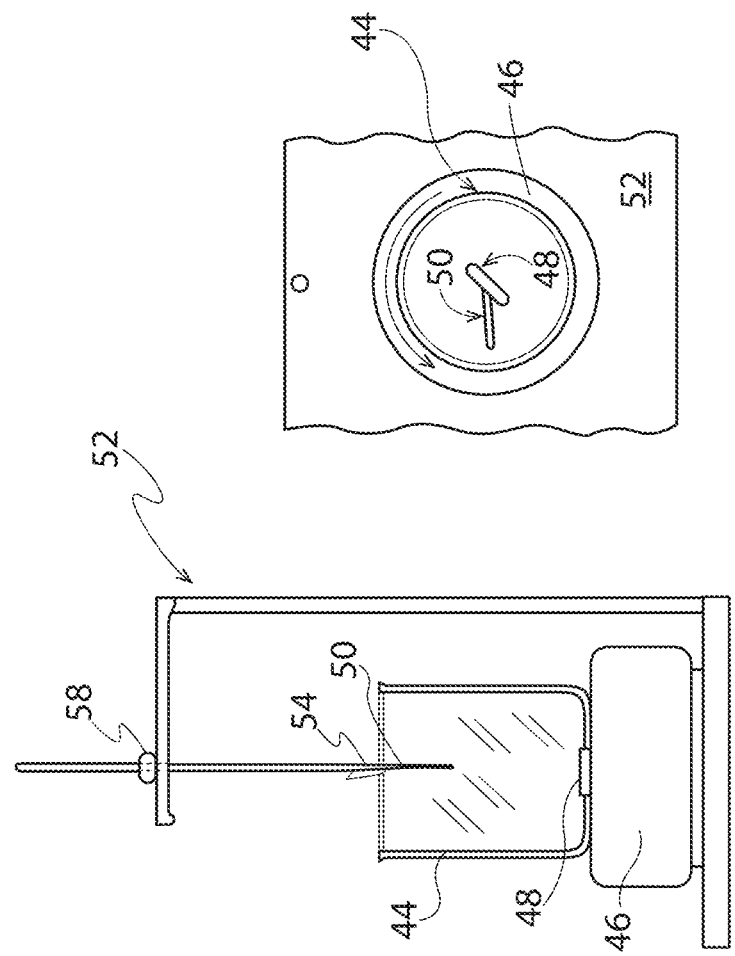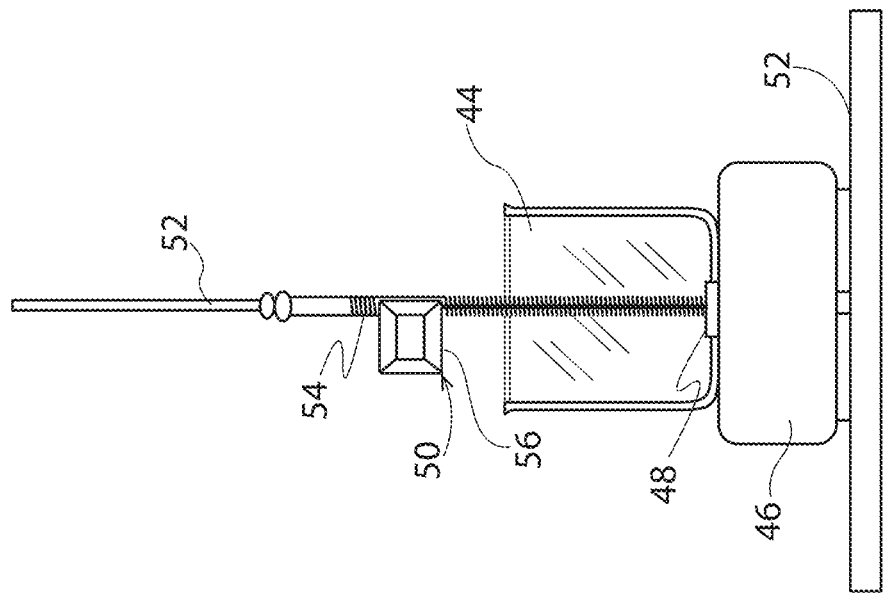

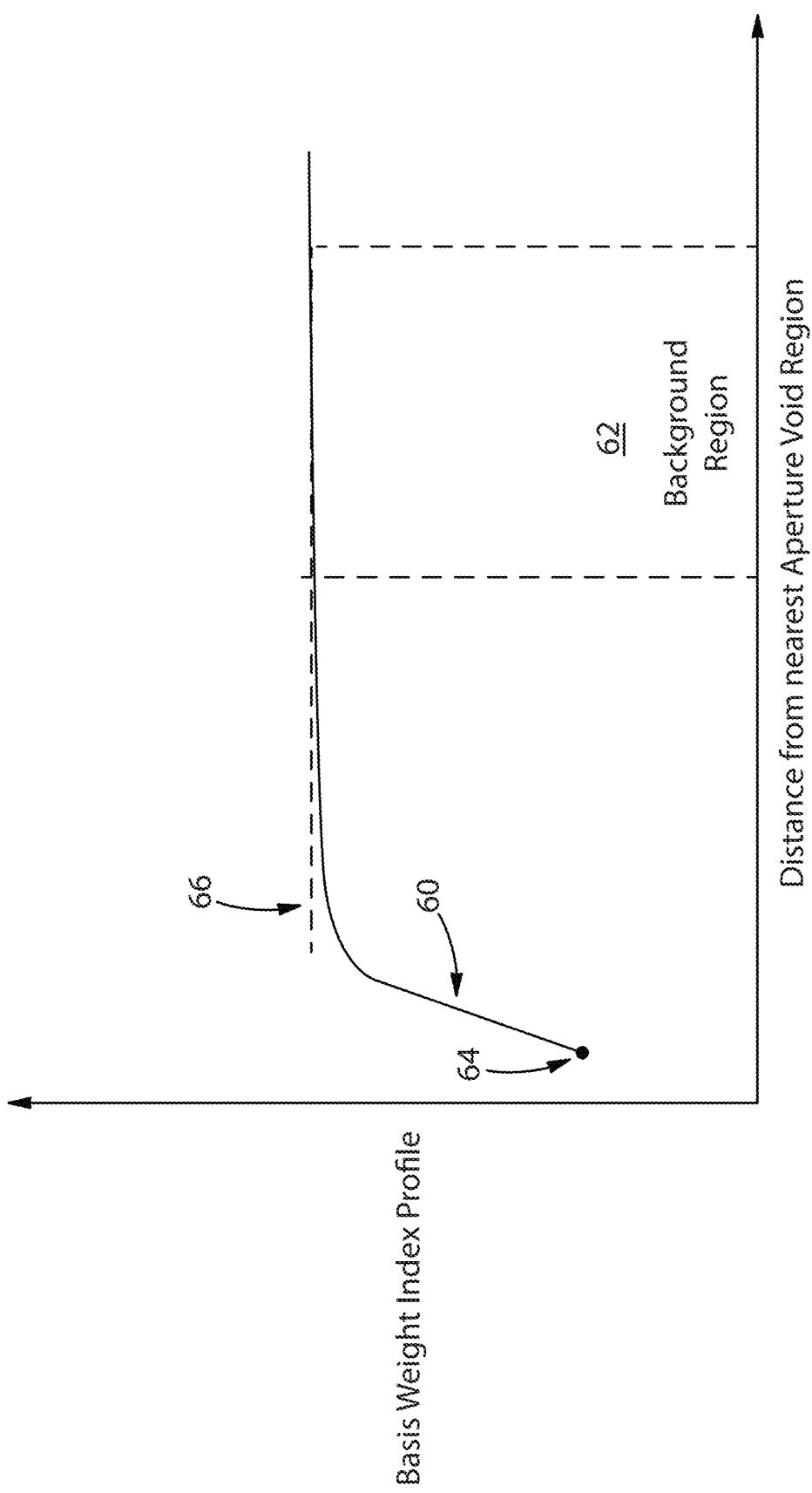

APERTURED FIBROUS STRUCTURES AND METHODS FOR MAKING SAME

FIELD OF THE INVENTION

The present invention relates to apertured fibrous structures and more particularly to apertured fibrous structures comprising one or more fibrous elements, for example filaments, comprising one or more fibrous element-forming materials and one or more active agents that are releasable from the fibrous element when exposed to conditions of intended use, and methods for making same while exhibiting consumer acceptable physical properties, such as strength, softness, elongation, and modulus.

BACKGROUND OF THE INVENTION

Fibrous structures comprising a plurality of filaments comprising one or more filament-forming materials and one or more active agents that are releasable from the fibrous element when exposed to conditions of intended use are known in the art.

One problem with the known fibrous structures is that the known fibrous structures suffered from at least a perception if not an actual dissolution problem where consumers perceived or experienced that such fibrous structures exhibited dissolution properties that were unacceptable to consumers. Many times making a fibrous structure more perceived as easily dissolved makes the fibrous structure too rigid and/or stiff and/or too weak so as not to be consumer acceptable.

Accordingly, there exists a need for a fibrous structure comprising one or more filament-forming materials and one or more active agents that are releasable from the fibrous element when exposed to conditions of intended use that is not perceived by and/or does not exhibit dissolution properties unacceptable to consumers, and methods for making such fibrous structures yet has sufficient strength, flexibility, and softness which consumers expect in a high quality dissolving fibrous structure.

SUMMARY OF THE INVENTION

The present invention fulfills the needs described above by providing novel fibrous structures, for example soluble fibrous structures, comprising a plurality of fibrous elements, for example filaments, one or more fibrous element-forming materials and one or more active agents that are releasable from the fibrous element when exposed to conditions of intended use that comprise one or more apertures and methods for making same.

One solution to the problem described above is a fibrous structure, for example a soluble fibrous structure, comprising a plurality of fibrous elements, for example filaments, comprising one or more fibrous element-forming materials and one or more active agents that are releasable from the fibrous element when exposed to conditions of intended use, wherein the fibrous structure further comprises one or more apertures such that the fibrous structure (apertured fibrous structure), for example soluble fibrous structure, exhibits one or more of the following properties: 1) a Basis Weight Index Ratio (BWIR) of less than 1 as measured according to the Aperture Parameter Test Method described herein; 2) a Basis Weight Index Transition Ratio (BWITR) of greater than 1 as measured according to the Aperture Parameter Test Method described herein; 3) a Fiber Orientation Index Ratio (FOIR) of greater than 1 as measured according to the Aperture Parameter Test Method described herein; 4) an Average Aperture Equivalent Diameter (AAED) of greater than 0.15 mm as measured according to the Aperture Parameter Test Method described herein; 5) an Average Fractional Open Area (AFOA) of from about 0.005% to about 80% as measured according to the Aperture Parameter Test Method described herein; 6) an Average Aperture Area of greater than 0.02 $mm^2$ as measured according to the Aperture Parameter Test Method described herein; 7) a Wall Region Slope of greater than 0.0005 to less than 0.08 as measured according to the Aperture Parameter Test Method described herein; and 8) a Transition Region Slope of greater than 0.0001 to less than 0.1 as measured according to the Aperture Parameter Test Method described herein; and/or 9) an Aperture Optical Circular Diameter of from about 0.1 mm to about 10 mm as measured according to the Optical Aperture Characterization Test Method described herein; 10) an Aperture Optical Circular Area of from about 0.02 $mm^2$ to about 75 $mm^2$ as measured according to the Optical Aperture Characterization Test Method described herein; and 11) an Aperture Optical Circular Percentage of from about 0.005% to about 80% as measured according to the Optical Aperture Characterization Test Method described herein; and methods for making such fibrous structures.

It has unexpectedly been found that fibrous structures, for example soluble fibrous structures, of the present invention comprising one or more fibrous elements, for example filaments, comprising one or more fibrous element-forming materials and one or more active agents that are releasable from the fibrous element when exposed to conditions of intended use that further comprise one or more apertures such that the fibrous structures, for example soluble fibrous structures, are at a minimum perceived by consumers as exhibiting improved dissolution properties and/or actually exhibit improved dissolution properties than known fibrous structures comprising filaments comprising filament-forming materials and active agents. In addition to the improved dissolution properties, the apertures within the fibrous structures of the present invention may provide bonding functions for bonding two or more plies of the fibrous structure together. Furthermore, the present invention offers an opportunity to impart appealing visual and tactile aesthetics, improved softness, lower modulus, more flexible consumer feel, and higher levels of elongation to the fibrous structures. Additionally, the apertures provided within the fibrous structure have been found to provide a means to change the mechanical properties of the fibrous structure. In particular, the modulus of the fibrous structure may be reduced; leading to a more flexible fibrous structure suitable for cooperation with product dispensing apparatuses and further may be experienced by the end user as having improved product handling and softness.

In one example of the present invention, a fibrous structure, for example a soluble fibrous structure, comprising a plurality of fibrous elements, for example filaments, wherein at least one of the fibrous elements comprises one or more fibrous element-forming materials and one or more active agents that are releasable from the fibrous element when exposed to conditions of intended use, the fibrous structure further comprises one or more apertures such that the fibrous structure exhibits a Basis Weight Index Ratio of less than 1 as measured according to the Aperture Parameter Test Method described herein is provided.

In another example of the present invention, a fibrous structure, for example a soluble fibrous structure, comprising a plurality of fibrous elements, for example filaments, wherein at least one of the fibrous elements comprises one or more fibrous element-forming materials and one or more active agents that are releasable from the fibrous element when exposed to conditions of intended use, the fibrous structure further comprises one or more apertures such that the fibrous structure exhibits a Basis Weight Index Transition Ratio of greater than 1 as measured according to the Aperture Parameter Test Method described herein is provided.

In another example of the present invention, a fibrous structure, for example a soluble fibrous structure, comprising a plurality of fibrous elements, for example filaments, wherein at least one of the fibrous elements comprises one or more fibrous element-forming materials and one or more active agents that are releasable from the fibrous element when exposed to conditions of intended use wherein the fibrous structure further comprises one or more apertures such that the fibrous structure exhibits a Fiber Orientation Index Ratio of greater than 1 as measured according to the Aperture Parameter Test Method described herein is provided.

In yet another example of the present invention, a fibrous structure, for example a soluble fibrous structure, comprising a plurality of fibrous elements, for example filaments, wherein at least one of the fibrous elements comprises one or more fibrous element-forming materials and one or more active agents that are releasable from the fibrous element when exposed to conditions of intended use, the fibrous structure further comprises one or more apertures such that the fibrous structure exhibits an Average Aperture Equivalent Diameter of greater than 0.15 mm as measured according to the Aperture Parameter Test Method described herein is provided.

In still another example of the present invention, a fibrous structure, for example a soluble fibrous structure, comprising a plurality of fibrous elements, for example filaments, wherein at least one of the fibrous elements comprises one or more fibrous element-forming materials and one or more active agents that are releasable from the fibrous element when exposed to conditions of intended use, the fibrous structure further comprises one or more apertures such that the fibrous structure exhibits an Average Fractional Open Area of from about 0.005% to about 80% as measured according to the Aperture Parameter Test Method described herein is provided.

In still another example of the present invention, a fibrous structure, for example a soluble fibrous structure, comprising a plurality of fibrous elements, for example filaments, wherein at least one of the fibrous elements comprises one or more fibrous element-forming materials and one or more active agents that are releasable from the fibrous element when exposed to conditions of intended use, the fibrous structure further comprises one or more apertures such that the fibrous structure exhibits an Average Aperture Area of greater than 0.02 mm$^2$ as measured according to the Aperture Parameter Test Method described herein is provided.

In still another example of the present invention, a fibrous structure, for example a soluble fibrous structure, comprising a plurality of fibrous elements, for example filaments, wherein at least one of the fibrous elements comprises one or more fibrous element-forming materials and one or more active agents that are releasable from the fibrous element when exposed to conditions of intended use, the fibrous structure further comprises one or more apertures such that the fibrous structure exhibits a Wall Region Slope of greater than 0.0005 to less than 0.08 as measured according to the Aperture Parameter Test Method described herein is provided.

In still another example of the present invention, a fibrous structure, for example a soluble fibrous structure, comprising a plurality of fibrous elements, for example filaments, wherein at least one of the fibrous elements comprises one or more fibrous element-forming materials and one or more active agents that are releasable from the fibrous element when exposed to conditions of intended use, the fibrous structure further comprises one or more apertures such that the fibrous structure exhibits a Transition Region Slope of greater than 0.0001 to less than 0.1 as measured according to the Aperture Parameter Test Method described herein is provided.

In still another example of the present invention, a fibrous structure, for example a soluble fibrous structure, comprising a plurality of fibrous elements, for example filaments, wherein at least one of the fibrous elements comprises one or more fibrous element-forming materials and one or more active agents that are releasable from the fibrous element when exposed to conditions of intended use, the fibrous structure further comprises one or more apertures such that the fibrous structure exhibits an Aperture Optical Circular Diameter of from about 0.1 mm to about 10 mm as measured according to the Optical Aperture Characterization Test Method described herein is provided.

In still another example of the present invention, a fibrous structure, for example a soluble fibrous structure, comprising a plurality of fibrous elements, for example filaments, wherein at least one of the fibrous elements comprises one or more fibrous element-forming materials and one or more active agents that are releasable from the fibrous element when exposed to conditions of intended use, the fibrous structure further comprises one or more apertures such that the fibrous structure exhibits an Aperture Optical Circular Area of from about 0.02 mm$^2$ to about 75 mm$^2$ as measured according to the Optical Aperture Characterization Test Method described herein is provided.

In still another example of the present invention, a fibrous structure, for example a soluble fibrous structure, comprising a plurality of fibrous elements, for example filaments, wherein at least one of the fibrous elements comprises one or more fibrous element-forming materials and one or more active agents that are releasable from the fibrous element when exposed to conditions of intended use, the fibrous structure further comprises one or more apertures such that the fibrous structure exhibits an Aperture Optical Circular Percentage of from about 0.005% to about 80% as measured according to the Optical Aperture Characterization Test Method described herein is provided.

In one example of the present invention, a fibrous structure, for example a soluble fibrous structure, comprising a plurality of fibrous elements, for example filaments, wherein at least one of the fibrous elements comprises one or more fibrous element-forming materials and one or more active agents that are releasable from the fibrous element when exposed to conditions of intended use, the fibrous structure further comprises one or more apertures such that the fibrous structure exhibits two or more and/or three or more and/or four or more and/or all five of the following properties:

a. a Basis Weight Index Ratio of less than 1 as measured according to the Aperture Parameter Test Method described herein;

b. a Basis Weight Index Transition Ratio of greater than 1 as measured according to the Aperture Parameter Test Method described herein;

c. a Fiber Orientation Index Ratio of greater than 1 as measured according to the Aperture Parameter Test Method described herein;

d. an Average Aperture Equivalent Diameter of greater than 0.15 mm as measured according to the Aperture Parameter Test Method described herein; and e. an Average Fractional Open Area of from about 0.005% to about 80% as measured according to the Aperture Parameter Test Method described herein is provided.

In one example of the present invention, a fibrous structure, for example a soluble fibrous structure, comprising a plurality of fibrous elements, for example filaments, wherein at least one of the fibrous elements comprises one or more fibrous element-forming materials and one or more active agents that are releasable from the fibrous element when exposed to conditions of intended use, the fibrous structure further comprises one or more apertures such that the fibrous structure exhibits two or more and/or all three of the following properties:

a. an Aperture Optical Circular Diameter of from about 0.1 mm to about 10 mm as measured according to the Optical Aperture Characterization Test Method described herein;

b. an Aperture Optical Circular Area of from about 0.02 mm² to about 75 mm² as measured according to the Optical Aperture Characterization Test Method described herein; and c. an Aperture Optical Circular Percentage of from about 0.005% to about 80% as measured according to the Optical Aperture Characterization Test Method described is provided.

In even another example of the present invention, a method for making a fibrous structure comprising the steps of:

a. providing a fibrous structure, for example a soluble fibrous structure, comprising a plurality of fibrous elements, for example filaments, wherein at least one of the fibrous elements comprises one or more fibrous element-forming materials and one or more active agents that are releasable from the fibrous element when exposed to conditions of intended use; and b. imparting one or more apertures to the fibrous structure such that the fibrous structure exhibits a Basis Weight Index Ratio of less than 1 as measured according to the Aperture Parameter Test Method described herein is provided.

In even yet another example of the present invention, a method for making a fibrous structure comprising the steps of:

a. providing a fibrous structure, for example a soluble fibrous structure, comprising a plurality of fibrous elements, for example filaments, wherein at least one of the fibrous elements comprises one or more fibrous element-forming materials and one or more active agents that are releasable from the fibrous element when exposed to conditions of intended use; and b. imparting one or more apertures to the fibrous structure such that the fibrous structure exhibits a Basis Weight Index Transition Ratio of greater than 1 as measured according to the Aperture Parameter Test Method described herein is provided.

In even yet another example of the present invention, a method for making a fibrous structure comprising the steps of:

a. providing a fibrous structure, for example a soluble fibrous structure, comprising a plurality of fibrous elements, for example filaments, wherein at least one of the fibrous elements comprises one or more fibrous element-forming materials and one or more active agents that are releasable from the fibrous element when exposed to conditions of intended use; and b. imparting one or more apertures to the fibrous structure such that the fibrous structure exhibits a Fiber Orientation Index Ratio of greater than 1 as measured according to the Aperture Parameter Test Method described herein is provided.

In even still yet another example of the present invention, a method for making a fibrous structure comprising the steps of:

a. providing a fibrous structure, for example a soluble fibrous structure, comprising a plurality of fibrous elements, for example filaments, wherein at least one of the fibrous elements comprises one or more fibrous element-forming materials and one or more active agents that are releasable from the fibrous element when exposed to conditions of intended use; and b. imparting one or more apertures to the fibrous structure such that the fibrous structure exhibits an Average Aperture Equivalent Diameter of greater than 0.15 mm as measured according to the Aperture Parameter Test Method described herein is provided.

In still another example of the present invention, a method for making a fibrous structure comprising the steps of:

a. providing a fibrous structure, for example a soluble fibrous structure, comprising a plurality of fibrous elements, for example filaments, wherein at least one of the fibrous elements comprises one or more fibrous element-forming materials and one or more active agents that are releasable from the fibrous element when exposed to conditions of intended use; and b. imparting one or more apertures to the fibrous structure such that the fibrous structure exhibits an Average Fractional Open Area of from about 0.005% to about 80% as measured according to the Aperture Parameter Test Method described herein is provided.

In even another example of the present invention, a method for making a fibrous structure comprising the steps of:

a. providing a fibrous structure, for example a soluble fibrous structure, comprising a plurality of fibrous elements, for example filaments, wherein at least one of the fibrous elements comprises one or more fibrous element-forming materials and one or more active agents that are releasable from the fibrous element when exposed to conditions of intended use; and b. imparting one or more apertures to the fibrous structure such that the fibrous structure exhibits an Aperture Optical Circular Diameter of from about 0.1 mm to about 10 mm as measured according to the Optical Aperture Characterization Test Method described herein is provided.

In even another example of the present invention, a method for making a fibrous structure comprising the steps of:

a. providing a fibrous structure, for example a soluble fibrous structure, comprising a plurality of fibrous elements, for example filaments, wherein at least one of the fibrous elements comprises one or more fibrous element-forming materials and one or more active agents that are releasable from the fibrous element when exposed to conditions of intended use; and b. imparting one or more apertures to the fibrous structure such that the fibrous structure exhibits an Aperture Optical Circular Area of from about 0.02 mm² to about 75 mm² as measured according to the Optical Aperture Characterization Test Method described herein is provided.

In even another example of the present invention, a method for making a fibrous structure comprising the steps of:

a. providing a fibrous structure, for example a soluble fibrous structure, comprising a plurality of fibrous elements, for example filaments, wherein at least one of the fibrous elements comprises one or more fibrous element-forming materials and one or more active agents that are releasable from the fibrous element when exposed to conditions of intended use; and b. imparting one or more apertures to the fibrous structure such that the fibrous structure exhibits an Aperture Optical Circular Percentage of from about 0.005% to about 80% as measured according to the Optical Aperture Characterization Test Method described is provided.

In still even another example of the present invention, a method for making a fibrous structure comprising the steps of:

a. providing a fibrous structure, for example a soluble fibrous structure, comprising a plurality of fibrous elements, for example filaments, wherein at least one of the fibrous elements comprises one or more fibrous element-forming materials and one or more active agents that are releasable from the fibrous element when exposed to conditions of intended use; and b. imparting one or more apertures to the fibrous structure such that the fibrous structure exhibits one or more and/or two or more and/or three or more and/or four or more and/or all five of the following properties:

i. a Basis Weight Index Ratio of less than 1 as measured according to the Aperture Parameter Test Method described herein;

ii. a Basis Weight Index Transition Ratio of greater than 1 as measured according to the Aperture Parameter Test Method described herein;

iii. a Fiber Orientation Index Ratio of greater than 1 as measured according to the Aperture Parameter Test Method described herein;

iv. an Average Aperture Equivalent Diameter of greater than 0.15 mm as measured according to the Aperture Parameter Test Method described herein; and v. an Average Fractional Open Area of from about 0.005% to about 80% as measured according to the Aperture Parameter Test Method described herein is provided.

In still even another example of the present invention, a method for making a fibrous structure comprising the steps of:

a. providing a fibrous structure, for example a soluble fibrous structure, comprising a plurality of fibrous elements, for example filaments, wherein at least one of the fibrous elements comprises one or more fibrous element-forming materials and one or more active agents that are releasable from the fibrous element when exposed to conditions of intended use; and b. imparting one or more apertures to the fibrous structure such that the fibrous structure exhibits one or more and/or two or more and/or all three of the following properties:

i. an Aperture Optical Circular Diameter of from about 0.1 mm to about 10 mm as measured according to the Optical Aperture Characterization Test Method described herein;

ii. an Aperture Optical Circular Area of from about 0.02 mm$^2$ to about 75 mm$^2$ as measured according to the Optical Aperture Characterization Test Method described herein; and iii. an Aperture Optical Circular Percentage of from about 0.005% to about 80% as measured according to the Optical Aperture Characterization Test Method described is provided.

As evidenced above, the present invention provides fibrous structures, for example soluble fibrous structures, comprising one or more apertures and a plurality of fibrous elements comprising active agents such that the fibrous structures overcome the negatives associated with known fibrous structures comprising fibrous elements comprising active agents described above.

BRIEF DESCRIPTION OF THE DRAWINGS

FIG. 12 is a front view of an example of a setup of equipment used in measuring dissolution according to the present invention;

FIG. 13 is a side view of FIG. 12;

FIG. 14 is a partial top view of FIG. 12;

FIG. 15 is an example of a Basis Weight Index Profile Plot Lacking a Transition Region. The x-axis is the Distance from Nearest Aperture Void Region Pixel (in μm). The y-axis is the Basis Weight Index Value (in 8-bit Gray Level Intensity);

DETAILED DESCRIPTION OF THE INVENTION

Definitions

Figure 1:
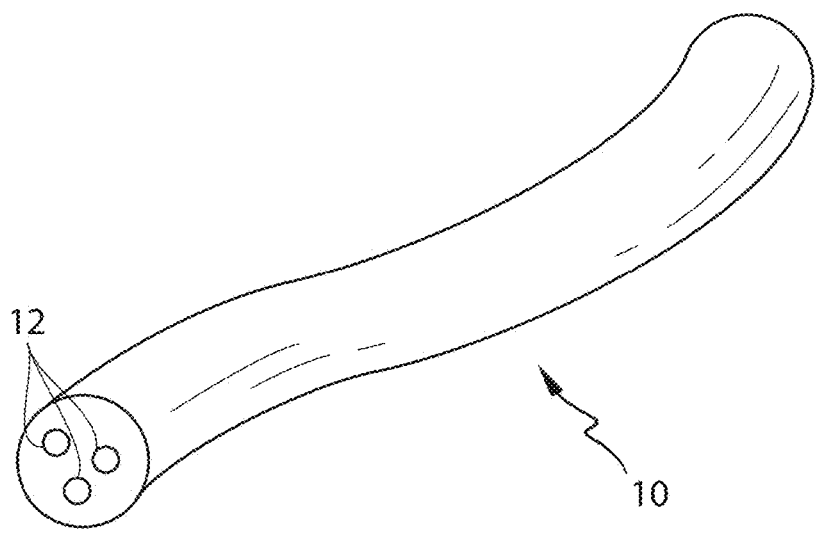
FIG. 1 is a schematic representation of an example of a fibrous element according to the present invention.

"Fibrous structure" as used herein means a structure that comprises one or more fibrous elements. In one example, a fibrous structure according to the present invention means an association of fibrous elements and particles that together form a structure, such as a unitary structure, capable of performing a function.

The fibrous structures of the present invention may be homogeneous or may be layered. If layered, the fibrous structures may comprise at least two and/or at least three and/or at least four and/or at least five layers, for example one or more fibrous element layers, one or more particle layers and/or one or more fibrous element/particle mixture layers. In one example, in a multiple layer fibrous structure, one or more layers may be formed and/or deposited directly upon an existing layer to form a fibrous structure whereas in a multi-ply fibrous structure, one or more existing fibrous structure plies may be combined, for example via thermal bonding, gluing, embossing, rodding, rotary knife aperturing, die cutting, die punching, needlepunching, knurling, pneumatic forming, hydraulic forming, laser cutting, tufting, and/or other mechanical combining process, with one or more other existing fibrous structure plies to form the multi-ply fibrous structure.

In one example, the fibrous structure is a multi-ply fibrous structure that exhibits a basis weight of less than 10,000 g/m$^2$ as measured according to the Basis Weight Test Method described herein.

In one example, the fibrous structure is a sheet of fibrous elements (fibers and/or filaments, such as continuous filaments), of any nature or origin, that have been formed into a web by any means, and may be bonded together by any means, with the exception of weaving or knitting. Felts obtained by wet milling are not soluble fibrous structures. In one example, a fibrous structure according to the present invention means an orderly arrangement of fibrous elements within a structure in order to perform a function. In another example, a fibrous structure of the present invention is an arrangement comprising a plurality of two or more and/or three or more fibrous elements that are inter-entangled or otherwise associated with one another to form a fibrous structure. In yet another example, the fibrous structure of the present invention may comprise, in addition to the fibrous elements of the present invention, one or more solid additives, such as particulates and/or fibers.

In one example, the fibrous structure of the present invention is a "unitary fibrous structure."

"Unitary fibrous structure" as used herein is an arrangement comprising a plurality of two or more and/or three or more fibrous elements that are inter-entangled or otherwise associated with one another to form a fibrous structure. A unitary fibrous structure of the present invention may be one or more plies within a multi-ply fibrous structure. In one example, a unitary fibrous structure of the present invention may comprise three or more different fibrous elements. In another example, a unitary fibrous structure of the present invention may comprise two different fibrous elements, for example a co-formed fibrous structure, upon which a different fibrous elements are deposited to form a fibrous structure comprising three or more different fibrous elements. In one example, a fibrous structure may comprise soluble, for example water-soluble, fibrous elements and insoluble, for example water insoluble fibrous elements.

"Soluble fibrous structure" as used herein means 1) that the entire fibrous structure is soluble or 2) that at least the fibrous elements, for example the filaments of the fibrous structure are soluble. In one example, a soluble fibrous structure according to the present invention is a fibrous structure that comprises greater than 0.5% or greater than 1% or greater than 5% or greater than 10% or greater than 25% or greater than 50% or greater than 75% or greater than 90% or greater than 95% or about 100% by weight of the fibrous structure of soluble materials, for example polar solvent-soluble materials such as water-soluble materials. In one example, a soluble fibrous structure according to the present invention comprises at least 50% or greater than 75% or greater than 90% or greater than 95% or about 100% by weight of the soluble fibrous structure of soluble fibrous elements, for example polar solvent-soluble fibrous elements such as water-soluble fibrous elements.

The soluble fibrous structure comprises a plurality of fibrous elements. In one example, the soluble fibrous structure comprises two or more and/or three or more different fibrous elements.

The soluble fibrous structure and/or fibrous elements thereof, for example filaments, making up the soluble fibrous structure may comprise one or more active agents, for example a fabric care active agent, a dishwashing active agent, a hard surface active agent, a hair care active agent, a floor care active agent, a skin care active agent, an oral care active agent, a medicinal active agent, carpet care active agents, surface care active agents, air care active agents, and mixtures thereof. In one example, a soluble fibrous structure and/or fibrous elements thereof of the present invention comprises one or more surfactants, one or more enzymes (such as in the form of an enzyme prill), one or more perfumes and/or one or more suds suppressors. In another example, a soluble fibrous structure and/or fibrous elements thereof of the present invention comprises a builder and/or a chelating agent. In another example, a soluble fibrous structure and/or fibrous elements thereof of the present invention comprises a bleaching agent (such as an encapsulated bleaching agent). In still another example, a soluble fibrous structure and/or fibrous elements thereof of the present invention comprises one or more surfactants and optionally, one or more perfumes.

In one example, the soluble fibrous structure of the present invention is a water-soluble fibrous structure.

In one example, the soluble fibrous structure of the present invention exhibits a basis weight of less than 10,000 g/m$^2$ and/or less than 5000 g/m$^2$ and/or less than 4000 g/m$^2$ and/or less than 2000 g/m$^2$ and/or less than 1000 g/m$^2$ and/or less than 500 g/m$^2$ as measured according to the Basis Weight Test Method described herein.

"Fibrous element" as used herein means an elongate particulate having a length greatly exceeding its average diameter, i.e. a length to average diameter ratio of at least about 10. A fibrous element may be a filament or a fiber. In one example, the fibrous element is a single fibrous element rather than a yarn comprising a plurality of fibrous elements.

The fibrous elements of the present invention may be spun from a fibrous element-forming compositions also referred to as fibrous element-forming compositions via suitable spinning process operations, such as meltblowing, spunbonding, electro-spinning, and/or rotary spinning.

The fibrous elements of the present invention may be monocomponent and/or multicomponent. For example, the fibrous elements may comprise bicomponent fibers and/or filaments. The bicomponent fibers and/or filaments may be in any form, such as side-by-side, core and sheath, islands-in-the-sea and the like.

In one example, the fibrous element, which may be a filament and/or a fiber and/or a filament that has been cut to smaller fragments (fibers) of the filament may exhibit a length of greater than or equal to 0.254 cm (0.1 in.) and/or greater than or equal to 1.27 cm (0.5 in.) and/or greater than or equal to 2.54 cm (1.0 in.) and/or greater than or equal to 5.08 cm (2 in.) and/or greater than or equal to 7.62 cm (3 in.) and/or greater than or equal to 10.16 cm (4 in.) and/or greater than or equal to 15.24 cm (6 in.). In one example, a fiber of the present invention exhibits a length of less than 5.08 cm (2 in.).

"Filament" as used herein means an elongate particulate as described above. In one example, a filament exhibits a length of greater than or equal to 5.08 cm (2 in.) and/or greater than or equal to 7.62 cm (3 in.) and/or greater than or equal to 10.16 cm (4 in.) and/or greater than or equal to 15.24 cm (6 in.).

Filaments are typically considered continuous or substantially continuous in nature. Filaments are relatively longer than fibers. Filaments are relatively longer than fibers. Non-limiting examples of filaments include meltblown and/or spunbond filaments.

In one example, one or more fibers may be formed from a filament of the present invention, such as when the filaments are cut to shorter lengths. Thus, in one example, the present invention also includes a fiber made from a filament of the present invention, such as a fiber comprising one or more fibrous element-forming materials and one or more additives, such as active agents. Therefore, references to filament and/or filaments of the present invention herein also include fibers made from such filament and/or filaments unless otherwise noted. Fibers are typically considered discontinuous in nature relative to filaments, which are considered continuous in nature.

Non-limiting examples of fibrous elements include meltblown and/or spunbond fibrous elements. Non-limiting examples of polymers that can be spun into fibrous elements include natural polymers, such as starch, starch derivatives, cellulose, such as rayon and/or lyocell, and cellulose derivatives, hemicellulose, hemicellulose derivatives, and synthetic polymers including, but not limited to thermoplastic polymer filaments, such as polyesters, nylons, polyolefins such as polypropylene filaments, polyethylene filaments, and biodegradable thermoplastic fibers such as polylactic acid filaments, polyhydroxyalkanoate filaments, polyesteramide filaments and polycaprolactone filaments. Depending upon the polymer and/or composition from which the fibrous elements are made, the fibrous elements may be soluble or insoluble.

"Fibrous element-forming composition" as used herein means a composition that is suitable for making a fibrous element, for example a filament, of the present invention such as by meltblowing and/or spunbonding. The fibrous element-forming composition comprises one or more fibrous element-forming materials that exhibit properties that make them suitable for spinning into a fibrous element, for example a filament. In one example, the fibrous element-forming material comprises a polymer. In addition to one or more fibrous element-forming materials, the fibrous element-forming composition may comprise one or more additives, for example one or more active agents. In addition, the fibrous element-forming composition may comprise one or more polar solvents, such as water, into which one or more, for example all, of the fibrous element-forming materials and/or one or more, for example all, of the active agents are dissolved and/or dispersed.

In one example as shown in FIG. 1 a fibrous element 10, for example a filament, of the present invention made from a fibrous element-forming composition of the present invention is such that one or more additives, for example one or more active agents 12, may be present in the fibrous element 10, for example filament, rather than on the fibrous element 10, such as a coating. The total level of fibrous element-forming materials and total level of active agents present in the fibrous element-forming composition may be any suitable amount so long as the fibrous elements, for example filaments, of the present invention are produced therefrom.

In one example, one or more additives, such as active agents, may be present in the fibrous element and one or more additional additives, such as active agents, may be present on a surface of the fibrous element. In another example, a fibrous element of the present invention may comprise one or more additives, such as active agents, that are present in the fibrous element when originally made, but then bloom to a surface of the fibrous element prior to and/or when exposed to conditions of intended use of the fibrous element.

Figure 2:
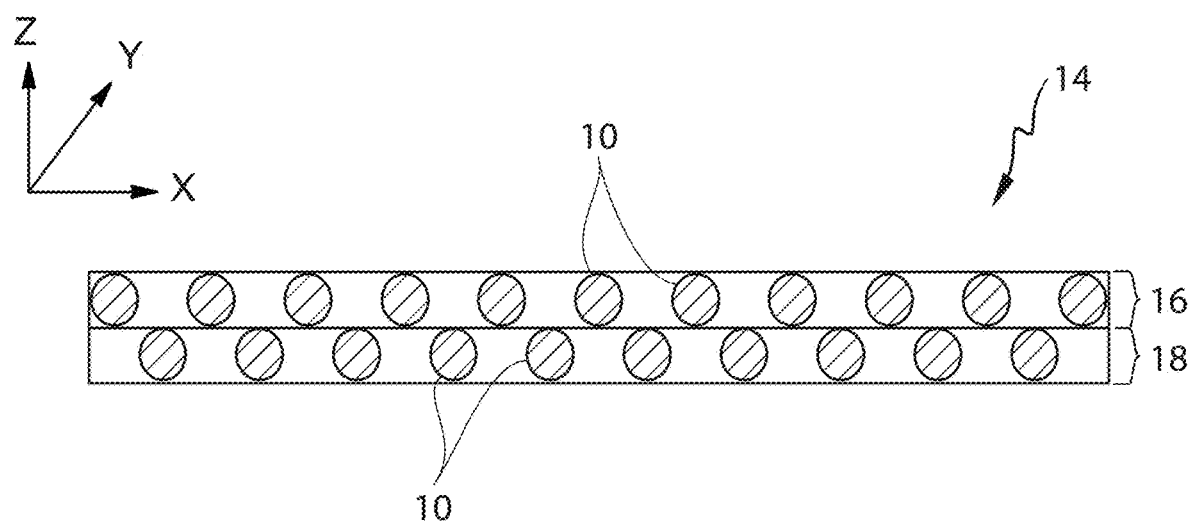
FIG. 2 is a schematic representation of an example of a fibrous structure according to the present invention.

In another example, as shown in FIG. 2, a soluble fibrous structure 14 of the present invention may comprise two or more different layers 16, 18 (in the z-direction of the soluble fibrous structure 14) of fibrous elements 10, for example filaments, of the present invention that form the soluble fibrous structure 14. The fibrous elements 10 in layer 16 may be the same as or different from the fibrous elements 10 of layer 18. Each layer 16, 18 may comprise a plurality of identical or substantially identical or different fibrous elements 10. For example, fibrous elements 10 that may release their active agents at a faster rate than others within the soluble fibrous structure 14 may be positioned to an external surface of the soluble fibrous structure 14.

"Fibrous element-forming material" as used herein means a material, such as a polymer or monomers capable of producing a polymer that exhibits properties suitable for making a fibrous element. In one example, the fibrous element-forming material comprises one or more substituted polymers such as an anionic, cationic, zwitterionic, and/or nonionic polymer. In another example, the polymer may comprise a hydroxyl polymer, such as a polyvinyl alcohol ("PVOH") and/or a polysaccharide, such as starch and/or a starch derivative, such as an ethoxylated starch and/or acid-thinned starch. In another example, the polymer may comprise polyethylenes and/or terephthalates. In yet another example, the fibrous element-forming material is a polar solvent-soluble material.

"Particle" as used herein means a solid additive, such as a powder, granule, encapsulate, microcapsule, and/or prill. In one example, the fibrous elements and/or fibrous structures of the present invention may comprise one or more particles. The particles may be intra-fibrous element (within the fibrous elements, like the active agents) and/or inter-fibrous element (between fibrous elements within a soluble fibrous structure. Non-limiting examples of fibrous elements and/or fibrous structures comprising particles are described in US 2013/0172226 which is incorporated herein by reference. In one example, the particle exhibits a median particle size of 1600 μm or less as measured according to the Median Particle Size Test Method described herein. In another example, the particle exhibits a median particle size of from about 1 μm to about 1600 μm and/or from about 1 μm to about 800 μm and/or from about 5 μm to about 500 μm and/or from about 10 µm to about 300 µm and/or from about 10 µm to about 100 µm and/or from about 10 µm to about 50 µm and/or from about 10 µm to about 30 µm as measured according to the Median Particle Size Test Method described herein. The shape of the particle can be in the form of spheres, rods, plates, tubes, squares, rectangles, discs, stars, fibers or have regular or irregular random forms.

"Active agent-containing particle" as used herein means a solid additive comprising one or more active agents. In one example, the active agent-containing particle is an active agent in the form of a particle (in other words, the particle comprises 100% active agent(s)). The active agent-containing particle may exhibit a median particle size of 1600 µm or less as measured according to the Median Particle Size Test Method described herein. In another example, the active agent-containing particle exhibits a median particle size of from about 1 µm to about 1600 µm and/or from about 1 µm to about 800 µm and/or from about 5 µm to about 500 µm and/or from about 10 µm to about 300 µm and/or from about 10 µm to about 100 µm and/or from about 10 µm to about 50 µm and/or from about 10 µm to about 30 µm as measured according to the Median Particle Size Test Method described herein. In one example, one or more of the active agents is in the form of a particle that exhibits a median particle size of 20 µm or less as measured according to the Median Particle Size Test Method described herein.

In one example of the present invention, the fibrous structure comprises a plurality of particles, for example active agent-containing particles, and a plurality of fibrous elements in a weight ratio of particles, for example active agent-containing particles, to fibrous elements of 1:100 or greater and/or 1:50 or greater and/or 1:10 or greater and/or 1:3 or greater and/or 1:2 or greater and/or 1:1 or greater and/or from about 7:1 to about 1:100 and/or from about 7:1 to about 1:50 and/or from about 7:1 to about 1:10 and/or from about 7:1 to about 1:3 and/or from about 6:1 to 1:2 and/or from about 5:1 to about 1:1 and/or from about 4:1 to about 1:1 and/or from about 3:1 to about 1.5:1.

In another example of the present invention, the fibrous structure comprises a plurality of particles, for example active agent-containing particles, and a plurality of fibrous elements in a weight ratio of particles, for example active agent-containing particles, to fibrous elements of from about 7:1 to about 1:1 and/or from about 7:1 to about 1.5:1 and/or from about 7:1 to about 3:1 and/or from about 6:1 to about 3:1.

In yet another example of the present invention, the fibrous structure comprises a plurality of particles, for example active agent-containing particles, and a plurality of fibrous elements in a weight ratio of particles, for example active agent-containing particles, to fibrous elements of from about 1:1 to about 1:100 and/or from about 1:2 to about 1:50 and/or from about 1:3 to about 1:50 and/or from about 1:3 to about 1:10.

In another example, the fibrous structure of the present invention comprises a plurality of particles, for example active agent-containing particles, at a particle basis weight of greater than 1 $g/m^2$ and/or greater than 10 $g/m^2$ and/or greater than 20 $g/m^2$ and/or greater than 30 $g/m^2$ and/or greater than 40 $g/m^2$ and/or from about 1 $g/m^2$ to about 5000 $g/m^2$ and/or to about 3500 $g/m^2$ and/or to about 2000 $g/m^2$ and/or from about 1 $g/m^2$ to about 1000 $g/m^2$ and/or from about 10 $g/m^2$ to about 400 $g/m^2$ and/or from about 20 $g/m^2$ to about 300 $g/m^2$ and/or from about 30 $g/m^2$ to about 200 $g/m^2$ and/or from about 40 $g/m^2$ to about 100 $g/m^2$ as measured by the Basis Weight Test Method described herein.

In another example, the fibrous structure of the present invention comprises a plurality of fibrous elements at a basis weight of greater than 1 $g/m^2$ and/or greater than 10 $g/m^2$ and/or greater than 20 $g/m^2$ and/or greater than 30 $g/m^2$ and/or greater than 40 $g/m^2$ and/or from about 1 $g/m^2$ to about 10000 $g/m^2$ and/or from about 10 $g/m^2$ to about 5000 $g/m^2$ and/or to about 3000 $g/m^2$ and/or to about 2000 $g/m^2$ and/or from about 20 $g/m^2$ to about 2000 $g/m^2$ and/or from about 30 $g/m^2$ to about 1000 $g/m^2$ and/or from about 30 $g/m^2$ to about 500 $g/m^2$ and/or from about 30 $g/m^2$ to about 300 $g/m^2$ and/or from about 40 $g/m^2$ to about 100 $g/m^2$ and/or from about 40 $g/m^2$ to about 80 $g/m^2$ as measured by the Basis Weight Test Method described herein. In one example, the fibrous structure comprises two or more layers wherein fibrous elements are present in at least one of the layers at a basis weight of from about 1 $g/m^2$ to about 500 $g/m^2$.

"Additive" as used herein means any material present in the fibrous element of the present invention that is not a fibrous element-forming material. In one example, an additive comprises an active agent. In another example, an additive comprises a processing aid. In still another example, an additive comprises a filler. In one example, an additive comprises any material present in the fibrous element that its absence from the fibrous element would result in the fibrous element losing its fibrous element structure, in other words, its absence does not result in the fibrous element losing its solid form. In another example, an additive, for example an active agent, comprises a non-polymer material.

In another example, an additive comprises a plasticizer for the fibrous element. Non-limiting examples of suitable plasticizers for the present invention include polyols, copolyols, polycarboxylic acids, polyesters and dimethicone copolyols. Examples of useful polyols include, but are not limited to, glycerin, diglycerin, propylene glycol, ethylene glycol, butylene glycol, pentylene glycol, cyclohexane dimethanol, hexanediol, 2,2,4-trimethylpentane-1,3-diol, polyethylene glycol (200-600), pentaerythritol, sugar alcohols such as sorbitol, manitol, lactitol and other mono- and polyhydric low molecular weight alcohols (e.g., C2-C8 alcohols); mono di- and oligo-saccharides such as fructose, glucose, sucrose, maltose, lactose, high fructose corn syrup solids, and dextrins, and ascorbic acid.

In one example, the plasticizer includes glycerin and/or propylene glycol and/or glycerol derivatives such as propoxylated glycerol. In still another example, the plasticizer is selected from the group consisting of glycerin, ethylene glycol, polyethylene glycol, propylene glycol, glycidol, urea, sorbitol, xylitol, maltitol, sugars, ethylene bisformamide, amino acids, and mixtures thereof.

In another example, an additive comprises a crosslinking agent suitable for crosslinking one or more of the fibrous element-forming materials present in the fibrous elements of the present invention. In one example, the crosslinking agent comprises a crosslinking agent capable of crosslinking hydroxyl polymers together, for example via the hydroxyl polymers hydroxyl moieties. Non-limiting examples of suitable crosslinking agents include imidazolidinones, polycarboxylic acids and mixtures thereof. In one example, the crosslinking agent comprises a urea glyoxal adduct crosslinking agent, for example a dihydroxyimidazolidinone, such as dihydroxyethylene urea ("DHEU"). A crosslinking agent can be present in the fibrous element-forming composition and/or fibrous element of the present invention to control the fibrous element's solubility and/or dissolution in a solvent, such as a polar solvent.

In another example, an additive comprises a rheology modifier, such as a shear modifier and/or an extensional modifier. Non-limiting examples of rheology modifiers include but not limited to polyacrylamide, polyurethanes and polyacrylates that may be used in the fibrous elements of the present invention. Non-limiting examples of rheology modifiers are commercially available from The Dow Chemical Company (Midland, Mich.).

In yet another example, an additive comprises one or more colors and/or dyes that are incorporated into the fibrous elements of the present invention to provide a visual signal when the fibrous elements are exposed to conditions of intended use and/or when an active agent is released from the fibrous elements and/or when the fibrous element's morphology changes.

In still yet another example, an additive comprises one or more release agents and/or lubricants. Non-limiting examples of suitable release agents and/or lubricants include fatty acids, fatty acid salts, fatty alcohols, fatty esters, sulfonated fatty acid esters, fatty amine acetates, fatty amide, silicones, aminosilicones, fluoropolymers, and mixtures thereof. In one example, the release agents and/or lubricants are applied to the fibrous element, in other words, after the fibrous element is formed. In one example, one or more release agents/lubricants are applied to the fibrous element prior to collecting the fibrous elements on a collection device to form a fibrous structure. In another example, one or more release agents/lubricants are applied to a soluble fibrous structure formed from the fibrous elements of the present invention prior to contacting one or more soluble fibrous structures, such as in a stack of soluble fibrous structures. In yet another example, one or more release agents/lubricants are applied to the fibrous element of the present invention and/or fibrous structure comprising the fibrous element prior to the fibrous element and/or fibrous structure contacting a surface, such as a surface of equipment used in a processing system so as to facilitate removal of the fibrous element and/or soluble fibrous structure and/or to avoid layers of fibrous elements and/or soluble fibrous structures of the present invention sticking to one another, even inadvertently. In one example, the release agents/lubricants comprise particulates.

In even still yet another example, an additive comprises one or more anti-blocking and/or detackifying agents. Non-limiting examples of suitable anti-blocking and/or detackifying agents include starches, starch derivatives, crosslinked polyvinylpyrrolidone, crosslinked cellulose, microcrystalline cellulose, silica, metallic oxides, calcium carbonate, talc, mica, and mixtures thereof.

"Conditions of intended use" as used herein means the temperature, physical, chemical, and/or mechanical conditions that a fibrous element of the present invention is exposed to when the fibrous element is used for one or more of its designed purposes. For example, if a fibrous element and/or a soluble fibrous structure comprising a fibrous element are designed to be used in a washing machine for laundry care purposes, the conditions of intended use will include that temperature, chemical, physical and/or mechanical conditions present in a washing machine, including any wash water, during a laundry washing operation. In another example, if a fibrous element and/or a soluble fibrous structure comprising a fibrous element are designed to be used by a human as a shampoo for hair care purposes, the conditions of intended use will include those temperature, chemical, physical and/or mechanical conditions present during the shampooing of the human's hair. Likewise, if a fibrous element and/or soluble fibrous structure comprising a fibrous element is designed to be used in a dishwashing operation, by hand or by a dishwashing machine, the conditions of intended use will include the temperature, chemical, physical and/or mechanical conditions present in a dishwashing water and/or dishwashing machine, during the dishwashing operation.

"Active agent" as used herein means an additive that produces an intended effect in an environment external to a fibrous element and/or soluble fibrous structure comprising the fibrous element of the present, such as when the fibrous element is exposed to conditions of intended use of the fibrous element and/or soluble fibrous structure comprising the fibrous element. In one example, an active agent comprises an additive that treats a surface, such as a hard surface (i.e., kitchen countertops, bath tubs, toilets, toilet bowls, sinks, floors, walls, teeth, cars, windows, mirrors, dishes) and/or a soft surface (i.e., fabric, hair, skin, carpet, crops, plants,). In another example, an active agent comprises an additive that creates a chemical reaction (i.e., foaming, fizzing, coloring, warming, cooling, lathering, disinfecting and/or clarifying and/or chlorinating, such as in clarifying water and/or disinfecting water and/or chlorinating water). In yet another example, an active agent comprises an additive that treats an environment (i.e., deodorizes, purifies, perfumes air). In one example, the active agent is formed in situ, such as during the formation of the fibrous element containing the active agent, for example the fibrous element may comprise a water-soluble polymer (e.g., starch) and a surfactant (e.g., anionic surfactant), which may create a polymer complex or coacervate that functions as the active agent used to treat fabric surfaces.

"Treats" as used herein with respect to treating a surface means that the active agent provides a benefit to a surface or environment. Treats includes regulating and/or immediately improving a surface's or environment's appearance, cleanliness, smell, purity and/or feel. In one example treating in reference to treating a keratinous tissue (for example skin and/or hair) surface means regulating and/or immediately improving the keratinous tissue's cosmetic appearance and/or feel. For instance, "regulating skin, hair, or nail (keratinous tissue) condition" includes: thickening of skin, hair, or nails (e.g., building the epidermis and/or dermis and/or sub-dermal [e.g., subcutaneous fat or muscle] layers of the skin, and where applicable the keratinous layers of the nail and hair shaft) to reduce skin, hair, or nail atrophy, increasing the convolution of the dermal-epidermal border (also known as the rete ridges), preventing loss of skin or hair elasticity (loss, damage and/or inactivation of functional skin elastin) such as elastosis, sagging, loss of skin or hair recoil from deformation; melanin or non-melanin change in coloration to the skin, hair, or nails such as under eye circles, blotching (e.g., uneven red coloration due to, e.g., rosacea) (hereinafter referred to as "red blotchiness"), sallowness (pale color), discoloration caused by telangiectasia or spider vessels, and graying hair.

In another example, treating means removing stains and/or odors from fabric articles, such as clothes, towels, linens, and/or hard surfaces, such as countertops and/or dishware including pots and pans.

"Fabric care active agent" as used herein means an active agent that when applied to fabric provides a benefit and/or improvement to the fabric. Non-limiting examples of benefits and/or improvements to fabric include cleaning (for example by surfactants), stain removal, stain reduction, wrinkle removal, color restoration, static control, wrinkle resistance, permanent press, wear reduction, wear resistance, pill removal, pill resistance, soil removal, soil resistance (including soil release), shape retention, shrinkage reduction, softness, fragrance, anti-bacterial, anti-viral, odor resistance, and odor removal.

"Dishwashing active agent" as used herein means an active agent that when applied to dishware, glassware, pots, pans, utensils, and/or cooking sheets provides a benefit and/or improvement to the dishware, glassware, plastic items, pots, pans and/or cooking sheets. Non-limiting example of benefits and/or improvements to the dishware, glassware, plastic items, pots, pans, utensils, and/or cooking sheets include food and/or soil removal, cleaning (for example by surfactants) stain removal, stain reduction, grease removal, water spot removal and/or water spot prevention, glass and metal care, sanitization, shining, and polishing.

"Hard surface active agent" as used herein means an active agent when applied to floors, countertops, sinks, windows, mirrors, showers, baths, and/or toilets provides a benefit and/or improvement to the floors, countertops, sinks, windows, mirrors, showers, baths, and/or toilets. Non-limiting example of benefits and/or improvements to the floors, countertops, sinks, windows, mirrors, showers, baths, and/or toilets include food and/or soil removal, cleaning (for example by surfactants), stain removal, stain reduction, grease removal, water spot removal and/or water spot prevention, limescale removal, disinfection, shining, polishing, and freshening.

"Beauty benefit active agent," as used herein, refers to an active agent that can deliver one or more beauty benefits.

"Skin care active agent" as used herein, means an active agent that when applied to the skin provides a benefit or improvement to the skin. It is to be understood that skin care active agents are useful not only for application to skin, but also to hair, scalp, nails and other mammalian keratinous tissue.

"Hair care active agent" as used herein, means an active agent that when applied to mammalian hair provides a benefit and/or improvement to the hair. Non-limiting examples of benefits and/or improvements to hair include softness, static control, hair repair, dandruff removal, dandruff resistance, hair coloring, shape retention, hair retention, and hair growth.

"Weight ratio" as used herein means the dry fibrous element, for example filament, basis and/or dry fibrous element-forming material (g or %) on a dry weight basis in the fibrous element, for example filament, to the weight of additive, such as active agent(s) (g or %) on a dry weight basis in the fibrous element, for example filament.

"Hydroxyl polymer" as used herein includes any hydroxyl-containing polymer that can be incorporated into a fibrous element of the present invention, for example as a fibrous element-forming material. In one example, the hydroxyl polymer of the present invention includes greater than 10% and/or greater than 20% and/or greater than 25% by weight hydroxyl moieties.

"Biodegradable" as used herein means, with respect to a material, such as a fibrous element as a whole and/or a polymer within a fibrous element, such as a fibrous element-forming material, that the fibrous element and/or polymer is capable of undergoing and/or does undergo physical, chemical, thermal and/or biological degradation in a municipal solid waste composting facility such that at least 5% and/or at least 7% and/or at least 10% of the original fibrous element and/or polymer is converted into carbon dioxide after 30 days as measured according to the OECD (1992) Guideline for the Testing of Chemicals 301B; Ready Biodegradability —$CO_2$ Evolution (Modified Sturm Test) Test incorporated herein by reference.

"Non-biodegradable" as used herein means, with respect to a material, such as a fibrous element as a whole and/or a polymer within a fibrous element, such as a fibrous element-forming material, that the fibrous element and/or polymer is not capable of undergoing physical, chemical, thermal and/or biological degradation in a municipal solid waste composting facility such that at least 5% of the original fibrous element and/or polymer is converted into carbon dioxide after 30 days as measured according to the OECD (1992) Guideline for the Testing of Chemicals 301B; Ready Biodegradability —$CO_2$ Evolution (Modified Sturm Test) Test incorporated herein by reference.

"Non-thermoplastic" as used herein means, with respect to a material, such as a fibrous element as a whole and/or a polymer within a fibrous element, such as a fibrous element-forming material, that the fibrous element and/or polymer exhibits no melting point and/or softening point, which allows it to flow under pressure, in the absence of a plasticizer, such as water, glycerin, sorbitol, urea and the like.

"Non-thermoplastic, biodegradable fibrous element" as used herein means a fibrous element that exhibits the properties of being biodegradable and non-thermoplastic as defined above.

"Non-thermoplastic, non-biodegradable fibrous element" as used herein means a fibrous element that exhibits the properties of being non-biodegradable and non-thermoplastic as defined above.

"Thermoplastic" as used herein means, with respect to a material, such as a fibrous element as a whole and/or a polymer within a fibrous element, such as a fibrous element-forming material, that the fibrous element and/or polymer exhibits a melting point and/or softening point at a certain temperature, which allows it to flow under pressure, in the absence of a plasticizer "Thermoplastic, biodegradable fibrous element" as used herein means a fibrous element that exhibits the properties of being biodegradable and thermoplastic as defined above.

"Thermoplastic, non-biodegradable fibrous element" as used herein means a fibrous element that exhibits the properties of being non-biodegradable and thermoplastic as defined above.

"Non-cellulose-containing" as used herein means that less than 5% and/or less than 3% and/or less than 1% and/or less than 0.1% and/or 0% by weight of cellulose polymer, cellulose derivative polymer and/or cellulose copolymer is present in fibrous element. In one example, "non-cellulose-containing" means that less than 5% and/or less than 3% and/or less than 1% and/or less than 0.1% and/or 0% by weight of cellulose polymer is present in fibrous element.

"Polar solvent-soluble material" as used herein means a material that is miscible in a polar solvent. In one example, a polar solvent-soluble material is miscible in alcohol and/or water. In other words, a polar solvent-soluble material is a material that is capable of forming a stable (does not phase separate for greater than 5 minutes after forming the homogeneous solution) homogeneous solution with a polar solvent, such as alcohol and/or water at ambient conditions.

"Alcohol-soluble material" as used herein means a material that is miscible in alcohol. In other words, a material that is capable of forming a stable (does not phase separate for greater than 5 minutes after forming the homogeneous solution) homogeneous solution with an alcohol at ambient conditions.

"Water-soluble material" as used herein means a material that is miscible in water. In other words, a material that is capable of forming a stable (does not separate for greater than 5 minutes after forming the homogeneous solution) homogeneous solution with water at ambient conditions.

"Non-polar solvent-soluble material" as used herein means a material that is miscible in a non-polar solvent. In other words, a non-polar solvent-soluble material is a material that is capable of forming a stable (does not phase separate for greater than 5 minutes after forming the homogeneous solution) homogeneous solution with a non-polar solvent.

"Ambient conditions" as used herein means 73° F.±4° F. (about 23° C.±2.2° C.) and a relative humidity of 50%±10%.

"Weight average molecular weight" as used herein means the weight average molecular weight as determined according to the Weight Average Molecular Weight Test Method described herein.

"Length" as used herein, with respect to a fibrous element, means the length along the longest axis of the fibrous element from one terminus to the other terminus. If a fibrous element has a kink, curl or curves in it, then the length is the length along the entire path of the fibrous element.

"Diameter" as used herein, with respect to a fibrous element, is measured according to the Diameter Test Method described herein. In one example, a fibrous element of the present invention exhibits a diameter of less than 100 μm and/or less than 75 μm and/or less than 50 μm and/or less than 25 μm and/or less than 20 μm and/or less than 15 μm and/or less than 10 μm and/or less than 6 μm and/or greater than 1 μm and/or greater than 3 μm.

"Triggering condition" as used herein in one example means anything, as an act or event, that serves as a stimulus and initiates or precipitates a change in the fibrous element, such as a loss or altering of the fibrous element's physical structure and/or a release of an additive, such as an active agent. In another example, the triggering condition may be present in an environment, such as water, when a fibrous element and/or soluble fibrous structure and/or film of the present invention is added to the water. In other words, nothing changes in the water except for the fact that the fibrous element and/or fibrous structure and/or film of the present invention is added to the water.

"Morphology changes" as used herein with respect to a fibrous element's morphology changing means that the fibrous element experiences a change in its physical structure. Non-limiting examples of morphology changes for a fibrous element of the present invention include dissolution, melting, swelling, shrinking, breaking into pieces, exploding, lengthening, shortening, and combinations thereof. The fibrous elements of the present invention may completely or substantially lose their fibrous element physical structure or they may have their morphology changed or they may retain or substantially retain their fibrous element physical structure as they are exposed to conditions of intended use.

"By weight on a dry fibrous element basis and/or dry fibrous structure basis" means that the weight of the fibrous element and/or fibrous structure measured immediately after the fibrous element and/or fibrous structure has been conditioned in a conditioned room at a temperature of 23° C.±1° C. and a relative humidity of 50%±2% for 2 hours. In one example, "by weight on a dry fibrous element basis and/or dry fibrous structure basis" means that the fibrous element and/or fibrous structure comprises less than 20% and/or less than 15% and/or less than 10% and/or less than 7% and/or less than 5% and/or less than 3% and/or to 0% and/or to greater than 0% based on the weight of the fibrous element and/or fibrous structure of moisture, such as water, for example free water, as measured according to the Water Content Test Method described herein.

"Total level" as used herein, for example with respect to the total level of one or more active agents present in the fibrous element and/or fibrous structure, means the sum of the weights or weight percent of all of the subject materials, for example active agents. In other words, a fibrous element and/or fibrous structure may comprise 25% by weight on a dry fibrous element basis and/or dry fibrous structure basis of an anionic surfactant, 15% by weight on a dry fibrous element basis and/or dry fibrous structure basis of a nonionic surfactant, 10% by weight of a chelant, and 5% of a perfume so that the total level of active agents present in the fibrous element is greater than 50%; namely 55% by weight on a dry fibrous element basis and/or dry fibrous structure basis.

"Detergent product" as used herein means a solid form, for example a rectangular solid, sometimes referred to as a sheet, that comprises one or more active agents, for example a fabric care active agent, a dishwashing active agent, a hard surface active agent, and mixtures thereof. In one example, a detergent product of the present invention comprises one or more surfactants, one or more enzymes, one or more perfumes and/or one or more suds suppressors. In another example, a detergent product of the present invention comprises a builder and/or a chelating agent. In another example, a detergent product of the present invention comprises a bleaching agent.

In one example, the detergent product comprises a web, for example a fibrous structure.

"Web" as used herein means a collection of formed fibrous elements (fibers and/or filaments), such as a fibrous structure, and/or a detergent product formed of fibers and/or filaments, such as continuous filaments, of any nature or origin associated with one another. In one example, the web is a rectangular solid comprising fibers and/or filaments that are formed via a spinning process, not a casting process.

"Particulates" as used herein means granular substances and/or powders. In one example, the filaments and/or fibers can be converted into powders.

"Different from" or "different" as used herein means, with respect to a material, such as a fibrous element as a whole and/or a fibrous element-forming material within a fibrous element and/or an active agent within a fibrous element, that one material, such as a fibrous element and/or a fibrous element-forming material and/or an active agent, is chemically, physically and/or structurally different from another material, such as a fibrous element and/or a fibrous element-forming material and/or an active agent. For example, a fibrous element-forming material in the form of a filament is different from the same fibrous element-forming material in the form of a fiber. Likewise, starch is different from cellulose. However, different molecular weights of the same material, such as different molecular weights of a starch, are not different materials from one another for purposes of the present invention.

"Random mixture of polymers" as used herein means that two or more different fibrous element-forming materials are randomly combined to form a fibrous element. Accordingly, two or more different fibrous element-forming materials that are orderly combined to form a fibrous element, such as a core and sheath bicomponent fibrous element, is not a random mixture of different fibrous element-forming materials for purposes of the present invention.

"Associate," "Associated," "Association," and/or "Associating" as used herein with respect to fibrous elements and/or particle means combining, either in direct contact or in indirect contact, fibrous elements and/or particles such that a fibrous structure is formed. In one example, the associated fibrous elements and/or particles may be bonded together for example by adhesives and/or thermal bonds. In another example, the fibrous elements and/or particles may be associated with one another by being deposited onto the same fibrous structure making belt and/or patterned belt.

"Aperture" as used herein means an opening or void or indentation in a fibrous structure which is distinct from the surrounding fibrous structure. In one example, an aperture may comprise any feature where there is a localized disruption of the fibrous structure. In one example, an aperture may comprise a local indentation or localized disruption of the basis weight, thickness, or caliper of the fibrous structure. In another example, an aperture may be an opening in a fibrous structure wherein the opening passes substantially or completely through both generally planar surfaces of the fibrous structure, through one generally planar surface of the fibrous structure, or even through neither planar surface of the fibrous structure. In another example, an aperture may be an opening in the fibrous structure wherein there is a complete opening, partial opening, or even no apparent opening. In still another example, an aperture may comprise a feature which is an embossment in the fibrous structure. In even another example, an aperture is an internal feature to a fibrous structure and/or multi-ply fibrous structure wherein for example the aperture feature may be present on an internal ply of a multi-ply fibrous structure. In even yet another example, an aperture comprises an opening or void or indentation in a fibrous structure wherein the opening or void or indentation is a non-random and/or designed and/or fabricated opening, void, or indentation rather than a random pore that exists between and/or amongst fibrous elements of a fibrous structure resulting from the collection and inter-entangling of fibrous elements on a collection device.

Non-limiting examples of apertures within fibrous structures of the present invention are shown in FIG. 3A through FIG. 6.

As used herein, the articles "a" and "an" when used herein, for example, "an anionic surfactant" or "a fiber" is understood to mean one or more of the material that is claimed or described.

The fibrous structures of the present invention may comprise two or more of the properties and/or features and/or filaments and/or active agents and/or filament-forming materials.

All percentages and ratios are calculated by weight unless otherwise indicated. All percentages and ratios are calculated based on the total composition unless otherwise indicated.

Unless otherwise noted, all component or composition levels are in reference to the active level of that component or composition, and are exclusive of impurities, for example, residual solvents or by-products, which may be present in commercially available sources.

Fibrous Structure

The fibrous structure, for example soluble fibrous structure, of the present invention comprises a plurality of fibrous elements, for example a plurality of filaments. In one example, the plurality of fibrous elements are inter-entangled to form a soluble fibrous structure.

In one example of the present invention, the fibrous structure is a soluble fibrous structure, for example a water-soluble fibrous structure.

In another example of the present invention, the fibrous structure comprises one or more apertures and thus is an apertured fibrous structure. In one example, the fibrous structure comprises a plurality of apertures. The apertures may be arranged in a pattern, for example a repeating pattern, such as a non-random, repeating pattern, and/or a non-repeating pattern.

Apertures within the apertured fibrous structure of the present invention may be of virtually any shape and size. In one example, the apertures within the apertured fibrous structures are generally round or oblong shaped, in a regular pattern of spaced apart openings. In one example, the fibrous structure comprises two or more apertures that are spaced apart from one another at a distance of from about 0.2 mm to about 100 mm and/or from about 0.5 mm to about 10 mm.

Aperturing of fibrous structures, for example soluble fibrous structures, can be accomplished by any number of techniques. For example, aperturing can be accomplished by various processes involving bonding and stretching, such as those described in U.S. Pat. Nos. 3,949,127 and 5,873,868. In one embodiment, the apertures may be formed by forming a plurality of spaced, melt stabilized regions, and then ring-rolling the web to stretch the web and form apertures in the melt stabilized regions, as described in U.S. Pat. Nos. 5,628,097 and 5,916,661, both of which are hereby incorporated by reference herein. In another embodiment, apertures can be formed in a multilayer, fibrous structure configuration by the method described in U.S. Pat. Nos. 6,830,800 and 6,863,960 which are hereby incorporated herein by reference. Still another process for aperturing webs is described in U.S. Pat. No. 8,241,543 entitled "Method And Apparatus For Making An Apertured Web", which is hereby incorporated herein by reference. Non-limiting examples of processes for imparting apertures to a fibrous structure of the present invention include embossing, rodding, rotary knife aperturing, pinning, die cutting, die punching, needlepunching, knurling, crush cutting, shear cutting, pneumatic forming, hydraulic forming, laser cutting, and tufting. In one example, the fibrous structure of the present invention comprises pinning-imparted apertures. In another example, the fibrous structure of the present invention comprises rodding-imparted apertures. In another example, the fibrous structure of the present invention comprises rotary knife aperturing-imparted apertures. In still another example, the fibrous structure of the present invention may comprise apertures that have been imparted to the fibrous structure by different types of aperturing processes.

In one example, apertures may be imparted to a fibrous structure during forming of the fibrous structure on a collection device, such as a patterned belt, that has features, for example depressions and/or protrusions that impart apertures to the fibrous structure upon the fibrous elements contacting the collection device during formation.

Even though the fibrous element and/or fibrous structure of the present invention are in solid form, the fibrous element-forming composition used to make the fibrous elements of the present invention may be in the form of a liquid.

In one example, the fibrous structure comprises a plurality of identical or substantially identical from a compositional perspective of fibrous elements according to the present invention. In another example, the fibrous structure may comprise two or more different fibrous elements according to the present invention. Non-limiting examples of differences in the fibrous elements may be physical differences such as differences in diameter, length, texture, shape, rigidity, elasticity, and the like; chemical differences such as crosslinking level, solubility, melting point, Tg, active agent, fibrous element-forming material, color, level of active agent, basis weight, level of fibrous element-forming material, presence of any coating on fibrous element, biodegradable or not, hydrophobic or not, contact angle, and the like; differences in whether the fibrous element loses its physical structure when the fibrous element is exposed to conditions of intended use; differences in whether the fibrous element's morphology changes when the fibrous element is exposed to conditions of intended use; and differences in rate at which the fibrous element releases one or more of its active agents when the fibrous element is exposed to conditions of intended use. In one example, two or more fibrous element within the fibrous structure may comprise the same fibrous element-forming material, but have different active agents. This may be the case where the different active agents may be incompatible with one another, for example an anionic surfactant (such as a shampoo active agent) and a cationic surfactant (such as a hair conditioner active agent).

Non-limiting examples of differences in the fibrous elements may be physical differences such as differences in diameter, length, texture, shape, rigidity, elasticity, and the like; chemical differences such as crosslinking level, solubility, melting point, Tg, active agent, fibrous element-forming material, color, level of active agent, level of fibrous element-forming material, presence of any coating on fibrous element, biodegradable or not, hydrophobic or not, contact angle, and the like; differences in whether the fibrous element loses its physical structure when the fibrous element is exposed to conditions of intended use; differences in whether the fibrous element's morphology changes when the fibrous element is exposed to conditions of intended use; and differences in rate at which the fibrous element releases one or more of its active agents when the fibrous element is exposed to conditions of intended use.

In another example, the fibrous structure may exhibit different regions, such as different regions of basis weight, density, and/or caliper. In yet another example, the fibrous structure may comprise texture on one or more of its surfaces. A surface of the fibrous structure may comprise a pattern, such as a non-random, repeating pattern. The fibrous structure may be embossed with an emboss pattern.

In one example, the fibrous structure may comprise discrete regions of fibrous elements that differ from other parts of the fibrous structure.

The fibrous structure and/or fibrous elements of the present invention may be used as is or may be coated with one or more active agents.

In one example, the fibrous structure of the present invention exhibits a thickness of greater than 0.01 mm and/or greater than 0.05 mm and/or greater than 0.1 mm and/or to about 100 mm and/or to about 50 mm and/or to about 20 mm and/or to about 10 mm and/or to about 5 mm and/or to about 2 mm and/or to about 0.5 mm and/or to about 0.3 mm as measured by the Thickness Test Method described herein.

In another example, the fibrous structure of the present invention exhibits a Geometric Mean (GM) Tensile Strength of about 200 g/cm or more, and/or about 500 g/cm or more, and/or about 1000 g/cm or more, and/or about 1500 g/cm or more, and/or about 2000 g/cm or more and/or less than 5000 g/cm and/or less than 4000 g/cm and/or less than 3000 g/cm and/or less than 2500 g/cm as measured according to the Tensile Test Method described herein.

In another example, the fibrous structure of the present invention exhibits a Geometric Mean (GM) Peak Elongation of less than 1000% and/or less than 800% and/or less than 650% and/or less than 550% and/or less than 500% and/or less than 250% and/or less than 100% as measured according to the Tensile Test Method described herein.

In another example, the fibrous structure of the present invention exhibits a Geometric Mean (GM) Tangent Modulus of less than 5000 g/cm and/or less than 3000 g/cm and/or greater than 100 g/cm and/or greater than 500 g/cm and/or greater than 1000 g/cm and/or greater than 1500 g/cm as measured according to the Tensile Test Method described herein.

In another example, the fibrous structure of the present invention exhibits a Geometric Mean (GM) Secant Modulus of less than less than 5000 g/cm and/or less than 3000 g/cm and/or less than 2500 g/cm and/or less than 2000 g/cm and/or less than 1500 g/cm and/or greater than 100 g/cm and/or greater than 300 g/cm and/or greater than 500 g/cm as measured according to the Tensile Test Method described herein.

One or more, and/or a plurality of fibrous elements of the present invention may form a fibrous structure by any suitable process known in the art. The fibrous structure may be used to deliver the active agents from the fibrous elements of the present invention when the fibrous structure is exposed to conditions of intended use of the fibrous structure.

In another example, the fibrous structure may exhibit different regions, such as different regions of basis weight, density and/or caliper. In yet another example, the fibrous structure may comprise texture on one or more of its surfaces. A surface of the fibrous structure may comprise a pattern, such as a non-random, repeating pattern. The fibrous structure may be embossed with an emboss pattern. In another example, the fibrous structure may comprise apertures. The apertures may be arranged in a non-random, repeating pattern.

In one example, the fibrous structure may comprise discrete regions of fibrous elements that differ from other parts of the fibrous structure. Non-limiting examples of different regions within fibrous structures are described in U.S. Published Patent Application Nos. 2013/017421 and 2013/0167305 incorporated herein by reference.

Non-limiting examples of use of the fibrous structure of the present invention include, but are not limited to a laundry dryer substrate, washing machine substrate, washcloth, hard surface cleaning and/or polishing substrate, floor cleaning and/or polishing substrate, as a component in a battery, baby wipe, adult wipe, feminine hygiene wipe, bath tissue wipe, window cleaning substrate, oil containment and/or scavenging substrate, insect repellant substrate, swimming pool chemical substrate, food, breath freshener, deodorant, waste disposal bag, packaging film and/or wrap, wound dressing, medicine delivery, building insulation, crops and/or plant cover and/or bedding, glue substrate, skin care substrate, hair care substrate, air care substrate, water treatment substrate and/or filter, toilet bowl cleaning substrate, candy substrate, pet food, livestock bedding, teeth whitening substrates, carpet cleaning substrates, and other suitable uses of the active agents of the present invention.

In one example, a fibrous structure having such fibrous elements can exhibit an average disintegration time of about 60 seconds (s) or less, and/or about 30 s or less, and/or about 10 s or less, and/or about 5 s or less, and/or about 2.0 s or less, and/or 1.5 s or less as measured according to the Dissolution Test Method described herein.

In one example, a fibrous structure of the present invention can exhibit an average dissolution time of about 600 seconds (s) or less, and/or about 400 s or less, and/or about 300 s or less, and/or about 200 s or less, and/or about 175 s or less and/or about 100 or less and/or about 50 or less and/or greater than 1 as measured according to the Dissolution Test Method described herein.

In one example, a fibrous structure having such fibrous elements can exhibit an average disintegration time per gsm of sample of about 1.0 second/gsm (s/gsm) or less, and/or about 0.5 s/gsm or less, and/or about 0.2 s/gsm or less, and/or about 0.1 s/gsm or less, and/or about 0.05 s/gsm or less, and/or about 0.03 s/gsm or less as measured according to the Dissolution Test Method described herein.

In one example, a fibrous structure having such fibrous elements can exhibit an average dissolution time per gsm of sample of about 10 seconds/gsm (s/gsm) or less, and/or about 5.0 s/gsm or less, and/or about 3.0 s/gsm or less, and/or about 2.0 s/gsm or less, and/or about 1.8 s/gsm or less, and/or about 1.5 s/gsm or less as measured according to the Dissolution Test Method described herein.

In certain embodiments, suitable fibrous structures can have a water content (% moisture) from about 0% to about 20%; in certain embodiments, fibrous structures can have a water content from about 1% to about 15%; and in certain embodiments, fibrous structures can have a water content from about 5% to about 10% as measured according to the Water Content Test Method described herein.

In one example, the fibrous structure exhibits a Basis Weight Index Ratio of less than 1 and/or less than 0.9 and/or less than 0.8 and/or less than 0.7 and/or less than 0.6 and/or greater than 0.1 and/or greater than 0.2 and/or greater than 0.3 and/or from about 0.4 to about 0.7 and/or from about 0.45 to about 0.6 as measured according to the Aperture Parameter Test Method described herein.

In another example, the fibrous structure exhibits a Basis Weight Index Transition Ratio of greater than 1 and/or greater than 1.025 and/or greater than 1.05 and/or less than 3 and/or less than 2 and/or less than 1.8 and/or less than 1.5 and/or from about 1 to about 1.5 and/or from about 1 to about 1.3 and/or from about 1.025 to about 1.1 as measured according to the Aperture Parameter Test Method described herein.

In another example, the fibrous structure exhibits a Fiber Orientation Index Ratio of greater than 1 and/or greater than 1.03 and/or greater than 1.05 and/or greater than 1.075 and/or greater than 1.1 and/or greater than 1.125 and/or less than 3 and/or less than 2 and/or less than 1.8 and/or less than 1.5 and/or less than 1.3 and/or from about 1.03 to about 2 and/or from about 1.05 to about 1.5 and/or from about 1.075 to about 1.3 as measured according to the Aperture Parameter Test Method described herein.

In another example, the fibrous structure exhibits an Average Aperture Equivalent Diameter of greater than 0.15 mm and/or greater than 0.3 mm and/or greater than 0.5 mm and/or greater than 0.75 mm and/or less than 10 mm and/or less than 7 mm and/or less than 5 mm and/or less than 3 mm and/or less than 2 mm and/or from about 0.15 mm to about 10 mm and/or from about 0.3 mm to about 5 mm as measured according to the Aperture Parameter Test Method described herein.

In another example, the fibrous structure exhibits an Average Fractional Open Area of greater than about 0.005% and/or greater than about 0.01% and/or greater than about 0.5% and/or greater than about 1% and/or greater than about 2% and/or greater than about 4% and/or less than about 80% and/or less than about 50% and/or less than about 30% and/or less than about 10% and/or from about 0.005% to about 80% and/or from about 0.01% to about 10% as measured according to the Aperture Parameter Test Method described herein.

In another example, the fibrous structure exhibits a Wall Region Slope of greater than 0.0005 and/or greater than 0.001 and/or greater than 0.003 and/or greater than 0.005 and/or greater than 0.007 and/or less than 0.08 and/or less than 0.07 and/or less than 0.05 and/or less than 0.03 and/or less than 0.01 and/or from about 0.001 to about 0.07 and/or from about 0.005 to about 0.05 and/or from about 0.007 to about 0.03 as measured according to the Aperture Parameter Test Method described herein.

In another example, the fibrous structure exhibits a Transition Region Slope of greater than 0.0001 and/or greater than 0.0003 and/or greater than 0.0005 and/or greater than and/or greater than 0.0007 and/or less than 0.1 and/or less than 0.07 and/or less than 0.05 and/or less than 0.03 and/or less than 0.02 and/or from about 0.0001 to about 0.07 and/or from about 0.0003 to about 0.05 and/or from about 0.0005 to about 0.03 as measured according to the Aperture Parameter Test Method described herein.

In another example, the fibrous structure exhibits an Average Aperture Area of greater than 0.02 $mm^2$ and/or greater than 0.05 $mm^2$ and/or greater than 0.1 $mm^2$ and/or greater than 0.2 $mm^2$ and/or greater than 0.3 $mm^2$ and/or greater than 0.5 $mm^2$ and/or greater than 0.7 $mm^2$ and/or less than 75 $mm^2$ and/or less than 50 $mm^2$ and/or less than 25 $mm^2$ and/or less than 10 $mm^2$ and/or less than 5 $mm^2$ and/or less than 4 $mm^2$ and/or less than 3 $mm^2$ and/or less than 2 $mm^2$ and/or less than 1 $mm^2$ and/or from about 0.02 $mm^2$ to about 75 $mm^2$ and/or from about 0.1 $mm^2$ to about 50 $mm^2$ and/or from about 0.1 $mm^2$ to about 10 $mm^2$ as measured according to the Aperture Parameter Test Method described herein.

In still another example of the present invention, the fibrous structure exhibits an Aperture Optical Circular Diameter of from about 0.1 mm to about 10 mm as measured according to the Optical Aperture Characterization Test Method described herein.

In still another example of the present invention, the fibrous structure exhibits an Aperture Optical Circular Area of from about 0.02 $mm^2$ to about 75 $mm^2$ as measured according to the Optical Aperture Characterization Test Method described herein.

In still another example of the present invention, the fibrous structure exhibits an Aperture Optical Circular Percentage of from about 0.005% to about 80% as measured according to the Optical Aperture Characterization Test Method described herein is provided.

Fibrous Elements

The fibrous element, such as a filament and/or fiber, of the present invention comprises one or more fibrous element-forming materials. In addition to the fibrous element-forming materials, the fibrous element may further comprise one or more active agents present within the fibrous element that are releasable from the fibrous element, for example a filament, such as when the fibrous element and/or fibrous structure comprising the fibrous element is exposed to conditions of intended use. In one example, the total level of the one or more fibrous element-forming materials present in the fibrous element is less than 80% by weight on a dry fibrous element basis and/or dry fibrous structure basis and the total level of the one or more active agents present in the fibrous element is greater than 20% by weight on a dry fibrous element basis and/or dry fibrous structure basis.

In one example, the fibrous element of the present invention comprises about 100% and/or greater than 95% and/or greater than 90% and/or greater than 85% and/or greater than 75% and/or greater than 50% by weight on a dry fibrous element basis and/or dry fibrous structure basis of one or more fibrous element-forming materials. For example, the fibrous element-forming material may comprise polyvinyl alcohol, starch, carboxymethylcellulose, and other suitable polymers, especially hydroxyl polymers.

In another example, the fibrous element of the present invention comprises one or more fibrous element-forming materials and one or more active agents wherein the total level of fibrous element-forming materials present in the fibrous element is from about 5% to less than 80% by weight on a dry fibrous element basis and/or dry fibrous structure basis and the total level of active agents present in the fibrous element is greater than 20% to about 95% by weight on a dry fibrous element basis and/or dry fibrous structure basis.

In one example, the fibrous element of the present invention comprises at least 10% and/or at least 15% and/or at least 20% and/or less than less than 80% and/or less than 75% and/or less than 65% and/or less than 60% and/or less than 55% and/or less than 50% and/or less than 45% and/or less than 40% by weight on a dry fibrous element basis and/or dry fibrous structure basis of the fibrous element-forming materials and greater than 20% and/or at least 35% and/or at least 40% and/or at least 45% and/or at least 50% and/or at least 60% and/or less than 95% and/or less than 90% and/or less than 85% and/or less than 80% and/or less than 75% by weight on a dry fibrous element basis and/or dry fibrous structure basis of active agents.

In one example, the fibrous element of the present invention comprises at least 5% and/or at least 10% and/or at least 15% and/or at least 20% and/or less than 50% and/or less than 45% and/or less than 40% and/or less than 35% and/or less than 30% and/or less than 25% by weight on a dry fibrous element basis and/or dry fibrous structure basis of the fibrous element-forming materials and greater than 50% and/or at least 55% and/or at least 60% and/or at least 65% and/or at least 70% and/or less than 95% and/or less than 90% and/or less than 85% and/or less than 80% and/or less than 75% by weight on a dry fibrous element basis and/or dry fibrous structure basis of active agents. In one example, the fibrous element of the present invention comprises greater than 80% by weight on a dry fibrous element basis and/or dry fibrous structure basis of active agents.

In another example, the one or more fibrous element-forming materials and active agents are present in the fibrous element at a weight ratio of total level of fibrous element-forming materials to active agents of 4.0 or less and/or 3.5 or less and/or 3.0 or less and/or 2.5 or less and/or 2.0 or less and/or 1.85 or less and/or less than 1.7 and/or less than 1.6 and/or less than 1.5 and/or less than 1.3 and/or less than 1.2 and/or less than 1 and/or less than 0.7 and/or less than 0.5 and/or less than 0.4 and/or less than 0.3 and/or greater than 0.1 and/or greater than 0.15 and/or greater than 0.2.

In still another example, the fibrous element of the present invention comprises from about 10% and/or from about 15% to less than 80% by weight on a dry fibrous element basis and/or dry fibrous structure basis of a fibrous element-forming material, such as polyvinyl alcohol polymer, starch polymer, and/or carboxymethylcellulose polymer, and greater than 20% to about 90% and/or to about 85% by weight on a dry fibrous element basis and/or dry fibrous structure basis of an active agent. The fibrous element may further comprise a plasticizer, such as glycerin and/or pH adjusting agents, such as citric acid.

In yet another example, the fibrous element of the present invention comprises from about 10% and/or from about 15% to less than 80% by weight on a dry fibrous element basis and/or dry fibrous structure basis of a fibrous element-forming material, such as polyvinyl alcohol polymer, starch polymer, and/or carboxymethylcellulose polymer, and greater than 20% to about 90% and/or to about 85% by weight on a dry fibrous element basis and/or dry fibrous structure basis of an active agent, wherein the weight ratio of fibrous element-forming material to active agent is 4.0 or less. The fibrous element may further comprise a plasticizer, such as glycerin and/or pH adjusting agents, such as citric acid.

In even another example of the present invention, a fibrous element comprises one or more fibrous element-forming materials and one or more active agents selected from the group consisting of: enzymes, bleaching agents, builder, chelants, sensates, dispersants, and mixtures thereof that are releasable and/or released when the fibrous element and/or fibrous structure comprising the fibrous element is exposed to conditions of intended use. In one example, the fibrous element comprises a total level of fibrous element-forming materials of less than 95% and/or less than 90% and/or less than 80% and/or less than 50% and/or less than 35% and/or to about 5% and/or to about 10% and/or to about 20% by weight on a dry fibrous element basis and/or dry fibrous structure basis and a total level of active agents selected from the group consisting of: enzymes, bleaching agents, builder, chelants, perfumes, antimicrobials, antibacterials, antifungals, and mixtures thereof of greater than 5% and/or greater than 10% and/or greater than 20% and/or greater than 35% and/or greater than 50% and/or greater than 65% and/or to about 95% and/or to about 90% and/or to about 80% by weight on a dry fibrous element basis and/or dry fibrous structure basis. In one example, the active agent comprises one or more enzymes. In another example, the active agent comprises one or more bleaching agents. In yet another example, the active agent comprises one or more builders. In still another example, the active agent comprises one or more chelants. In still another example, the active agent comprises one or more perfumes. In even still another example, the active agent comprise one or more antimicrobials, antibacterials, and/or antifungals.

In yet another example of the present invention, the fibrous elements of the present invention may comprise active agents that may create health and/or safety concerns if they become airborne. For example, the fibrous element may be used to inhibit enzymes within the fibrous element from becoming airborne.

In one example, the fibrous elements of the present invention may be meltblown fibrous elements. In another example, the fibrous elements of the present invention may be spunbond fibrous elements. In another example, the fibrous elements may be hollow fibrous elements prior to and/or after release of one or more of its active agents.

The fibrous elements of the present invention may be hydrophilic or hydrophobic. The fibrous elements may be surface treated and/or internally treated to change the inherent hydrophilic or hydrophobic properties of the fibrous element.

In one example, the fibrous element exhibits a diameter of less than 100 μm and/or less than 75 μm and/or less than 50 μm and/or less than 25 μm and/or less than 10 μm and/or less than 5 μm and/or less than 1 μm as measured according to the Diameter Test Method described herein. In another example, the fibrous element of the present invention exhibits a diameter of greater than 1 μm as measured according to the Diameter Test Method described herein. The diameter of a fibrous element of the present invention may be used to control the rate of release of one or more active agents present in the fibrous element and/or the rate of loss and/or altering of the fibrous element's physical structure.

The fibrous element may comprise two or more different active agents. In one example, the fibrous element comprises two or more different active agents, wherein the two or more different active agents are compatible with one another. In another example, the fibrous element comprises two or more different active agents, wherein the two or more different active agents are incompatible with one another.

In one example, the fibrous element may comprise an active agent and/or additive within the fibrous element and/or an active agent and/or additive on an external surface of the fibrous element, such as an active agent and/or additive coating on the fibrous element. The active agent and/or additive on the external surface of the fibrous element may be the same or different from the active agent and/or additive present in the fibrous element. If different, the active agents and/or additives may be compatible or incompatible with one another.

In one example, one or more active agents may be uniformly distributed or substantially uniformly distributed throughout the fibrous element. In another example, one or more active agents may be distributed as discrete regions within the fibrous element. In still another example, at least one active agent is distributed uniformly or substantially uniformly throughout the fibrous element and at least one other active agent is distributed as one or more discrete regions within the fibrous element. In still yet another example, at least one active agent is distributed as one or more discrete regions within the fibrous element and at least one other active agent is distributed as one or more discrete regions different from the first discrete regions within the fibrous element.

Fibrous Element-forming Material

The fibrous element-forming material is any suitable material, such as a polymer or monomers capable of producing a polymer that exhibits properties suitable for making a fibrous element, such as by a spinning process.

In one example, the fibrous element-forming material may comprise a polar solvent-soluble material, such as an alcohol-soluble material and/or a water-soluble material.

In another example, the fibrous element-forming material may comprise a non-polar solvent-soluble material.

In still another example, the fibrous element forming material may comprise a polar solvent-soluble material and be free (less than 5% and/or less than 3% and/or less than 1% and/or 0% by weight on a dry fibrous element basis and/or dry fibrous structure basis) of non-polar solvent-soluble materials.

In yet another example, the fibrous element-forming material may be a film-forming material. In still yet another example, the fibrous element-forming material may be synthetic or of natural origin and it may be chemically, enzymatically, and/or physically modified.

In even another example of the present invention, the fibrous element-forming material may comprise a polymer selected from the group consisting of: polymers derived from acrylic monomers such as the ethylenically unsaturated carboxylic monomers and ethylenically unsaturated monomers, polyvinyl alcohol, polyacrylates, polymethacrylates, copolymers of acrylic acid and methyl acrylate, polyvinylpyrrolidones, polyalkylene oxides, starch and starch derivatives, pullulan, gelatin, hydroxypropylmethylcelluloses, methycelluloses, and carboxymethycelluloses.

In still another example, the fibrous element-forming material may comprises a polymer selected from the group consisting of: polyvinyl alcohol, polyvinyl alcohol derivatives, starch, starch derivatives, cellulose derivatives, hemicellulose, hemicellulose derivatives, proteins, sodium alginate, hydroxypropyl methylcellulose, chitosan, chitosan derivatives, polyethylene glycol, tetramethylene ether glycol, polyvinyl pyrrolidone, hydroxymethyl cellulose, hydroxyethyl cellulose, and mixtures thereof.

In another example, the fibrous element-forming material comprises a polymer is selected from the group consisting of: pullulan, hydroxypropylmethyl cellulose, hydroxyethyl cellulose, hydroxypropyl cellulose, polyvinyl pyrrolidone, carboxymethyl cellulose, sodium alginate, xanthan gum, tragacanth gum, guar gum, acacia gum, Arabic gum, polyacrylic acid, methylmethacrylate copolymer, carboxyvinyl polymer, dextrin, pectin, chitin, levan, elsinan, collagen, gelatin, zein, gluten, soy protein, casein, polyvinyl alcohol, starch, starch derivatives, hemicellulose, hemicellulose derivatives, proteins, chitosan, chitosan derivatives, polyethylene glycol, tetramethylene ether glycol, hydroxymethyl cellulose, and mixtures thereof.

Polar Solvent-soluble Materials

Non-limiting examples of polar solvent-soluble materials include polar solvent-soluble polymers. The polar solvent-soluble polymers may be synthetic or natural original and may be chemically and/or physically modified. In one example, the polar solvent-soluble polymers exhibit a weight average molecular weight of at least 10,000 g/mol and/or at least 20,000 g/mol and/or at least 40,000 g/mol and/or at least 80,000 g/mol and/or at least 100,000 g/mol and/or at least 1,000,000 g/mol and/or at least 3,000,000 g/mol and/or at least 10,000,000 g/mol and/or at least 20,000,000 g/mol and/or to about 40,000,000 g/mol and/or to about 30,000,000 g/mol.

In one example, the polar solvent-soluble polymers are selected from the group consisting of: alcohol-soluble polymers, water-soluble polymers and mixtures thereof. Non-limiting examples of water-soluble polymers include water-soluble hydroxyl polymers, water-soluble thermoplastic polymers, water-soluble biodegradable polymers, water-soluble non-biodegradable polymers and mixtures thereof. In one example, the water-soluble polymer comprises polyvinyl alcohol. In another example, the water-soluble polymer comprises starch. In yet another example, the water-soluble polymer comprises polyvinyl alcohol and starch.

a. Water-soluble Hydroxyl Polymers—Non-limiting examples of water-soluble hydroxyl polymers in accordance with the present invention include polyols, such as polyvinyl alcohol, polyvinyl alcohol derivatives, polyvinyl alcohol copolymers, starch, starch derivatives, starch copolymers, chitosan, chitosan derivatives, chitosan copolymers, cellulose derivatives such as cellulose ether and ester derivatives, cellulose copolymers, hemicellulose, hemicellulose derivatives, hemicellulose copolymers, gums, arabinans, galactans, proteins and various other polysaccharides and mixtures thereof.

In one example, a water-soluble hydroxyl polymer of the present invention comprises a polysaccharide.

"Polysaccharides" as used herein means natural polysaccharides and polysaccharide derivatives and/or modified polysaccharides. Suitable water-soluble polysaccharides include, but are not limited to, starches, starch derivatives, chitosan, chitosan derivatives, cellulose derivatives, hemicellulose, hemicellulose derivatives, gums, arabinans, galactans and mixtures thereof. The water-soluble polysaccharide may exhibit a weight average molecular weight of from about 10,000 to about 40,000,000 g/mol and/or greater than 100,000 g/mol and/or greater than 1,000,000 g/mol and/or greater than 3,000,000 g/mol and/or greater than 3,000,000 to about 40,000,000 g/mol.

The water-soluble polysaccharides may comprise non-cellulose and/or non-cellulose derivative and/or non-cellulose copolymer water-soluble polysaccharides. Such non-cellulose water-soluble polysaccharides may be selected from the group consisting of: starches, starch derivatives, chitosan, chitosan derivatives, hemicellulose, hemicellulose derivatives, gums, arabinans, galactans and mixtures thereof.

In another example, a water-soluble hydroxyl polymer of the present invention comprises a non-thermoplastic polymer.

The water-soluble hydroxyl polymer may have a weight average molecular weight of from about 10,000 g/mol to about 40,000,000 g/mol and/or greater than 100,000 g/mol and/or greater than 1,000,000 g/mol and/or greater than 3,000,000 g/mol and/or greater than 3,000,000 g/mol to about 40,000,000 g/mol. Higher and lower molecular weight water-soluble hydroxyl polymers may be used in combination with hydroxyl polymers having a certain desired weight average molecular weight.

Well known modifications of water-soluble hydroxyl polymers, such as natural starches, include chemical modifications and/or enzymatic modifications. For example, natural starch can be acid-thinned, hydroxy-ethylated, hydroxy-propylated, and/or oxidized. In addition, the water-soluble hydroxyl polymer may comprise dent corn starch.

Naturally occurring starch is generally a mixture of linear amylose and branched amylopectin polymer of D-glucose units. The amylose is a substantially linear polymer of D-glucose units joined by (1,4)-α-D links. The amylopectin is a highly branched polymer of D-glucose units joined by (1,4)-α-D links and (1,6)-α-D links at the branch points. Naturally occurring starch typically contains relatively high levels of amylopectin, for example, corn starch (64-80% amylopectin), waxy maize (93-100% amylopectin), rice (83-84% amylopectin), potato (about 78% amylopectin), and wheat (73-83% amylopectin). Though all starches are potentially useful herein, the present invention is most commonly practiced with high amylopectin natural starches derived from agricultural sources, which offer the advantages of being abundant in supply, easily replenishable and inexpensive.

As used herein, "starch" includes any naturally occurring unmodified starches, modified starches, synthetic starches and mixtures thereof, as well as mixtures of the amylose or amylopectin fractions; the starch may be modified by physical, chemical, or biological processes, or combinations thereof. The choice of unmodified or modified starch for the present invention may depend on the end product desired. In one embodiment of the present invention, the starch or starch mixture useful in the present invention has an amylopectin content from about 20% to about 100%, more typically from about 40% to about 90%, even more typically from about 60% to about 85% by weight of the starch or mixtures thereof.

Suitable naturally occurring starches can include, but are not limited to, corn starch, potato starch, sweet potato starch, wheat starch, sago palm starch, tapioca starch, rice starch, soybean starch, arrow root starch, amioca starch, bracken starch, lotus starch, waxy maize starch, and high amylose corn starch. Naturally occurring starches particularly, corn starch and wheat starch, are the preferred starch polymers due to their economy and availability.

Polyvinyl alcohols herein can be grafted with other monomers to modify its properties. A wide range of monomers has been successfully grafted to polyvinyl alcohol. Non-limiting examples of such monomers include vinyl acetate, styrene, acrylamide, acrylic acid, 2-hydroxyethyl methacrylate, acrylonitrile, 1,3-butadiene, methyl methacrylate, methacrylic acid, maleic acid, itaconic acid, sodium vinylsulfonate, sodium allylsulfonate, sodium methylallyl sulfonate, sodium phenylallylether sulfonate, sodium phenylmethallylether sulfonate, 2-acrylamido-methyl propane sulfonic acid (AMPs), vinylidene chloride, vinyl chloride, vinyl amine and a variety of acrylate esters.

In one example, the water-soluble hydroxyl polymer is selected from the group consisting of: polyvinyl alcohols, hydroxymethylcelluloses, hydroxyethylcelluloses, hydroxypropylmethylcelluloses and mixtures thereof. A non-limiting example of a suitable polyvinyl alcohol includes those commercially available from Sekisui Specialty Chemicals America, LLC (Dallas, Tex.) under the CELVOL® trade name. A non-limiting example of a suitable hydroxypropylmethylcellulose includes those commercially available from the Dow Chemical Company (Midland, Mich.) under the METHOCEL® trade name including combinations with above mentioned hydroxypropylmethylcelluloses.

b. Water-soluble Thermoplastic Polymers—Non-limiting examples of suitable water-soluble thermoplastic polymers include thermoplastic starch and/or starch derivatives, polylactic acid, polyhydroxyalkanoate, polycaprolactone, polyesteramides and certain polyesters, and mixtures thereof.

The water-soluble thermoplastic polymers of the present invention may be hydrophilic or hydrophobic. The water-soluble thermoplastic polymers may be surface treated and/or internally treated to change the inherent hydrophilic or hydrophobic properties of the thermoplastic polymer.

The water-soluble thermoplastic polymers may comprise biodegradable polymers.

Any suitable weight average molecular weight for the thermoplastic polymers may be used. For example, the weight average molecular weight for a thermoplastic polymer in accordance with the present invention is greater than about 10,000 g/mol and/or greater than about 40,000 g/mol and/or greater than about 50,000 g/mol and/or less than about 500,000 g/mol and/or less than about 400,000 g/mol and/or less than about 200,000 g/mol.

Non-polar Solvent-soluble Materials

Non-limiting examples of non-polar solvent-soluble materials include non-polar solvent-soluble polymers. Non-limiting examples of suitable non-polar solvent-soluble materials include cellulose, chitin, chitin derivatives, polyolefins, polyesters, copolymers thereof, and mixtures thereof. Non-limiting examples of polyolefins include polypropylene, polyethylene and mixtures thereof. A non-limiting example of a polyester includes polyethylene terephthalate.

The non-polar solvent-soluble materials may comprise a non-biodegradable polymer such as polypropylene, polyethylene and certain polyesters.

Any suitable weight average molecular weight for the thermoplastic polymers may be used. For example, the weight average molecular weight for a thermoplastic polymer in accordance with the present invention is greater than about 10,000 g/mol and/or greater than about 40,000 g/mol and/or greater than about 50,000 g/mol and/or less than about 500,000 g/mol and/or less than about 400,000 g/mol and/or less than about 200,000 g/mol.

Active Agents

Active agents are a class of additives that are designed and intended to provide a benefit to something other than the fibrous element and/or particle and/or fibrous structure itself, such as providing a benefit to an environment external to the fibrous element and/or particle and/or fibrous structure. Active agents may be any suitable additive that produces an intended effect under intended use conditions of the fibrous element. For example, the active agent may be selected from the group consisting of: personal cleansing and/or conditioning agents such as hair care agents such as shampoo agents and/or hair colorant agents, hair conditioning agents, skin care agents, sunscreen agents, and skin conditioning agents; laundry care and/or conditioning agents such as fabric care agents, fabric conditioning agents, fabric softening agents, fabric anti-wrinkling agents, fabric care anti-static agents, fabric care stain removal agents, soil release agents, dispersing agents, suds suppressing agents, suds boosting agents, anti-foam agents, and fabric refreshing agents; liquid and/or powder dishwashing agents (for hand dishwashing and/or automatic dishwashing machine applications), hard surface care agents, and/or conditioning agents and/or polishing agents; other cleaning and/or conditioning agents such as antimicrobial agents, antibacterial agents, antifungal agents, fabric hueing agents, perfume, bleaching agents (such as oxygen bleaching agents, hydrogen peroxide, percarbonate bleaching agents, perborate bleaching agents, chlorine bleaching agents), bleach activating agents, chelating agents, builders, lotions, brightening agents, air care agents, carpet care agents, dye transfer-inhibiting agents, clay soil removing agents, anti-redeposition agents, polymeric soil release agents, polymeric dispersing agents, alkoxylated polyamine polymers, alkoxylated polycarboxylate polymers, amphilic graft copolymers, dissolution aids, buffering systems, water-softening agents, water-hardening agents, pH adjusting agents, enzymes, flocculating agents, effervescent agents, preservatives, cosmetic agents, make-up removal agents, lathering agents, deposition aid agents, coacervate-forming agents, clays, thickening agents, latexes, silicas, drying agents, odor control agents, antiperspirant agents, cooling agents, warming agents, absorbent gel agents, anti-inflammatory agents, dyes, pigments, acids, and bases; liquid treatment active agents; agricultural active agents; industrial active agents; ingestible active agents such as medicinal agents, teeth whitening agents, tooth care agents, mouthwash agents, periodontal gum care agents, edible agents, dietary agents, vitamins, minerals; water-treatment agents such as water clarifying and/or water disinfecting agents, and mixtures thereof.

Non-limiting examples of suitable cosmetic agents, skin care agents, skin conditioning agents, hair care agents, and hair conditioning agents are described in CTFA Cosmetic Ingredient Handbook, Second Edition, The Cosmetic, Toiletries, and Fragrance Association, Inc. 1988, 1992.

One or more classes of chemicals may be useful for one or more of the active agents listed above. For example, surfactants may be used for any number of the active agents described above. Likewise, bleaching agents may be used for fabric care, hard surface cleaning, dishwashing and even teeth whitening. Therefore, one of ordinary skill in the art will appreciate that the active agents will be selected based upon the desired intended use of the fibrous element and/or particle and/or fibrous structure made therefrom.

For example, if the fibrous element and/or particle and/or fibrous structure made therefrom is to be used for hair care and/or conditioning then one or more suitable surfactants, such as a lathering surfactant could be selected to provide the desired benefit to a consumer when exposed to conditions of intended use of the fibrous element and/or particle and/or fibrous structure incorporating the fibrous element and/or particle.

In one example, if the fibrous element and/or particle and/or fibrous structure made therefrom is designed or intended to be used for laundering clothes in a laundry operation, then one or more suitable surfactants and/or enzymes and/or builders and/or perfumes and/or suds suppressors and/or bleaching agents could be selected to provide the desired benefit to a consumer when exposed to conditions of intended use of the fibrous element and/or particle and/or fibrous structure incorporating the fibrous element and/or particle. In another example, if the fibrous element and/or particle and/or fibrous structure made therefrom is designed to be used for laundering clothes in a laundry operation and/or cleaning dishes in a dishwashing operation, then the fibrous element and/or particle and/or fibrous structure may comprise a laundry detergent composition or dishwashing detergent composition or active agents used in such compositions. In still another example, if the fibrous element and/or particle and/or fibrous structure made therefrom is designed to be used for cleaning and/or sanitizing a toilet bowl, then the fibrous element and/or particle and/or fibrous structure made therefrom may comprise a toilet bowl cleaning composition and/or effervescent composition and/or active agents used in such compositions.

In one example, the active agent is selected from the group consisting of: surfactants, bleaching agents, enzymes, suds suppressors, suds boosting agents, fabric softening agents, denture cleaning agents, hair cleaning agents, hair care agents, personal health care agents, such as diphenhydramine, hueing agents, and mixtures thereof.

Release of Active Agent

One or more active agents may be released from the fibrous element and/or particle and/or fibrous structure when the fibrous element and/or particle and/or fibrous structure is exposed to a triggering condition. In one example, one or more active agents may be released from the fibrous element and/or particle and/or fibrous structure or a part thereof when the fibrous element and/or particle and/or fibrous structure or the part thereof loses its identity, in other words, loses its physical structure. For example, a fibrous element and/or particle and/or fibrous structure loses its physical structure when the fibrous element-forming material dissolves, melts or undergoes some other transformative step such that its structure is lost. In one example, the one or more active agents are released from the fibrous element and/or particle and/or fibrous structure when the fibrous element's and/or particle's and/or fibrous structure's morphology changes.

In another example, one or more active agents may be released from the fibrous element and/or particle and/or fibrous structure or a part thereof when the fibrous element and/or particle and/or fibrous structure or the part thereof alters its identity, in other words, alters its physical structure rather than loses its physical structure. For example, a fibrous element and/or particle and/or fibrous structure alters its physical structure when the fibrous element-forming material swells, shrinks, lengthens, and/or shortens, but retains its fibrous element-forming properties.

In another example, one or more active agents may be released from the fibrous element and/or particle and/or fibrous structure with its morphology not changing (not losing or altering its physical structure).

In one example, the fibrous element and/or particle and/or fibrous structure may release an active agent upon the fibrous element and/or particle and/or fibrous structure being exposed to a triggering condition that results in the release of the active agent, such as by causing the fibrous element and/or particle and/or fibrous structure to lose or alter its identity as discussed above.

Non-limiting examples of triggering conditions include exposing the fibrous element and/or particle and/or fibrous structure to solvent, a polar solvent, such as alcohol and/or water, and/or a non-polar solvent, which may be sequential, depending upon whether the fibrous element-forming material comprises a polar solvent-soluble material and/or a non-polar solvent-soluble material; exposing the fibrous element and/or particle and/or fibrous structure to heat, such as to a temperature of greater than 75° F. and/or greater than 100° F. and/or greater than 150° F. and/or greater than 200° F. and/or greater than 212° F.; exposing the fibrous element and/or particle and/or fibrous structure to cold, such as to a temperature of less than 40° F. and/or less than 32° F. and/or less than 0° F.; exposing the fibrous element and/or particle and/or fibrous structure to a force, such as a stretching force applied by a consumer using the fibrous element and/or particle and/or fibrous structure; and/or exposing the fibrous element and/or particle and/or fibrous structure to a chemical reaction; exposing the fibrous element and/or particle and/or fibrous structure to a condition that results in a phase change; exposing the fibrous element and/or particle and/or fibrous structure to a pH change and/or a pressure change and/or temperature change; exposing the fibrous element and/or particle and/or fibrous structure to one or more chemicals that result in the fibrous element and/or particle and/or fibrous structure releasing one or more of its active agents; exposing the fibrous element and/or particle and/or fibrous structure to ultrasonics; exposing the fibrous element and/or particle and/or fibrous structure to light and/or certain wavelengths; exposing the fibrous element and/or particle and/or fibrous structure to a different ionic strength; and/or exposing the fibrous element and/or particle and/or fibrous structure to an active agent released from another fibrous element and/or particle and/or fibrous structure.

In one example, one or more active agents may be released from the fibrous elements and/or particles of the present invention when a fibrous structure comprising the fibrous elements and/or particles is subjected to a triggering step selected from the group consisting of: pre-treating stains on a fabric article with the fibrous structure; forming a wash liquor by contacting the fibrous structure with water; tumbling the fibrous structure in a dryer; heating the fibrous structure in a dryer; and combinations thereof.

Fibrous Element-forming Composition

The fibrous elements of the present invention are made from a fibrous element-forming composition. The fibrous element-forming composition is a polar-solvent-based composition. In one example, the fibrous element-forming composition is an aqueous composition comprising one or more fibrous element-forming materials and one or more active agents.

The fibrous element-forming composition may be processed at a temperature of from about 20° C. to about 100° C. and/or from about 30° C. to about 90° C. and/or from about 35° C. to about 70° C. and/or from about 40° C. to about 60° C. when making fibrous elements from the fibrous element-forming composition.

In one example, the fibrous element-forming composition may comprise at least 20% and/or at least 30% and/or at least 40% and/or at least 45% and/or at least 50% to about 90% and/or to about 85% and/or to about 80% and/or to about 75% by weight of one or more fibrous element-forming materials, one or more active agents, and mixtures thereof. The fibrous element-forming composition may comprise from about 10% to about 80% by weight of a polar solvent, such as water.

In one example, non-volatile components of the fibrous element-forming composition may comprise from about 20% and/or 30% and/or 40% and/or 45% and/or 50% to about 75% and/or 80% and/or 85% and/or 90% by weight based on the total weight of the fibrous element-forming composition. The non-volatile components may be composed of fibrous element-forming materials, such as backbone polymers, active agents and combinations thereof. Volatile components of the fibrous element-forming composition will comprise the remaining percentage and range from 10% to 80% by weight based on the total weight of the fibrous element-forming composition.

In a fibrous element spinning process, the fibrous elements need to have initial stability as they leave the spinning die. Capillary Number is used to characterize this initial stability criterion. At the conditions of the die, the Capillary Number may be at least 1 and/or at least 3 and/or at least 4 and/or at least 5.

In one example, the fibrous element-forming composition exhibits a Capillary Number of from at least about 1 to about 50 and/or at least about 3 to about 50 and/or at least about 5 to about 30 such that the fibrous element-forming composition can be effectively polymer processed into a fibrous element.

"Polymer processing" as used herein means any spinning operation and/or spinning process by which a fibrous element comprising a processed fibrous element-forming material is formed from a fibrous element-forming composition. The spinning operation and/or process may include spun bonding, melt blowing, electro-spinning, rotary spinning, continuous filament producing and/or tow fiber producing operations/processes. A "processed fibrous element-forming material" as used herein means any fibrous element-forming material that has undergone a melt processing operation and a subsequent polymer processing operation resulting in a fibrous element.

The Capillary Number is a dimensionless number used to characterize the likelihood of this droplet breakup. A larger Capillary Number indicates greater fluid stability upon exiting the die. The Capillary Number is defined as follows:

$$Ca = \frac{V * \eta}{\sigma}$$

V is the fluid velocity at the die exit (units of Length per Time),
$\eta$ is the fluid viscosity at the conditions of the die (units of Mass per Length*Time),
$\sigma$ is the surface tension of the fluid (units of mass per Time$^2$).
When velocity, viscosity, and surface tension are expressed in a set of consistent units, the resulting Capillary Number will have no units of its own; the individual units will cancel out.

The Capillary Number is defined for the conditions at the exit of the die. The fluid velocity is the average velocity of the fluid passing through the die opening. The average velocity is defined as follows:

$$V = \frac{Vol'}{Area}$$

Vol'=volumetric flowrate (units of Length$^3$ per Time),
Area=cross-sectional area of the die exit (units of Length$^2$).

When the die opening is a circular hole, then the fluid velocity can be defined as $$V = \frac{Vol'}{\pi * R^2}$$

R is the radius of the circular hole (units of length).

The fluid viscosity will depend on the temperature and may depend of the shear rate. The definition of a shear thinning fluid includes a dependence on the shear rate. The surface tension will depend on the makeup of the fluid and the temperature of the fluid.

In one example, the fibrous element-forming composition may comprise one or more release agents and/or lubricants. Non-limiting examples of suitable release agents and/or lubricants include fatty acids, fatty acid salts, fatty alcohols, fatty esters, sulfonated fatty acid esters, fatty amine acetates and fatty amides, silicones, aminosilicones, fluoropolymers and mixtures thereof.

In one example, the fibrous element-forming composition may comprise one or more antiblocking and/or detackifying agents. Non-limiting examples of suitable antiblocking and/or detackifying agents include starches, modified starches, crosslinked polyvinylpyrrolidone, crosslinked cellulose, microcrystalline cellulose, silica, metallic oxides, calcium carbonate, talc and mica.

Active agents of the present invention may be added to the fibrous element-forming composition prior to and/or during fibrous element formation and/or may be added to the fibrous element after fibrous element formation. For example, a perfume active agent may be applied to the fibrous element and/or fibrous structure comprising the fibrous element after the fibrous element and/or fibrous structure according to the present invention are formed. In another example, an enzyme active agent may be applied to the fibrous element and/or fibrous structure comprising the fibrous element after the fibrous element and/or fibrous structure according to the present invention are formed. In still another example, one or more particles, which may not be suitable for passing through the spinning process for making the fibrous element, may be applied to the fibrous element and/or fibrous structure comprising the fibrous element after the fibrous element and/or fibrous structure according to the present invention are formed.

Extensional Aids

In one example, the fibrous element comprises an extensional aid. Non-limiting examples of extensional aids can include polymers, other extensional aids, and combinations thereof.

In one example, the extensional aids have a weight-average molecular weight of at least about 500,000 Da. In another example, the weight average molecular weight of the extensional aid is from about 500,000 to about 25,000,000, in another example from about 800,000 to about 22,000,000, in yet another example from about 1,000,000 to about 20,000,000, and in another example from about 2,000,000 to about 15,000,000. The high molecular weight extensional aids are especially suitable in some examples of the invention due to the ability to increase extensional melt viscosity and reducing melt fracture.

The extensional aid, when used in a meltblowing process, is added to the composition of the present invention in an amount effective to visibly reduce the melt fracture and capillary breakage of fibers during the spinning process such that substantially continuous fibers having relatively consistent diameter can be melt spun. Regardless of the process employed to produce fibrous elements and/or particles, the extensional aids, when used, can be present from about 0.001% to about 10%, by weight on a dry fibrous element basis and/or dry particle basis and/or dry fibrous structure basis, in one example, and in another example from about 0.005 to about 5%, by weight on a dry fibrous element basis and/or dry particle basis and/or dry fibrous structure basis, in yet another example from about 0.01 to about 1%, by weight on a dry fibrous element basis and/or dry particle basis and/or dry fibrous structure basis, and in another example from about 0.05% to about 0.5%, by weight on a dry fibrous element basis and/or dry particle basis and/or dry fibrous structure basis.

Non-limiting examples of polymers that can be used as extensional aids can include alginates, carrageenans, pectin, chitin, guar gum, xanthum gum, agar, gum arabic, karaya gum, tragacanth gum, locust bean gum, alkylcellulose, hydroxyalkylcellulose, carboxyalkylcellulose, and mixtures thereof.

Non-limiting examples of other extensional aids can include modified and unmodified polyacrylamide, polyacrylic acid, polymethacrylic acid, polyvinyl alcohol, polyvinylacetate, polyvinylpyrrolidone, polyethylene vinyl acetate, polyethyleneimine, polyamides, polyalkylene oxides including polyethylene oxide, polypropylene oxide, polyethylenepropylene oxide, and mixtures thereof.

Dissolution Aids

The fibrous elements of the present invention may incorporate dissolution aids to accelerate dissolution when the fibrous element contains more than 40% surfactant to mitigate formation of insoluble or poorly soluble surfactant aggregates that can sometimes form or when the surfactant compositions are used in cold water. Non-limiting examples of dissolution aids include sodium chloride, sodium sulfate, potassium chloride, potassium sulfate, magnesium chloride, and magnesium sulfate.

Buffer System

The fibrous elements of the present invention may be formulated such that, during use in an aqueous cleaning operation, for example washing clothes or dishes and/or washing hair, the wash water will have a pH of between about 5.0 and about 12 and/or between about 7.0 and 10.5. In the case of a dishwashing operation, the pH of the wash water typically is between about 6.8 and about 9.0. In the case of washing clothes, the pH of the was water typically is between 7 and 11. Techniques for controlling pH at recommended usage levels include the use of buffers, alkalis, acids, etc., and are well known to those skilled in the art. These include the use of sodium carbonate, citric acid or sodium citrate, monoethanol amine or other amines, boric acid or borates, and other pH-adjusting compounds well known in the art.

Fibrous elements and/or fibrous structures useful as "low pH" detergent compositions are included in the present invention and are especially suitable for the surfactant systems of the present invention and may provide in-use pH values of less than 8.5 and/or less than 8.0 and/or less than 7.0 and/or less than 7.0 and/or less than 5.5 and/or to about 5.0.

Dynamic in-wash pH profile fibrous elements are included in the present invention. Such fibrous elements may use wax-covered citric acid particles in conjunction with other pH control agents such that (i) 3 minutes after contact with water, the pH of the wash liquor is greater than 10; (ii) 10 mins after contact with water, the pH of the wash liquor is less than 9.5; (iii) 20 mins after contact with water, the pH of the wash liquor is less than 9.0; and (iv) optionally, wherein, the equilibrium pH of the wash liquor is in the range of from above 7.0 to 8.5.

Non-limiting Example of Method for Making Fibrous Elements

Figure 7:
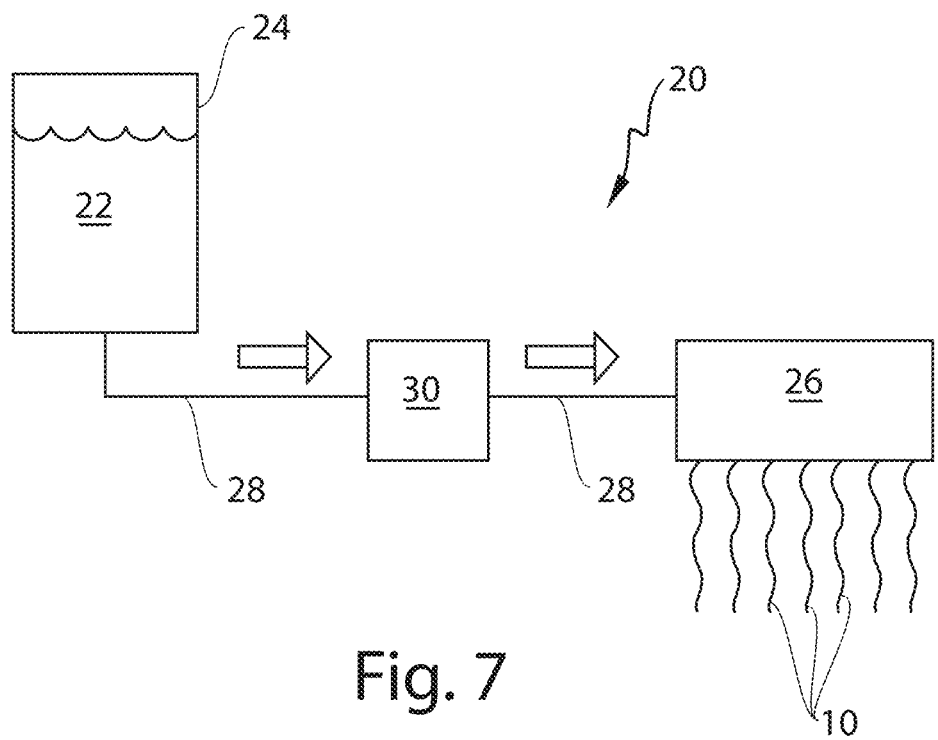
FIG. 7 is a schematic representation of an example of a process for making fibrous elements of the present invention.
Figure 8:
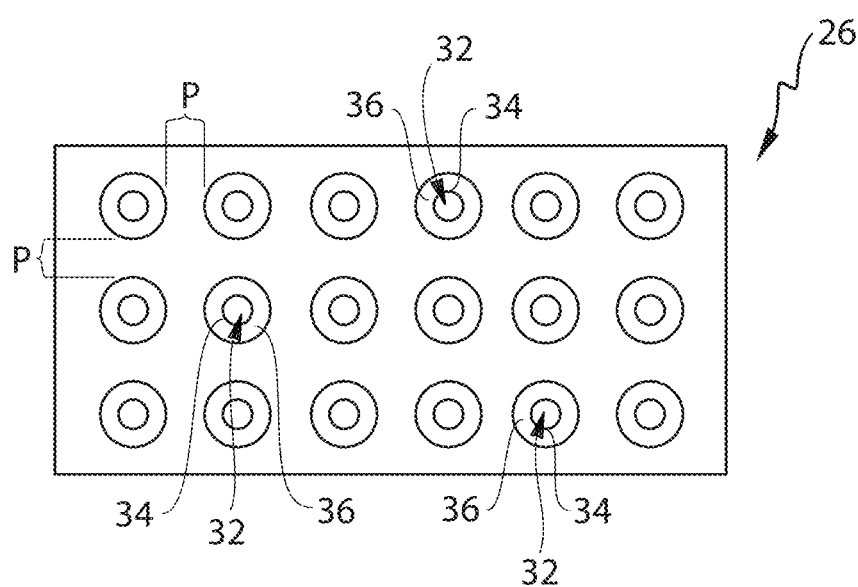
FIG. 8 is a schematic representation of an example of a die with a magnified view used in the process of FIG. 7.

The fibrous elements, for example filaments, of the present invention may be made as shown in FIGS. 7 and 8. As shown in FIGS. 7 and 8, a method 20 for making a fibrous element 10, for example filament, according to the present invention comprises the steps of:

a. providing a fibrous element-forming composition 22, such as from a tank 24, comprising one or more fibrous element-forming materials and one or more active agents; and b. spinning the fibrous element-forming composition 22, such as via a spinning die 26, into one or more fibrous elements 10, such as filaments, comprising the one or more fibrous element-forming materials and the one or more active agents.

The fibrous element-forming composition may be transported via suitable piping 28, with or without a pump 30, between the tank 24 and the spinning die 26. In one example, a pressurized tank 24, suitable for batch operation is filled with a suitable fibrous element-forming composition 22 for spinning A pump 30, such as a Zenith®, type PEP II, having a capacity of 5.0 cubic centimeters per revolution (cc/rev), manufactured by Colfax Corporation, Zenith Pumps Division, of Monroe, N.C., USA may be used to facilitate transport of the fibrous element-forming composition 22 to a spinning die 26. The flow of the fibrous element-forming composition 22 from the pressurized tank 24 to the spinning die 26 may be controlled by adjusting the number of revolutions per minute (rpm) of the pump 30. Pipes 28 are used to connect the pressurized tank 24, the pump 30, and the spinning die 26 in order to transport (as represented by the arrows) the fibrous element-forming composition 22 from the tank 24 to the pump 30 and into the die 26.

The total level of the one or more fibrous element-forming materials present in the fibrous element 10, when active agents are present therein, may be less than 80% and/or less than 70% and/or less than 65% and/or 50% or less by weight on a dry fibrous element basis and/or dry fibrous structure basis and the total level of the one or more active agents, when present in the fibrous element may be greater than 20% and/or greater than 35% and/or 50% or greater 65% or greater and/or 80% or greater by weight on a dry fibrous element basis and/or dry fibrous structure basis.

As shown in FIGS. 7 and 8, the spinning die 26 may comprise a plurality of fibrous element-forming holes 32 that include a melt capillary 34 encircled by a concentric attenuation fluid hole 36 through which a fluid, such as air, passes to facilitate attenuation of the fibrous element-forming composition 22 into a fibrous element 10 as it exits the fibrous element-forming hole 32.

In one example, the spinning die 26 shown in FIG. 8 has two or more rows of circular extrusion nozzles (fibrous element-forming holes 32) spaced from one another at a pitch P of about 1.524 millimeters (about 0.060 inches). The nozzles have individual inner diameters of about 0.305 millimeters (about 0.012 inches) and individual outside diameters of about 0.813 millimeters (about 0.032 inches). Each individual nozzle comprises a melt capillary 34 encircled by an annular and divergently flared orifice (concentric attenuation fluid hole 36) to supply attenuation air to each individual melt capillary 34. The fibrous element-forming composition 22 extruded through the nozzles is surrounded and attenuated by generally cylindrical, humidified air streams supplied through the orifices to produce fibrous elements 10.

Attenuation air can be provided by heating compressed air from a source by an electrical-resistance heater, for example, a heater manufactured by Chromalox, Division of Emerson Electric, of Pittsburgh, Pa., USA. An appropriate quantity of steam was added to saturate or nearly saturate the heated air at the conditions in the electrically heated, thermostatically controlled delivery pipe. Condensate was removed in an electrically heated, thermostatically controlled, separator.

The embryonic fibrous elements are dried by a drying air stream having a temperature from about 149° C. (about 300° F.) to about 315° C. (about 600° F.) by an electrical resistance heater (not shown) supplied through drying nozzles and discharged at an angle of about 90° relative to the general orientation of the embryonic fibrous elements being spun. The dried fibrous elements may be collected on a collection device, such as a belt or fabric, in one example a belt or fabric capable of imparting a pattern, for example a non-random repeating pattern to a fibrous structure formed as a result of collecting the fibrous elements on the belt or fabric. The addition of a vacuum source directly under the formation zone may be used to aid collection of the fibrous elements on the collection device. The spinning and collection of the fibrous elements produce a fibrous structure comprising inter-entangled, not side-by-side, not in a tow, not in a yarn, fibrous elements, for example filaments.

In one example, during the spinning step, any volatile solvent, such as water, present in the fibrous element-forming composition 22 is removed, such as by drying, as the fibrous element 10 is formed. In one example, greater than 30% and/or greater than 40% and/or greater than 50% of the weight of the fibrous element-forming composition's volatile solvent, such as water, is removed during the spinning step, such as by drying the fibrous element 10 being produced.

The fibrous element-forming composition may comprise any suitable total level of fibrous element-forming materials and any suitable level of active agents so long as the fibrous element produced from the fibrous element-forming composition comprises a total level of fibrous element-forming materials in the fibrous element of from about 5% to 50% or less by weight on a dry fibrous element basis and/or dry particle basis and/or dry fibrous structure basis and a total level of active agents in the fibrous element of from 50% to about 95% by weight on a dry fibrous element basis and/or dry particle basis and/or dry fibrous structure basis.

In one example, the fibrous element-forming composition may comprise any suitable total level of fibrous element-forming materials and any suitable level of active agents so long as the fibrous element produced from the fibrous element-forming composition comprises a total level of fibrous element-forming materials in the fibrous element and/or particle of from about 5% to 50% or less by weight on a dry fibrous element basis and/or dry particle basis and/or dry fibrous structure basis and a total level of active agents in the fibrous element and/or particle of from 50% to about 95% by weight on a dry fibrous element basis and/or dry particle basis and/or dry fibrous structure basis, wherein the weight ratio of fibrous element-forming material to total level of active agents is 1 or less.

In one example, the fibrous element-forming composition comprises from about 1% and/or from about 5% and/or from about 10% to about 50% and/or to about 40% and/or to about 30% and/or to about 20% by weight of the fibrous element-forming composition of fibrous element-forming materials; from about 1% and/or from about 5% and/or from about 10% to about 50% and/or to about 40% and/or to about 30% and/or to about 20% by weight of the fibrous element-forming composition of active agents; and from about 20% and/or from about 25% and/or from about 30% and/or from about 40% and/or to about 80% and/or to about 70% and/or to about 60% and/or to about 50% by weight of the fibrous element-forming composition of a volatile solvent, such as water. The fibrous element-forming composition may comprise minor amounts of other active agents, such as less than 10% and/or less than 5% and/or less than 3% and/or less than 1% by weight of the fibrous element-forming composition of plasticizers, pH adjusting agents, and other active agents.

The fibrous element-forming composition is spun into one or more fibrous elements and/or particles by any suitable spinning process, such as meltblowing, spunbonding, electro-spinning, and/or rotary spinning. In one example, the fibrous element-forming composition is spun into a plurality of fibrous elements and/or particles by meltblowing. For example, the fibrous element-forming composition may be pumped from a tank to a meltblown spinnerette. Upon exiting one or more of the fibrous element-forming holes in the spinnerette, the fibrous element-forming composition is attenuated with air to create one or more fibrous elements and/or particles. The fibrous elements and/or particles may then be dried to remove any remaining solvent used for spinning, such as the water.

The fibrous elements and/or particles of the present invention may be collected on a belt (not shown), such as a patterned belt, for example in an inter-entangled manner such that a fibrous structure comprising the fibrous elements and/or particles is formed.

Figure 9:
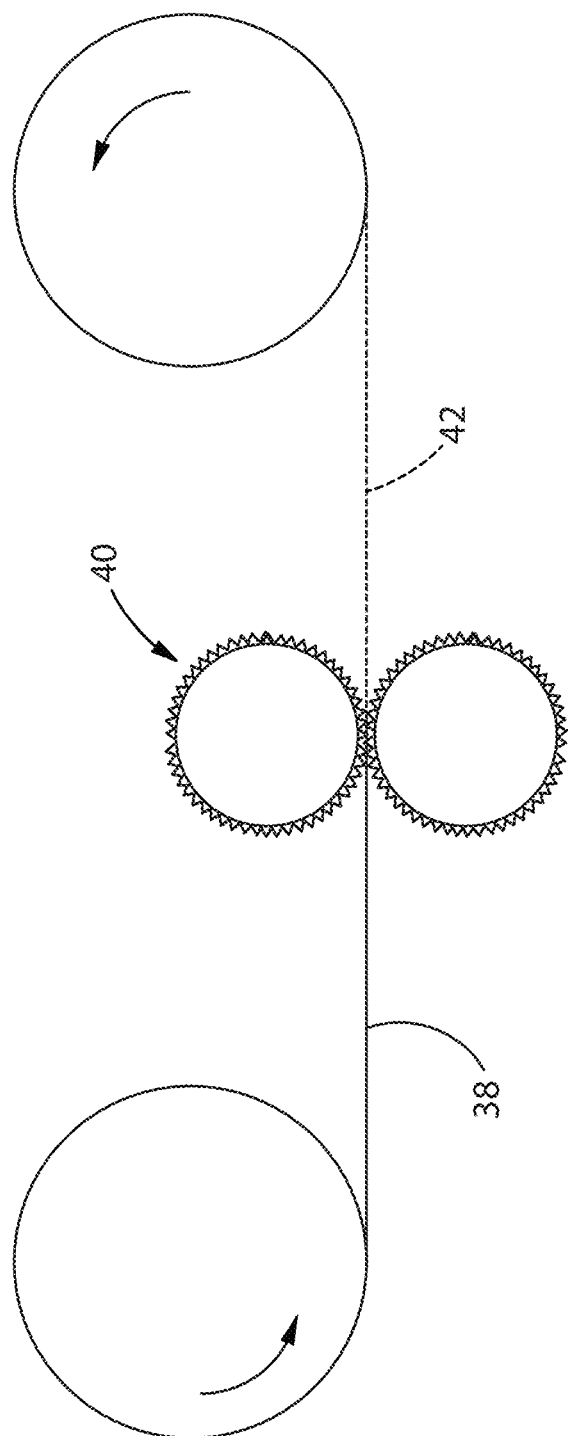
FIG. 9 is a schematic representation of an aperturing process according to the present invention.
Figure 10A:
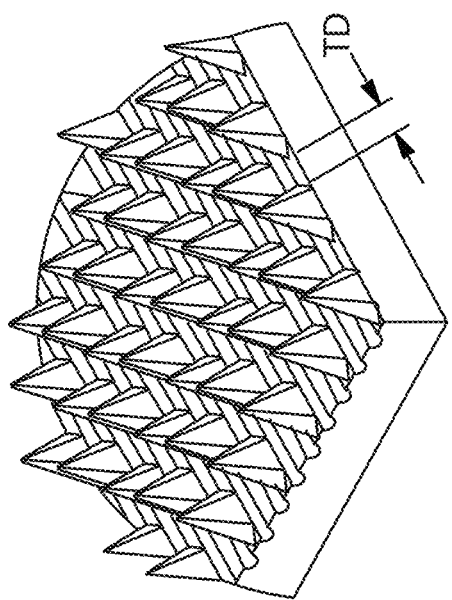
FIG. 10A is a perspective view of an example of a portion of a rotary knife aperturing apparatus.
Figure 10D:
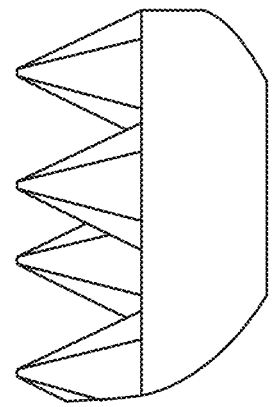
FIG. 10D is a side view of FIG. 10A.
Figure 10B:
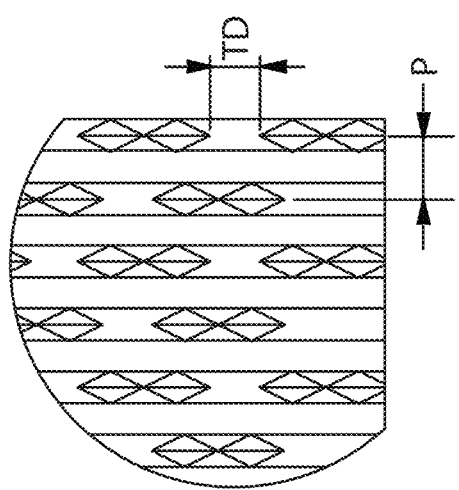
FIG. 10B is a top view of a portion of FIG. 10A.
Figure 10C:
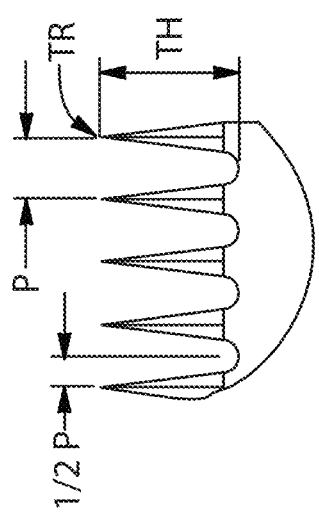
FIG. 10C is a front view of FIG. 10A.

Once the precursor fibrous structure has been formed, the precursor fibrous structure may be subjected to an aperturing process; namely, a process that imparts one or more apertures to the fibrous structure to produce an apertured fibrous structure. Non-limiting examples of such aperturing processes include embossing, rodding, rotary knife aperturing, pinning, die cutting, die punching, needlepunching, knurling, pneumatic forming, hydraulic forming, laser cutting, and tufting. FIG. 9 illustrates a non-limiting example of a suitable aperturing process. As shown in FIG. 9, a precursor fibrous structure 38 is subjected to an aperturing operation (aperturing process) 40, non-limiting examples of such are described above, which results in one or more apertures being imparted to the precursor fibrous structure 38 to form an apertured fibrous structure 42.

In one example, a precursor fibrous structure is subjected to a rotary knife aperturing operation as generally described in U.S. Pat. No. 8,679,391. In one example of a suitable rotary knife aperturing operation, a precursor fibrous structure is passed through a nip that comprises a 100 pitch toothed roll intermeshed with a 100 pitch ring roll. The teeth on the toothed roll have a pyramidal shape tip with six sides that taper from the base section of the tooth to a sharp point at the tip as shown in FIGS. 10A to 10D. The base section of the tooth has vertical leading and trailing edges and is joined to the pyramidal shape tip and the surface of the toothed roller. The teeth are oriented so the long direction runs in the machine direction (MD). The teeth are arranged in a staggered pattern, with a cross direction (CD) pitch P of 0.100 inch (2.5 mm) and a uniform tip to tip spacing in the MD (TD) of 0.223 inch (5.7 mm) The overall tooth height TH (including pyramidal and vertical base sections) is 0.270 inch (6.9 mm), the side wall angle on the long side of the tooth is 6.8 degrees and the side wall angle of the leading and trailing edges of the teeth in the pyramidal tip section is 25 degrees. The 100 pitch ring roll also has a CD pitch P of 0.100 inch, a tooth height TH of 0.270 inch, a tip radius TR of 0.005 inch, and a side wall angle of 4.7 degrees. The rotary knife aperturing roll and ring roll are aligned in the CD such that the clearances on either side of the teeth are about equal.

Figure 11A:
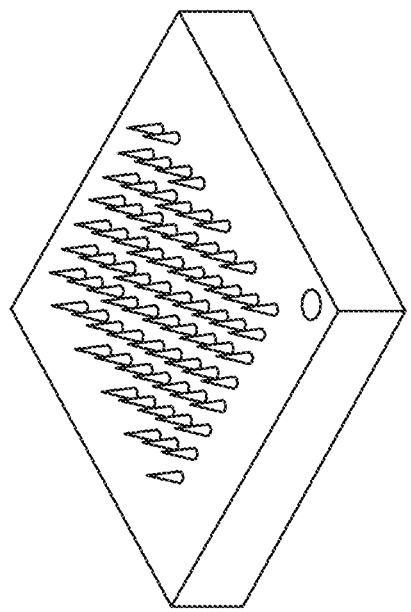
FIG. 11A is a perspective view of an example of a pinning aperturing apparatus.
Figure 11B:
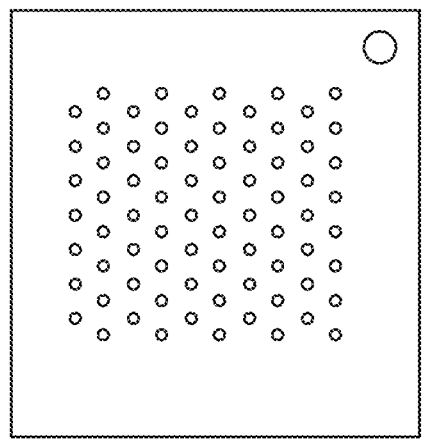
FIG. 11B is a top view of FIG. 11A.
Figure 11C:
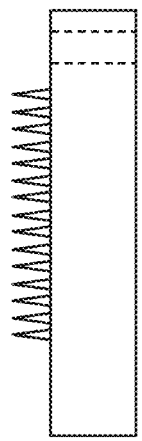
FIG. 11C is a side view of FIG. 11A.

In another example, the precursor fibrous structure is subjected to a pinning operation as described below. In one example, the precursor fibrous structure is passed through a nip that is formed between two opposing pin rollers of arranged in an intermeshing configuration so that pins from one roller pass through the space between pins on the opposing roller in the nip. A typical configurations may employ two rollers with the same pin design and arrangement. However, the opposing roller may be of a different pin design and arrangement, may instead not have pins, but other fibrous structure support members, or may be a solid surface comprised of a compliant material allowing for interference between the pins of the pinned roller and the compliant surface. The degree of interference between the virtual cylinders described by the tips of the pins is described as the Depth of Engagement. As the fibrous structure passes through the nip formed between the opposing rollers, the pins from each pinned roller engage with and penetrate the fibrous structure to a depth determined largely by the depth of engagement between the rollers and the nominal thickness of the fibrous structure. The pins used in the apparatus may be tapered pins having a circular cross section with a conical tip coming to a point as shown in FIGS. 11A-11C. The maximum diameter of the pins, from the surface of the roll up to the base of the conical section is 0.103 inch. The conical section has a wall angle of 9 degrees. The total pin length extending above the surface of the roller is 0.4050 inches. The pins are arranged in staggered machine direction rows, each row of pins having an MD pitch (center to center) of 0.358 inches along the virtual circle described by the tips of the pins. Adjacent rows are spaced 0.100 inches in the cross direction and offset circumferentially by half the MD pitch. Opposing rollers are aligned such that the corresponding MD rows of each roller are in the same plane and such that the pins intermesh in a gear-like fashion with opposing pins passing near the center of the space between pins in the opposing roller MD row of pins.

Methods of Use

In one example, the fibrous structures comprising one or more fabric care active agents according the present invention may be utilized in a method for treating a fabric article. The method of treating a fabric article may comprise one or more steps selected from the group consisting of: (a) pre-treating the fabric article before washing the fabric article; (b) contacting the fabric article with a wash liquor formed by contacting the fibrous structure or film with water; (c) contacting the fabric article with the fibrous structure or film in a dryer; (d) drying the fabric article in the presence of the fibrous structure or film in a dryer; and (e) combinations thereof.

In some embodiments, the method may further comprise the step of pre-moistening the fibrous structure or film prior to contacting it to the fabric article to be pre-treated. For example, the fibrous structure or film can be pre-moistened with water and then adhered to a portion of the fabric comprising a stain that is to be pre-treated. Alternatively, the fabric may be moistened and the fibrous structure or film placed on or adhered thereto. In some embodiments, the method may further comprise the step of selecting of only a portion of the fibrous structure or film for use in treating a fabric article. For example, if only one fabric care article is to be treated, a portion of the fibrous structure or film may be cut and/or torn away and either placed on or adhered to the fabric or placed into water to form a relatively small amount of wash liquor which is then used to pre-treat the fabric. In this way, the user may customize the fabric treatment method according to the task at hand. In some embodiments, at least a portion of a fibrous structure or film may be applied to the fabric to be treated using a device. Exemplary devices include, but are not limited to, brushes and sponges. Any one or more of the aforementioned steps may be repeated to achieve the desired fabric treatment benefit.

In another example, the fibrous structures or films comprising one or more hair care active agents according the present invention may be utilized in a method for treating hair. The method of treating hair may comprise one or more steps selected from the group consisting of: (a) pre-treating the hair before washing the hair; (b) contacting the hair with a wash liquor formed by contacting the fibrous structure or film with water; (c) post-treating the hair after washing the hair; (d) contacting the hair with a conditioning fluid formed by contacting the fibrous structure or film with water; and (e) combinations thereof.

Non-limiting Examples of Apertured Fibrous Structures

The following examples exemplify apertured fibrous structures according to the present invention. The precursor fibrous structures used in the examples is made as described hereinabove as shown in FIGS. 7 and 8.

EXAMPLE 1 (EX. 1)

A precursor fibrous structure comprising a plurality of filaments comprising one or more fibrous element-forming materials and one or more active agents having a nominal basis weight of 280 gsm and a thickness of approximately 1 mm is prepared and layered in stacks of 3 plies (forming a precursor multi-ply fibrous structure, in other words prior to aperturing), 100 mm wide, aligned with the CD of the precursor fibrous structure and 400 mm long in the MD as described above.

The precursor multi-ply fibrous structure is then apertured by passing the precursor multi-ply fibrous structure through a nip of a rotary knife aperturing apparatus as shown in FIGS. 9 and 10A to 10D and described further below. The precursor multi-ply fibrous structure is passed through a nip that comprises a 100 pitch toothed roll (rotary knife aperturing roll) intermeshed with a 100 pitch ring roll. The teeth on the toothed roll have a pyramidal shape tip with six sides that taper from the base section of the tooth to a sharp point at the tip. The base section of the tooth has vertical leading and trailing edges and is joined to the pyramidal shape tip and the surface of the toothed roller. The teeth are oriented so the long direction runs in the MD. The teeth are arranged in a staggered pattern, with a CD pitch P of 0.100 inch (2.5 mm) and a uniform tip to tip spacing in the MD of 0.223 inch (5.7 mm) The overall tooth height TH (including pyramidal and vertical base sections) is 0.270 inch (6.9 mm), the side wall angle on the long side of the tooth is 6.8 degrees and the side wall angle of the leading and trailing edges of the teeth in the pyramidal tip section is 25 degrees. The 100 pitch ring roll also has a CD pitch P of 0.100 inch, a tooth height TH of 0.270 inch, a tip radius TR of 0.005 inch, and a side wall angle of 4.7 degrees. The toothed roll (rotary knife aperturing roll) and ring roll are aligned in the CD such that the clearances on either side of the teeth are about equal. The depth of engagement between the toothed and ring rolls is set to about 0.130 inches. The precursor multi-ply fibrous structure is passed through the nip with essentially zero wrap around the rolls both ingoing and outgoing. While not required by the invention, a sacrificial polymeric spunbond web of approximately 20 gsm is passed through the nip between the multi-ply fibrous structure and the toothed roller to provide a convenient means to strip the multi-ply fibrous structure from the toothed roller. The multi-ply fibrous structure is passed through the nip at a speed of about 10 fpm. The resulting apertured multi-ply fibrous structure is cut into ovals of 40 mm×55 mm using a steel rule die.

Results from the Aperture Parameter Test Method for this apertured fibrous structure are shown below in Table 1.

Observation of the apertures in the resulting apertured multi-ply fibrous structure using the Optical Aperture Characterization Test Method described herein revealed well-formed apertures having an elongate shape, each aperture having a larger opening disposed towards one planar surface of the fibrous structure and a smaller opening disposed towards the opposite planar surface. All apertures are disposed such that the larger opening was towards the same generally planar surface, referred as the "tooth-side" surface. The typical aperture exhibits apparent minor and major axis widths at the tooth-side of about 0.6-1.1 mm and 2.6-3.1 mm, respectively. The typical aperture exhibits apparent minor and major axis widths at the non-tooth-side of about 0.2 to 1.9 mm. The apertures in the fibrous structure are characterized by an Average Optical Circular Diameter of 2.0 mm and an Average Optical Circular Area of 3.1 mm$^2$ as measured according to the Optical Aperture Characterization Test Method described herein.

EXAMPLE 2 (EX. 2)

A precursor fibrous structure comprising a plurality of filaments comprising one or more fibrous element-forming materials and one or more active agents having a nominal basis weight of 280 gsm and a thickness of approximately 1 mm is prepared in stacks of 3 plies (forming a precursor multi-ply fibrous structure), 100 mm wide, aligned with the CD of the precursor fibrous structure and 400 mm long in the MD.

The precursor multi-ply fibrous structure is then apertured by passing the multi-ply fibrous structure through a nip of a rotary pinning apparatus as shown in FIG. 9 and as described further below. The precursor multi-ply fibrous structure is passed through a nip that is formed between two opposing pin rollers having pins arranged in an intermeshing configuration so that pins from one roller pass through the space between the pins on the opposing roller in the nip. As the precursor multi-ply fibrous structure passes through the nip formed between the opposing pin rollers, the pins from each pinned roller engage with and penetrate the fibrous structure to a depth determined largely by the depth of engagement between the rollers and the nominal thickness of the fibrous structure. The pins of the pin rollers are tapered pins having a circular cross section with a conical tip coming to a point. The maximum diameter of the pins, from the surface of the roll up to the base of the conical section is 0.103 inch. The conical section has a wall angle of 9°. The total pin length extending above the surface of the pin roller is 0.4050 inches. The pins are arranged in staggered machine direction rows, each row of pins having an MD pitch (center to center) of 0.358 inches along the virtual circle described by the tips of the pins. Adjacent rows are spaced 0.100 inches in the cross direction and offset circumferentially by half the MD pitch. Opposing rollers are aligned such that the corresponding MD rows of each roller are in the same plane and such that the pins intermesh in a gear-like fashion with opposing pins passing near the center of the space between pins in the opposing roller MD row of pins. The depth of engagement between the pair of intermeshing pinned rollers is set to about 0.200 inches.

While not required by the invention, a sacrificial polymeric spunbond web of approximately 20 gsm is simultaneously passed through the nip between the multi-ply fibrous structure and the pinned rollers to provide a convenient means to strip the multi-ply fibrous structure from the pinned rollers.

The multi-ply fibrous structure is passed through the nip at a speed of about 10 fpm. The resulting apertured multi-ply fibrous structure is cut into ovals of 40 mm×55 mm using a steel rule die.

Results from the Aperture Parameter Test Method for this apertured fibrous structure are shown below in Table 1.

Observation of the resulting apertures in the multi-ply fibrous structure using the Optical Aperture Characterization Test Method described herein revealed well-formed, generally circular, apertures, each aperture having a larger opening disposed towards one planar surface of the fibrous structure and a smaller opening disposed towards the opposite planar surface. Approximately half of the apertures are disposed with the larger opening towards a first planar surface and the other approximately half of the apertures are disposed with the larger opening towards the opposite, second, planar surface. The larger openings of the apertures are characterized by an Average Optical Circular Diameter of 1.0 mm and an Average Optical Circular Area of 0.81 mm$^2$ as measured according to the Optical Aperture Characterization Test Method described herein. The smaller openings of the apertures are characterized by an Average Optical Circular Diameter of 0.14 mm and an Average Optical Circular Area of 0.015 mm$^2$ as measured according to the Optical Aperture Characterization Test Method described herein.

EXAMPLE 3 (EX. 3)

A precursor fibrous structure comprising a plurality of filaments comprising one or more fibrous element-forming materials and one or more active agents having a nominal basis weight of 280 gsm and thickness of approximately 1 mm is cut into a fibrous structure approximately 75 mm×75 mm.

The precursor fibrous structure is apertured in a flat plate pinning apparatus as generally shown in FIGS. 11A to 11C and further described below having a depth of engagement of 0.375 inches by pressing the plates together in a hydraulic press.

The apparatus comprises a pair of opposing plates, each plate having an array of tapered pins joined thereto, each pin perpendicular to the plane of the base plate. The pins are arranged in a staggered row arrangement of pins in which adjacent rows of pins in the Machine Direction are each shifted by half the MD pin pitch. The opposing plates are arranged such that pins intermesh when brought together in a direction perpendicular to the base plate.

The plates are provided with alignment pins that pass through both plates to ensure desired alignment of tapered pins.

The tapered pins have a circular cross section with a substantially cylindrical base section and a substantially conical tip section coming to a point. The maximum diameter of the pins, from the base plate up to the base of the conical section is 0.064 inch. The conical tip section has a wall angle of 7 degrees from the vertical. The total pin length extending above the surface of the roller is 0.5 inches.

The tapered pins are placed in alternating staggered rows having a Cross Direction pitch of 0.1 in and a vertical pitch of 0.358 in.

Results from the Aperture Parameter Test Method for this apertured fibrous structure are shown below in Table 1.

Observation of the resulting apertures in the fibrous structure using the Optical Aperture Characterization Test Method described herein revealed well-formed, generally circular, apertures, each aperture having a larger opening disposed towards one planar surface of the fibrous structure and a smaller opening disposed towards the opposite planar surface.

Approximately half of the apertures are disposed with the larger opening towards a first planar surface and the other approximately half of the apertures are disposed with the larger opening towards the opposite, second, planar surface. The larger openings of the apertures are characterized by an Average Optical Circular Diameter of 0.93 mm and an Average Optical Circular Area of 0.67 mm$^2$ as measured according to the Optical Aperture Characterization Test Method described herein. The smaller openings of the apertures are characterized by an Average Optical Circular Diameter of 0.44 mm and an Average Optical Circular Area of 0.15 mm$^2$ as measured according to the Optical Aperture Characterization Test Method described herein.

EXAMPLE 4 (EX. 4)

A precursor fibrous structure comprising a plurality of filaments comprising one or more fibrous element-forming materials and one or more active agents having a nominal basis weight of 280 gsm and thickness of approximately 1 mm is cut into a fibrous structure approximately 75 mm×75 mm.

The fibrous structure is apertured in a flat plate pinning apparatus as generally shown in FIGS. 11A to 11C and described further below having a depth of engagement of 0.375 inches by pressing the plates together in a hydraulic press.

The apparatus comprises a pair of opposing plates, each plate having an array of tapered pins joined thereto, each pin perpendicular to the plane of the base plate. The pins are arranged in a staggered row arrangement of pins in which adjacent rows of pins in the Machine Direction are each shifted by half the MD pin pitch. The opposing plates are arranged such that pins intermesh when brought together in a direction perpendicular to the base plate.

The plates are provided with alignment pins that pass through both plates to ensure desired alignment of tapered pins.

The tapered pins have a circular cross section with a substantially cylindrical base section and a substantially conical tip section coming to a point. The maximum diameter of the tapered pins, from the base plate up to the base of the conical section is 0.132 inch. The conical tip section has a wall angle of 7 degrees from the vertical. The total pin length extending above the surface of the roller is 0.5 inches.

The tapered pins are placed in alternating staggered rows having a Cross Direction pitch of 0.1 in and a vertical pitch of 0.358 in.

Results from the Aperture Parameter Test Method for this apertured fibrous structure are shown below in Table 1.

Observation of the resulting apertures in the aperture fibrous structure using the Optical Aperture Characterization Test Method described herein revealed irregularly shaped apertures each aperture having a larger opening disposed towards one planar surface of the fibrous structure and a smaller opening disposed towards the opposite planar surface. Approximately half of the apertures are disposed with the larger opening towards a first planar surface and the other approximately half of the apertures are disposed with the larger opening towards the opposite, second, planar surface. The larger openings of the apertures are characterized by an Average Optical Circular Diameter of 1.4 mm and an Average Optical Circular Area of 1.5 mm$^2$ as measured according to the Optical Aperture Characterization Test Method described herein. The smaller openings of the apertures are characterized by an Average Optical Circular Diameter of 0.88 mm and an Average Optical Circular Area of 0.61 mm$^2$ as measured according to the Optical Aperture Characterization Test Method described herein.

While not required by the invention, a sacrificial polymeric spunbond web of approximately 20 gsm is simultaneously passed through the nip between the multi-ply fibrous structure and the pinned rollers to provide a convenient means to strip the multi-ply fibrous structure from the pinned rollers.

The multi-ply fibrous structure is passed through the nip at a speed of about 10 fpm.

The resulting apertured multi-ply fibrous structure and control multi-ply fibrous structure (un-apertured) are measured according to the Tensile Test Method described herein. As shown in Table 2 below, it is observed that the Geometric Mean Secant Modulus of the apertured multi-ply fibrous structure is reduced compared to the un-apertured control multi-ply fibrous structure. While not wishing to be bound by theory, it is believed that the reduction in Geometric Mean Secant Modulus may correspond to an improved tactile impression of softness and flexibility of the end-use article. It is further expected that the reduction in Geometric Mean Secant Modulus will correspond to improved interaction with later processing steps, including, but not limited to, dispensing of the end-use article from primary packaging and/or dispensing devices designed for the convenience of the end user.

TABLE 1

|  | BWIR | BWITR | WRS | TRS | FOIR | AAA | AAED | AFOA |
|---|---|---|---|---|---|---|---|---|
| Ex. 1 | 0.593 | 1.070 | 0.0024 | 0.0006 | 1.094 | 0.753 | 0.973 | 4.5% |
| Ex. 2 | 0.570 | 1.032 | 0.0020 | 0.0003 | 1.134 | 0.217 | 0.504 | 1.8% |
| Ex. 3 | 0.531 | 1.070 | 0.0030 | 0.0009 | 1.151 | 0.204 | 0.502 | 1.5% |
| Ex. 4 | 0.590 | 1.100 | 0.0024 | 0.0007 | 1.178 | 0.677 | 0.912 | 5.2% |

EXAMPLE 5 (EX. 5)

A precursor fibrous structure comprising a plurality of filaments comprising one or more fibrous element-forming materials and one or more active agents having a nominal basis weight of 303 gsm and a thickness of approximately 1 mm is prepared by first humidifying the precursor fibrous structure by passing a handheld steam generation device over one surface of the precursor fibrous structure to plasticize the fibrous structure and then arranging the precursor fibrous structure in stacks of 3 plies (forming a multi-ply fibrous structure), 90 mm wide, aligned with the CD of the precursor fibrous structure, and 500 mm long in the MD and then applying a pressure of approximately 0.5 kPa over the surface of the multi-ply fibrous structure to bring the adjacent ply surfaces into intimate contact. The degree of humidification is selected to provide improved plasticity of the fibers at the surface to enhance inter-ply association of fibers without causing the fibrous structure to collapse, shrink, or otherwise become difficult to handle. The pressure is selected such that the multi-ply fibrous structure does not readily separate into individual plies while handling and such that the fibrous structure does not permanently collapse.

The multi-ply fibrous structure is then cut into two portions approximately 250 mm long. The first portion is retained as a control sample for subsequent characterization and the second portion is then apertured by passing the multi-ply fibrous structure through a nip of a pinning apparatus similar to Example 2 above. The depth of engagement between the pair of intermeshing pinned rollers was set to 0.130 inches.

EXAMPLE 6 (EX. 6)

A precursor fibrous structure comprising a plurality of filaments comprising one or more fibrous element-forming materials and one or more active agents having a nominal basis weight of 303 gsm and a thickness of approximately 1 mm is prepared by first humidifying the precursor fibrous structure by passing a handheld steam generation device over one surface of the precursor fibrous structure to plasticize the fibrous structure and then arranging the precursor fibrous structure in stacks of 3 plies (forming a multi-ply fibrous structure), 90 mm wide, aligned with the CD of the precursor fibrous structure, and 500 mm long in the MD and then applying a pressure of approximately 0.5 kPa over the surface of the multi-ply fibrous structure to bring the adjacent ply surfaces into intimate contact. The degree of humidification is selected to provide improved plasticity of the fibers at the surface to enhance inter-ply association of fibers without causing the fibrous structure to collapse, shrink, or otherwise become difficult to handle. The pressure is selected such that the multi-ply fibrous structure does not readily separate into individual plies while handling and such that the fibrous structure does not permanently collapse.

The multi-ply fibrous structure is then cut into two portions approximately 250 mm long. The first portion is retained as a control sample for subsequent characterization and the second portion is then apertured by passing the multi-ply fibrous structure through a nip of a pinning apparatus similar to Example 2 above. The depth of engagement between the pair of intermeshing pinned rollers was set to 0.100 inches.

While not required by the invention, a sacrificial polymeric spunbond web of approximately 20 gsm is simultaneously passed through the nip between the multi-ply fibrous structure and the pinned rollers to provide a convenient means to strip the multi-ply fibrous structure from the pinned rollers.

The multi-ply fibrous structure is passed through the nip at a speed of about 10 fpm.

The resulting apertured multi-ply fibrous structure and control multi-ply fibrous structure (un-apertured) are measured according to the Tensile Test Method described herein. As shown in Table 2 below, it is observed that the Geometric Mean Secant Modulus of the apertured multi-ply fibrous structure is reduced compared to the un-apertured control multi-ply fibrous structure. While not wishing to be bound by theory, it is believed that the reduction in Geometric Mean Secant Modulus may correspond to an improved tactile impression of softness and flexibility of the end-use article. It is further expected that the reduction in Geometric Mean Secant Modulus will correspond to improved interaction with later processing steps, including, but not limited to, dispensing of the end-use article from primary packaging and/or dispensing devices designed for the convenience of the end user.

TABLE 2

| | Control for Ex. 5 | Ex. 5 | Control for Ex. 6 | Ex. 6 |
|---|---|---|---|---|
| Geometric Mean Dry Tensile (g/cm) | 3447 | 2212 | 2912 | 2270 |
| Geometric Mean Peak Elongation (%) | 76.9 | 71.7 | 65.1 | 60.1 |
| Geometric Mean TEA ((g*cm/cm$^2$) | 0.32 | 0.16 | 0.21 | 0.13 |
| Geometric Mean Tangent Modulus (g/cm) | 3046 | 1766 | 3635 | 2862 |
| Geometric Mean Secant Modulus (g/cm) | 1968 | 729 | 2006 | 867 |

Test Methods

Unless otherwise indicated, all tests described herein including those described under the Definitions section and the following test methods are conducted on samples that have been conditioned in a conditioned room at a temperature of 23° C.±1° C. and a relative humidity of 50%±2% for 2 hours prior to the test unless otherwise indicated. Samples conditioned as described herein are considered dry samples (such as "dry filaments") for purposes of this invention. Further, all tests are conducted in such conditioned room.

Water Content Test Method

The water (moisture) content present in a filament and/or fiber and/or fibrous structure is measured using the following Water Content Test Method.

A filament and/or fibrous structure or portion thereof ("sample") is placed in a conditioned room at a temperature of 23° C.±1° C. and a relative humidity of 50%±2% for at least 24 hours prior to testing. The weight of the sample is recorded when no further weight change is detected for at least a 5 minute period. Record this weight as the "equilibrium weight" of the sample. Next, place the sample in a drying oven for 24 hours at 70° C. with a relative humidity of about 4% to dry the sample. After the 24 hours of drying, immediately weigh the sample. Record this weight as the "dry weight" of the sample. The water (moisture) content of the sample is calculated as follows:

$$\% \text{ Water (moisture) in sample} = 100\% \times \frac{(\text{Equilibrium weight of sample} - \text{Dry weight of sample})}{\text{Dry weight of sample}}$$

The % Water (moisture) in sample for 3 replicates is averaged to give the reported % Water (moisture) in sample.

Dissolution Test Method

Apparatus and Materials (FIGS. 12 Through 14):
  600 mL Beaker 44
  Magnetic Stirrer 46 (Labline Model No. 1250 or equivalent)
  Magnetic Stirring Rod 48 (5 cm)
  Thermometer (1 to 100° C.+1-1° C.)
  Cutting Die—Stainless Steel cutting die with dimensions 3.8 cm×3.2 cm
  Timer (0-3,600 seconds or 1 hour), accurate to the nearest second. Timer used should have sufficient total time measurement range if sample exhibits dissolution time greater than 3,600 seconds. However, timer needs to be accurate to the nearest second.
  Polaroid 35 mm Slide Mount 50 (commercially available from Polaroid Corporation or equivalent)
  35 mm Slide Mount Holder 52 (or equivalent)

City of Cincinnati Water or equivalent having the following properties: Total Hardness=155 mg/L as $CaCO_3$; Calcium content=33.2 mg/L; Magnesium content=17.5 mg/L; Phosphate content=0.0462.

Test Protocol

Equilibrate samples in constant temperature and humidity environment of 23° C.±1° C. and 50% RH±2% for at least 2 hours.

Measure the basis weight of the sample materials using Basis Weight Method defined herein.

Cut three dissolution test specimens from nonwoven structure sample, for example fibrous structure sample, using cutting die (3.8 cm×3.2 cm), so it fits within the 35 mm slide mount 50 which has an open area dimensions 24×36 mm.

Lock each specimen in a separate 35 mm slide mount 50.
Place magnetic stirring rod 48 into the 600 mL beaker 44.
Turn on the city water tap flow (or equivalent) and measure water temperature with thermometer and, if necessary, adjust the hot or cold water to maintain it at the testing temperature. Testing temperature is 15° C.±1° C. water. Once at testing temperature, fill beaker 240 with 500 mL±5 mL of the 15° C.±1° C. city water.

Place full beaker 44 on magnetic stirrer 46, turn on stirrer 46, and adjust stir speed until a vortex develops and the bottom of the vortex is at the 400 mL mark on the beaker 44.

Figure 3A:
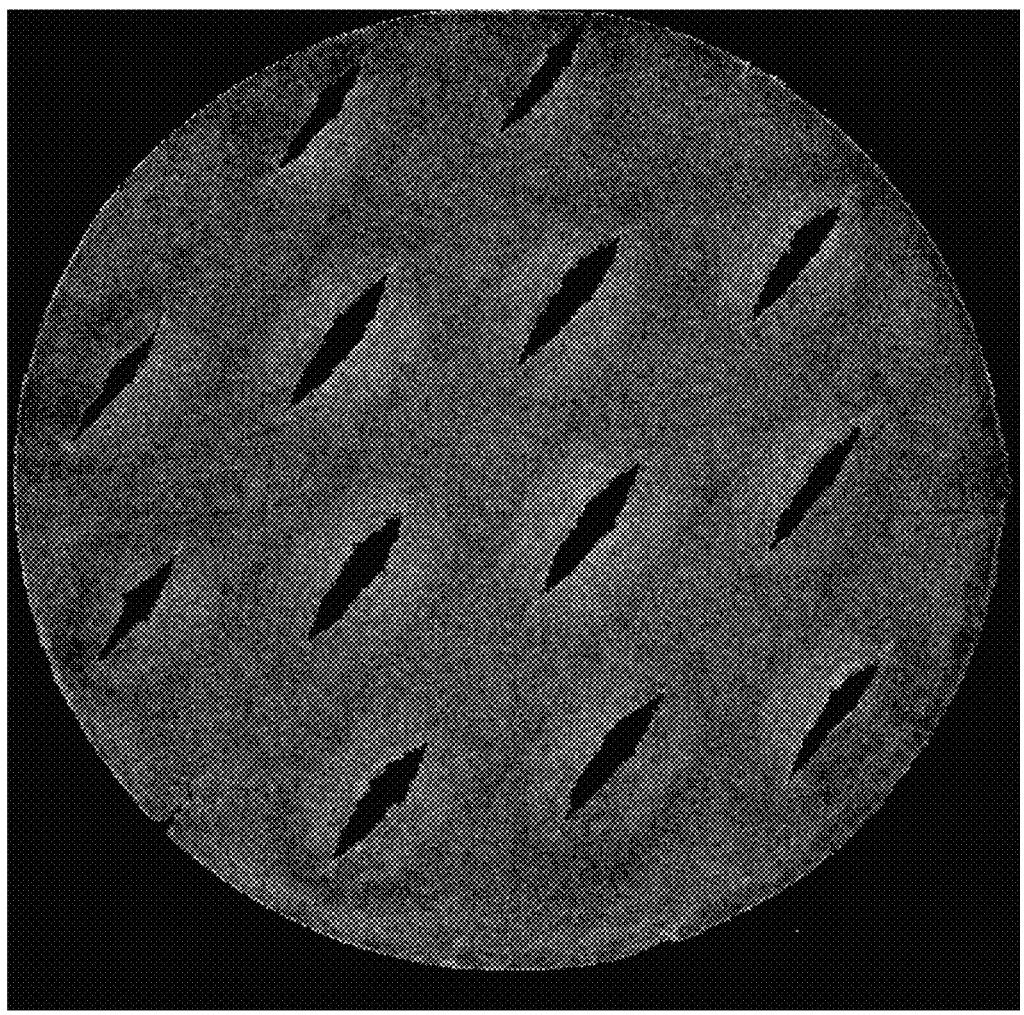
FIG. 3A is a microCT image of an example of a fibrous structure comprising apertures according to the present invention.
Figure 3B:
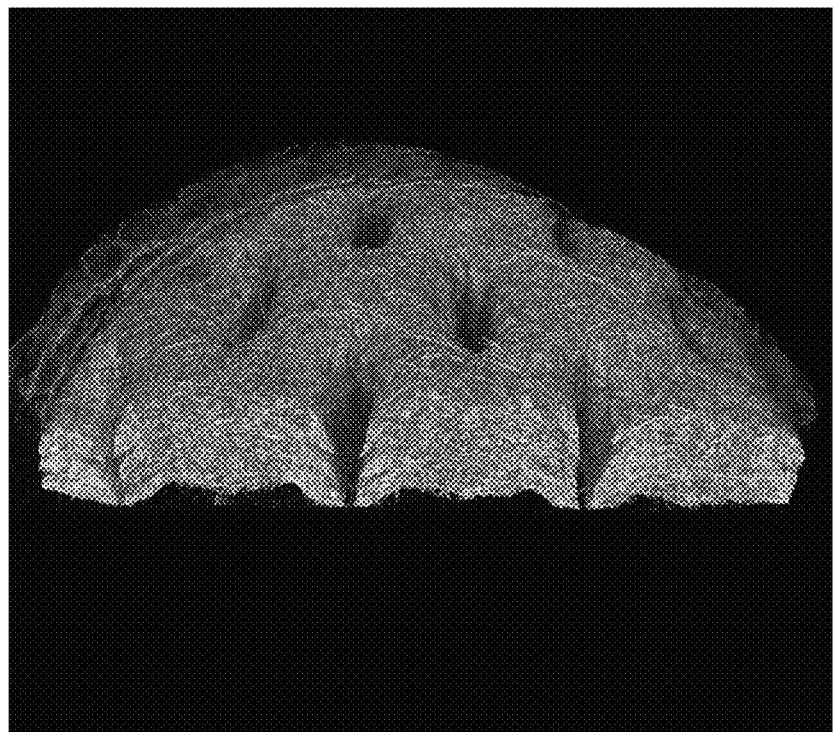
FIG. 3B is a partial, perspective view of the image of FIG. 3A.
Figure 3C:
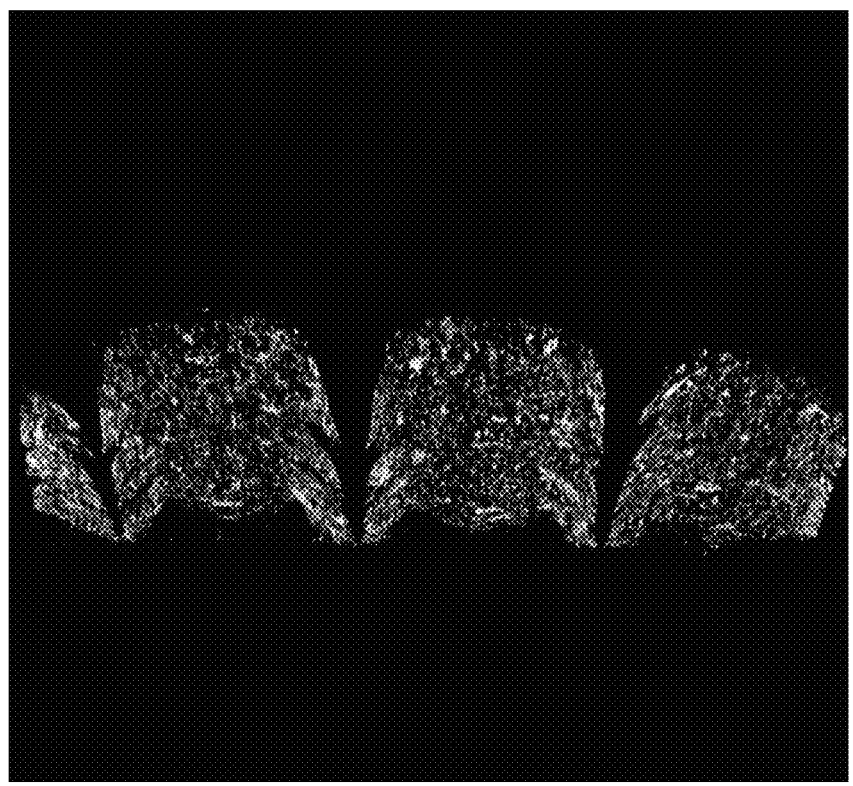
FIG. 3C is a cross-sectional view of the image of FIG. 3B.
Figure 4:
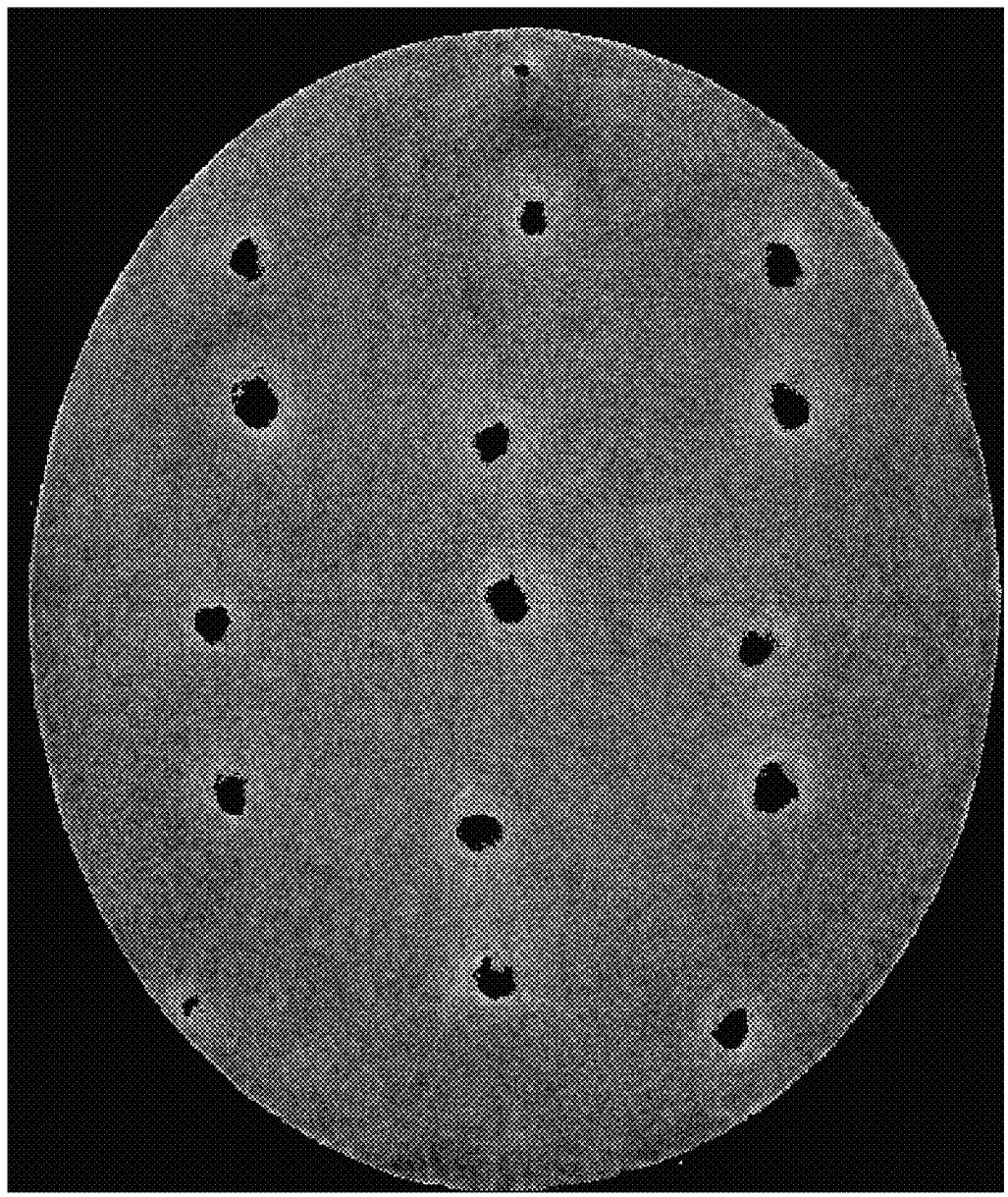
FIG. 4 is a microCT image of another example of a fibrous structure comprising apertures according to the present invention.
Figure 5:
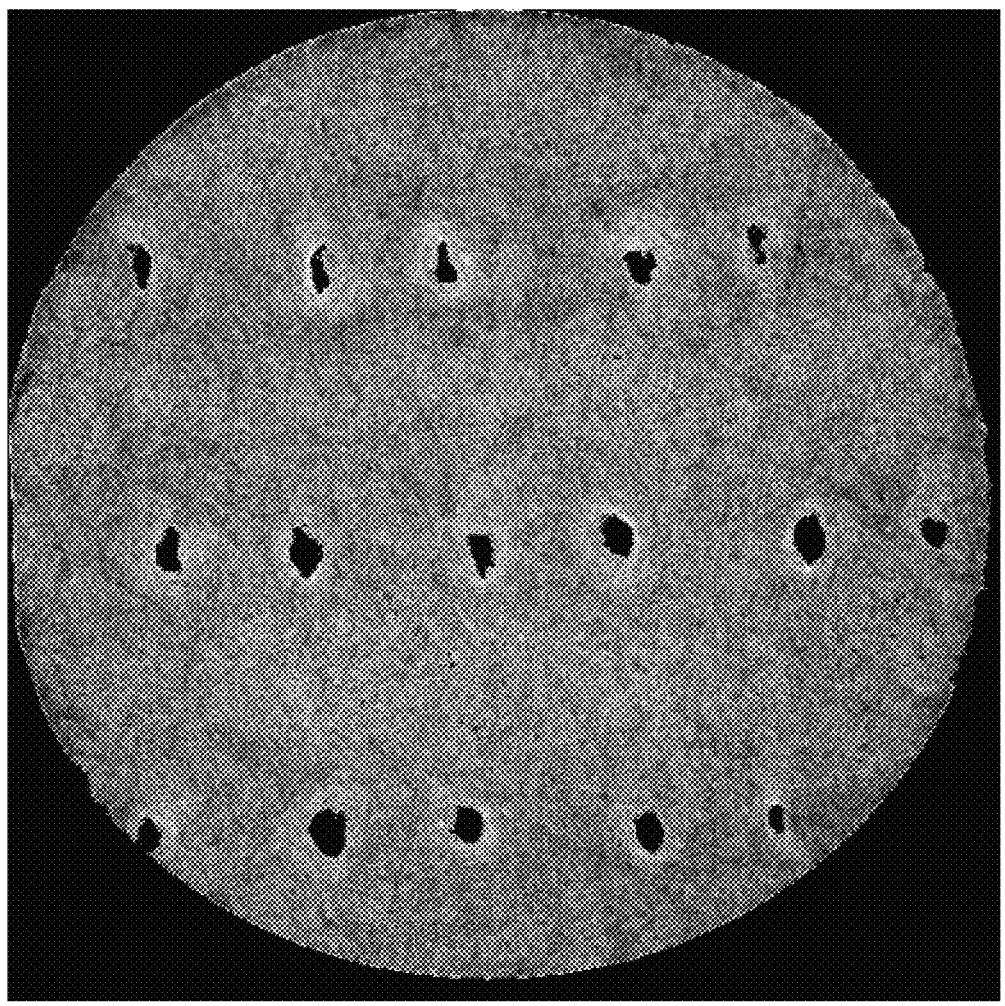
FIG. 5 is a microCT image of another example of a fibrous structure comprising apertures according to the present invention.
Figure 6:
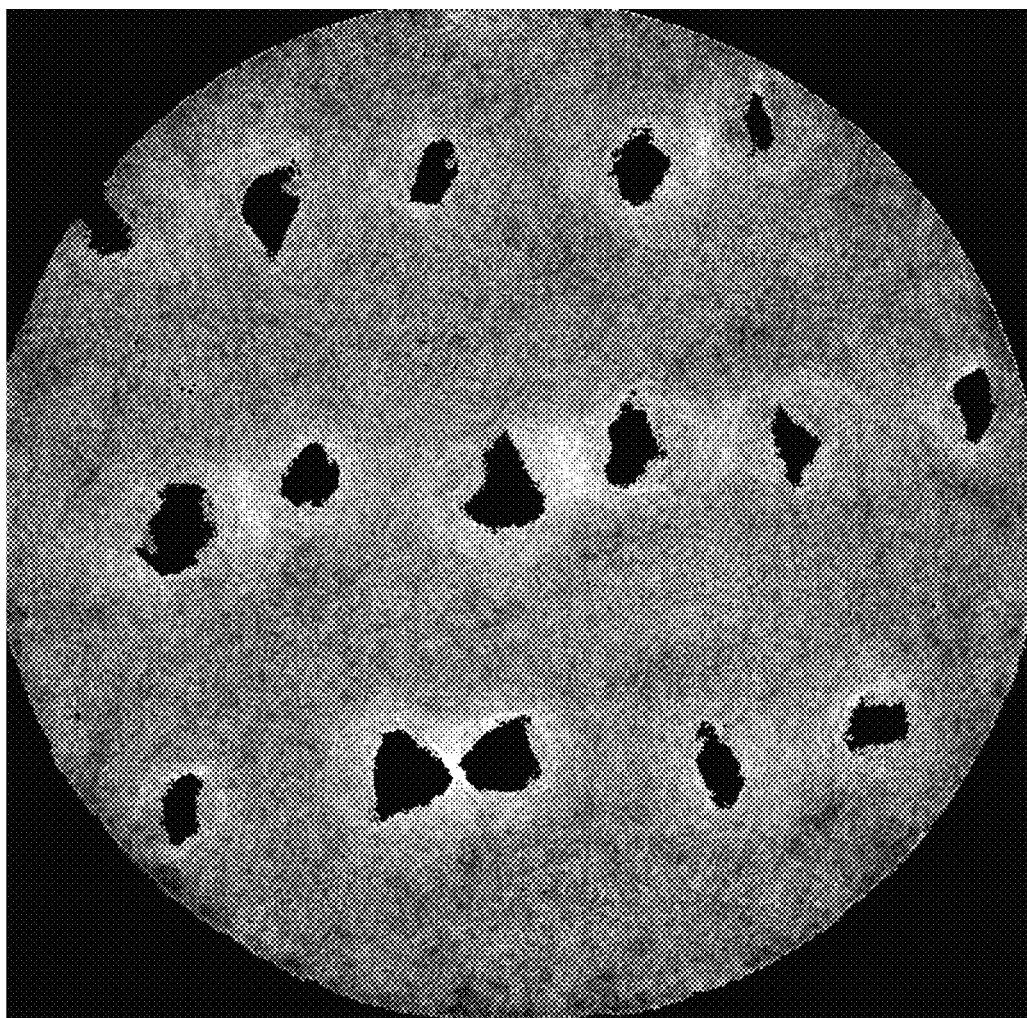
FIG. 6 is a microCT image of another example of a fibrous structure comprising apertures according to the present invention.

Secure the 35 mm slide mount 50 in the alligator clamp 54 of the 35 mm slide mount holder 52 such that the long end 56 of the slide mount 50 is parallel to the water surface. The alligator clamp 54 should be positioned in the middle of the long end 56 of the slide mount 50. The depth adjuster 58 of the holder 52 should be set so that the distance between the bottom of the depth adjuster 58 and the bottom of the alligator clamp 54 is 11±0.125 inches. This set up will position the sample surface perpendicular to the flow of the water. A slightly modified example of an arrangement of a 35 mm slide mount and slide mount holder are shown in FIGS. 1-3 of U.S. Pat. No. 6,787,512.

In one motion, drop the secured slide and clamp into the water and start the timer. The sample is dropped so that the sample is centered in the beaker. Disintegration occurs when the nonwoven structure breaks apart. Record this as the disintegration time. When all of the visible nonwoven structure is released from the slide mount, raise the slide out of the water while continuing the monitor the solution for undissolved nonwoven structure fragments. Dissolution occurs when all nonwoven structure fragments are no longer visible. Record this as the dissolution time.

Three replicates of each sample are run and the average disintegration and dissolution times are recorded. Average disintegration and dissolution times are in units of seconds.

The average disintegration and dissolution times are normalized for basis weight by dividing each by the sample basis weight as determined by the Basis Weight Method defined herein. Basis weight normalized disintegration and dissolution times are in units of seconds/gsm of sample ($s/(g/m^2)$).

Diameter Test Method

The diameter of a discrete filament or a filament within a fibrous structure or film is determined by using a Scanning Electron Microscope (SEM) or an Optical Microscope and an image analysis software. A magnification of 200 to 10,000 times is chosen such that the filaments are suitably enlarged for measurement. When using the SEM, the samples are sputtered with gold or a palladium compound to avoid electric charging and vibrations of the filament in the electron beam. A manual procedure for determining the filament diameters is used from the image (on monitor screen) taken with the SEM or the optical microscope. Using a mouse and a cursor tool, the edge of a randomly selected filament is sought and then measured across its width (i.e., perpendicular to filament direction at that point) to the other edge of the filament. A scaled and calibrated image analysis tool provides the scaling to get actual reading in μm. For filaments within a fibrous structure or film, several filament are randomly selected across the sample of the fibrous structure or film using the SEM or the optical microscope. At least two portions the fibrous structure or film (or web inside a product) are cut and tested in this manner. Altogether at least 100 such measurements are made and then all data are recorded for statistical analysis. The recorded data are used to calculate average (mean) of the filament diameters, standard deviation of the filament diameters, and median of the filament diameters.

Another useful statistic is the calculation of the amount of the population of filaments that is below a certain upper limit. To determine this statistic, the software is programmed to count how many results of the filament diameters are below an upper limit and that count (divided by total number of data and multiplied by 100%) is reported in percent as percent below the upper limit, such as percent below 1 micrometer diameter or %-submicron, for example. We denote the measured diameter (in μm) of an individual circular filament as di.

In case the filaments have non-circular cross-sections, the measurement of the filament diameter is determined as and set equal to the hydraulic diameter which is four times the cross-sectional area of the filament divided by the perimeter of the cross-section of the filament (outer perimeter in case of hollow filaments). The number-average diameter, alternatively average diameter is calculated as:

$$d_{num} = \frac{\sum_{i=1}^{n} d_i}{n}$$

Thickness Method

Thickness of a fibrous structure or film is measured by cutting 5 samples of a fibrous structure or film sample such that each cut sample is larger in size than a load foot loading surface of a VIR Electronic Thickness Tester Model II available from Thwing-Albert Instrument Company, Philadelphia, Pa. Typically, the load foot loading surface has a circular surface area of about 3.14 $in^2$. The sample is confined between a horizontal flat surface and the load foot loading surface. The load foot loading surface applies a confining pressure to the sample of 15.5 $g/cm^2$. The caliper of each sample is the resulting gap between the flat surface and the load foot loading surface. The caliper is calculated as the average caliper of the five samples. The result is reported in millimeters (mm).

Basis Weight Test Method

Basis weight of a fibrous structure sample is measured by selecting twelve (12) individual fibrous structure samples and making two stacks of six individual samples each. If the individual samples are connected to one another vie perforation lines, the perforation lines must be aligned on the same side when stacking the individual samples. A precision cutter is used to cut each stack into exactly 3.5 in.×3.5 in. squares. The two stacks of cut squares are combined to make a basis weight pad of twelve squares thick. The basis weight pad is then weighed on a top loading balance with a minimum resolution of 0.01 g. The top loading balance must be protected from air drafts and other disturbances using a draft shield. Weights are recorded when the readings on the top loading balance become constant. The Basis Weight is calculated as follows:

Basis Weight (lbs/3000 $ft^2$) =

$$\frac{\text{Weight of basis weight pad (g)} \times 3000 \text{ ft}^2}{453.6 \text{ g/lbs} \times 12 \text{ samples} \times [12.25 \text{ in}^2 \text{ (Area of basis weight pad)}/144 \text{ in}^2]}$$

Basis Weight ($g/m^2$) =

$$\frac{\text{Weight of basis weight pad (g)} \times 10,000 \text{ cm}^2/\text{m}^2}{79.0321 \text{ cm}^2 \text{ (Area of basis weight pad)} \times 12 \text{ samples}}$$

If fibrous structure sample is smaller than 3.5 in.×3.5 in., then smaller sampling areas can be used for basis weight determination with associated changes to calculations.

Weight Average Molecular Weight Test Method

The weight average molecular weight (Mw) of a material, such as a polymer, is determined by Gel Permeation Chromatography (GPC) using a mixed bed column. A high performance liquid chromatograph (HPLC) having the following components: Millenium®, Model 600E pump, system controller and controller software Version 3.2, Model 717 Plus autosampler and CHM-009246 column heater, all manufactured by Waters Corporation of Milford, Mass., USA, is utilized. The column is a PL gel 20 μm Mixed A column (gel molecular weight ranges from 1,000 g/mol to 40,000,000 g/mol) having a length of 600 mm and an internal diameter of 7.5 mm and the guard column is a PL gel 20 μm, 50 mm length, 7.5 mm ID. The column temperature is 55° C. and the injection volume is 200 μL. The detector is a DAWN® Enhanced Optical System (EOS) including Astra® software, Version 4.73.04 detector software, manufactured by Wyatt Technology of Santa Barbara, Calif., USA, laser-light scattering detector with K5 cell and 690 nm laser. Gain on odd numbered detectors set at 101.

Gain on even numbered detectors set to 20.9. Wyatt Technology's Optilab® differential refractometer set at 50° C. Gain set at 10. The mobile phase is HPLC grade dimethylsulfoxide with 0.1% w/v LiBr and the mobile phase flow rate is 1 mL/min, isocratic. The run time is 30 minutes.

A sample is prepared by dissolving the material in the mobile phase at nominally 3 mg of material/1 mL of mobile phase. The sample is capped and then stirred for about 5 minutes using a magnetic stirrer. The sample is then placed in an 85° C. convection oven for 60 minutes. The sample is then allowed to cool undisturbed to room temperature. The sample is then filtered through a 5 μm Nylon membrane, type Spartan-25, manufactured by Schleicher & Schuell, of Keene, N.H., USA, into a 5 milliliter (mL) autosampler vial using a 5 mL syringe.

For each series of samples measured (3 or more samples of a material), a blank sample of solvent is injected onto the column. Then a check sample is prepared in a manner similar to that related to the samples described above. The check sample comprises 2 mg/mL of pullulan (Polymer Laboratories) having a weight average molecular weight of 47,300 g/mol. The check sample is analyzed prior to analyzing each set of samples. Tests on the blank sample, check sample, and material test samples are run in duplicate. The final run is a run of the blank sample. The light scattering detector and differential refractometer is run in accordance with the "Dawn EOS Light Scattering Instrument Hardware Manual" and "Optilab® DSP Interferometric Refractometer Hardware Manual," both manufactured by Wyatt Technology Corp., of Santa Barbara, Calif., USA, and both incorporated herein by reference.

The weight average molecular weight of the sample is calculated using the detector software. A dn/dc (differential change of refractive index with concentration) value of 0.066 is used. The baselines for laser light detectors and the refractive index detector are corrected to remove the contributions from the detector dark current and solvent scattering. If a laser light detector signal is saturated or shows excessive noise, it is not used in the calculation of the molecular mass. The regions for the molecular weight characterization are selected such that both the signals for the 90° detector for the laser-light scattering and refractive index are greater than 3 times their respective baseline noise levels. Typically the high molecular weight side of the chromatogram is limited by the refractive index signal and the low molecular weight side is limited by the laser light signal.

The weight average molecular weight can be calculated using a "first order Zimm plot" as defined in the detector software. If the weight average molecular weight of the sample is greater than 1,000,000 g/mol, both the first and second order Zimm plots are calculated, and the result with the least error from a regression fit is used to calculate the molecular mass. The reported weight average molecular weight is the average of the two runs of the material test sample.

Tensile Test Method: Elongation, Tensile Strength, TEA and Modulus

Elongation, Tensile Strength, TEA, Secant Modulus and Tangent Modulus are measured on a constant rate of extension tensile tester with computer interface (a suitable instrument is the MTS Insight using Testworks 4.0 Software, as available from MTS Systems Corp., Eden Prairie, Minn.) using a load cell for which the forces measured are within 10% to 90% of the limit of the cell. Both the movable (upper) and stationary (lower) pneumatic jaws are fitted with rubber faced grips, 25.4 mm in height and wider than the width of the test specimen. An air pressure of about 80 psi is supplied to the jaws. All testing is performed in a conditioned room maintained at about 23° C.±1° C. and about 50%±2% relative humidity. Samples are conditioned under the same conditions for 2 hours before testing.

Eight specimens of nonwoven structure and/or dissolving fibrous structure are divided into two stacks of four specimens each. The specimens in each stack are consistently oriented with respect to machine direction (MD) and cross direction (CD). One of the stacks is designated for testing in the MD and the other for CD. Using a one inch precision cutter (Thwing Albert JDC-1-10, or similar) cut four MD strips from one stack, and four CD strips from the other, with dimensions of 2.54 cm±0.02 cm wide by at least 50 mm long.

Program the tensile tester to perform an extension test, collecting force and extension data at an acquisition rate of 100 Hz. Initially lower the crosshead 6 mm at a rate of 5.08 cm/min to introduce slack in the specimen, then raise the crosshead at a rate of 5.08 cm/min until the specimen breaks. The break sensitivity is set to 80%, i.e., the test is terminated when the measured force drops to 20% of the maximum peak force, after which the crosshead is returned to its original position.

Set the gage length to 2.54 cm. Zero the crosshead. Insert a specimen into the upper grip, aligning it vertically within the upper and lower jaws and close the upper grips. With the sample hanging from the top grips, zero the load cell. Insert the specimen into the lower grips and close. With the grips closed the specimen should be under enough tension to eliminate any slack but exhibits a force less than 3.0 g on the load cell. Start the tensile tester and data collection. Repeat testing in like fashion for all four CD and four MD specimens.

Program the software to calculate the following from the constructed force (g) verses extension (cm) curve:

Tensile Strength is the maximum peak force (g) divided by the specimen width (cm) and reported as g/cm to the nearest 1.0 g/cm.

Adjusted Gage Length is calculated as the extension measured at 3.0 g of force (cm) added to the original gage length (cm).

Elongation is calculated as the extension at maximum peak force (cm) divided by the Adjusted Gage Length (cm) multiplied by 100 and reported as % to the nearest 0.1%

Total Energy (TEA) is calculated as the area under the force curve integrated from zero extension to the extension at the maximum peak force (g*cm), divided by the product of the adjusted Gage Length (cm) and specimen width (cm) and is reported out to the nearest 1 g*cm/cm$^2$.

Replot the force (g) verses extension (cm) curve as a force (g) verses strain (%) curve.

Strain is herein defined as the extension (cm) divided by the Adjusted Gage Length (cm)×100.

Program the software to calculate the following from the constructed force (g) verses strain (%) curve:

The Secant Modulus is calculated from a least squares linear fit of the steepest slope of the force vs strain curve using a cord that has a rise of at least 20% of the peak force. This slope is then divided by the specimen width (2.54 cm) and reported to the nearest 1.0 g/cm.

Tangent Modulus is calculated as the slope the line drawn between the two data points on the force (g) versus strain (%) curve. The first data point used is the point recorded at 28 g force, and the second data point used is the point recorded at 48 g force. This slope is then divided by the specimen width (2.54 cm) and reported to the nearest 1.0 g/cm.

The Tensile Strength (g/cm), Elongation (%), Total Energy (g*cm/cm$^2$), Secant Modulus (g/cm) and Tangent Modulus (g/cm) are calculated for the four CD specimens and the four MD specimens. Calculate an average for each parameter separately for the CD and MD specimens.
Calculations:

Total Dry Tensile Strength(TDT)=MD Tensile Strength (g/cm)+CD Tensile Strength (g/cm)

Geometric Mean Tensile=Square Root of[MD Tensile Strength (g/cm)×CD Tensile Strength (g/cm)]

Tensile Ratio=MD Tensile Strength (g/cm)/CD Tensile Strength (g/cm)

Geometric Mean Peak Elongation=Square Root of[MD Elongation (%)×CD Elongation (%)]

Total TEA=MD TEA (g*cm/cm$^2$)+CD TEA (g*cm/cm$^2$)

Geometric Mean TEA=Square Root of[MD TEA (g*cm/cm$^2$)×CD TEA (g*cm/cm$^2$)]

Geometric Mean Tangent Modulus=Square Root of[MD Tangent Modulus (g/cm)×CD Tangent Modulus (g/cm)]

Total Tangent Modulus=MD Tangent Modulus (g/cm)+CD Tangent Modulus (g/cm)

Geometric Mean Secant Modulus=Square Root of[MD Secant Modulus (g/cm)×CD Secant Modulus (g/cm)]

Total Secant Modulus=MD Secant Modulus (g/cm)+CD Secant Modulus (g/cm)

Plate Stiffness Test Method

As used herein, the "Plate Stiffness" test is a measure of stiffness of a flat sample as it is deformed downward into a hole beneath the sample. For the test, the sample is modeled as an infinite plate with thickness "t" that resides on a flat surface where it is centered over a hole with radius "R". A central force "F" applied to the tissue directly over the center of the hole deflects the tissue down into the hole by a distance "w". For a linear elastic material the deflection can be predicted by:

$$w = \frac{3F}{4\pi Et^3}(1-v)(3+v)R^2$$

where "E" is the effective linear elastic modulus, "v" is the Poisson's ratio, "R" is the radius of the hole, and "t" is the thickness of the tissue, taken as the caliper in millimeters measured on a stack of 5 tissues under a load of about 0.29 psi. Taking Poisson's ratio as 0.1 (the solution is not highly sensitive to this parameter, so the inaccuracy due to the assumed value is likely to be minor), the previous equation can be rewritten for "w" to estimate the effective modulus as a function of the flexibility test results:

$$E \approx \frac{3R^2}{4t^3}\frac{F}{w}$$

The test results are carried out using an MTS Alliance RT/1 testing machine (MTS Systems Corp., Eden Prairie, Minn.) with a 100N load cell. As a stack of five tissue sheets at least 2.5-inches square sits centered over a hole of radius 15.75 mm on a support plate, a blunt probe of 3.15 mm radius descends at a speed of 20 mm/min. When the probe tip descends to 1 mm below the plane of the support plate, the test is terminated. The maximum slope in grams of force/mm over any 0.5 mm span during the test is recorded (this maximum slope generally occurs at the end of the stroke). The load cell monitors the applied force and the position of the probe tip relative to the plane of the support plate is also monitored. The peak load is recorded, and "E" is estimated using the above equation.

The Plate Stiffness "S" per unit width can then be calculated as:

$$S = \frac{Et^3}{12}$$

and is expressed in units of Newtons-millimeters. The Testworks program uses the following formula to calculate stiffness:

$$S=(F/w)[(3+v)R^2/16\pi]$$

wherein "F/w" is max slope (force divided by deflection), "v" is Poisson's ratio taken as 0.1, and "R" is the ring radius.

Filament Composition Test Method

In order to prepare filaments for filament composition measurement, the filaments must be conditioned by removing any coating compositions and/or materials present on the external surfaces of the filaments that are removable. A chemical analysis of the conditioned filaments is then completed to determine the compositional make-up of the filaments with respect to the fibrous element-forming materials and the active agents and the level of the fibrous element-forming materials and active agents present in the filaments.

The compositional make-up of the filaments with respect to the fibrous element-forming material and the active agents can also be determined by completing a cross-section analysis using TOF-SIMs or SEM. Still another method for determining compositional make-up of the filaments uses a fluorescent dye as a marker. In addition, as always, a manufacturer of filaments should know the compositions of their filaments.

Median Particle Size Test Method

This test method must be used to determine median particle size.

The median particle size test is conducted to determine the median particle size of the seed material using ASTM D 502-89, "Standard Test Method for Particle Size of Soaps and Other Detergents", approved May 26, 1989, with a further specification for sieve sizes used in the analysis. Following section 7, "Procedure using machine-sieving method," a nest of clean dry sieves containing U.S. Standard (ASTM E 11) sieves #8 (2360 um), #12 (1700 um), #16 (1180 um), #20 (850 um), #30 (600 um), #40 (425 um), #50 (300 um), #70 (212 um), #100 (150 um) is required. The prescribed Machine-Sieving Method is used with the above sieve nest. The seed material is used as the sample. A suitable sieve-shaking machine can be obtained from W.S. Tyler Company of Mentor, Ohio, U.S.A.

The data are plotted on a semi-log plot with the micron size opening of each sieve plotted against the logarithmic abscissa and the cumulative mass percent ($Q_3$) plotted against the linear ordinate. An example of the above data representation is given in ISO 9276-1:1998, "Representation of results of particle size analysis—Part 1: Graphical Representation", Figure A.4. The seed material median particle size ($D_{50}$), for the purpose of this invention, is defined as the abscissa value at the point where the cumulative mass percent is equal to 50 percent, and is calculated by a straight line interpolation between the data points directly above (a50) and below (b50) the 50% value using the following equation:

$$D_{50}=10^{\wedge}[\text{Log}(D_{a50})-(\text{Log}(D_{a50})-\text{Log}(D_{b50}))*(Q_{a50}-50\%)/(Q_{a50}-Q_{b50})]$$

where $Q_{a50}$ and $Q_{b50}$ are the cumulative mass percentile values of the data immediately above and below the $50^{th}$ percentile, respectively; and $D_{a50}$ and $D_{b50}$ are the micron sieve size values corresponding to these data.

In the event that the $50^{th}$ percentile value falls below the finest sieve size (150 um) or above the coarsest sieve size (2360 um), then additional sieves must be added to the nest following a geometric progression of not greater than 1.5, until the median falls between two measured sieve sizes.

The Distribution Span of the Seed Material is a measure of the breadth of the seed size distribution about the median. It is calculated according to the following:

$$\text{Span}=(D_{84}/D_{50}+D_{50}/D_{16})/2$$

Where $D_{50}$ is the median particle size and $D_{84}$ and $D_{16}$ are the particle sizes at the sixteenth and eighty-fourth percentiles on the cumulative mass percent retained plot, respectively.

In the event that the $D_{16}$ value falls below the finest sieve size (150 um), then the span is calculated according to the following:

$$\text{Span}=(D_{84}/D_{50}).$$

In the event that the $D_{84}$ value falls above the coarsest sieve size (2360 um), then the span is calculated according to the following:

$$\text{Span}=(D_{50}/D_{16}).$$

In the event that the $D_{16}$ value falls below the finest sieve size (150 um) and the $D_{84}$ value falls above the coarsest sieve size (2360 um), then the distribution span is taken to be a maximum value of 5.7.

Aperture Parameter Test Method

One of skill understands it is important to ensure that preparation steps for testing a fibrous structure sample do not damage the sample to be tested or alter the characteristics to be measured. A clean dry fibrous structure sample is the intended starting point for the measurements. The following test method is conducted on samples that have been conditioned at a temperature of 23° C.±2.0° C. and a relative humidity of 45%±10% for a minimum of 12 hours prior to the test. Except where noted all test steps are conducted in such a conditioned room, and all testing is conducted under the same environmental conditions. Any damaged fibrous structure is discarded. Samples that have defects such as unintended wrinkles, creases, tears, and alike are not tested. All instruments are calibrated according to manufacturer's specifications. Samples conditioned as described herein are considered dry samples for purposes of this invention.

Several parameters related to the presence of apertures in a fibrous structure are determined through the use of three-dimensional (3D) imaging and computerized image analysis. Micro X-ray computed tomography (microCT) is used to generate 3D renderings of test samples obtained from the fibrous structures comprising apertures. Each of the parameters determined by the method relate to one or more of the following characteristics: aperture characteristics, dimensions and frequency; localized basis weight index; or localized fiber orientation index. Image analysis tools are applied to the 3D renderings to generate two-dimensional (2D) images, and one-dimensional (1D) profiles of values. The profiles display the mean localized basis weight index, and the localized fiber orientation index, as a function of distance radiating outward from the edge of the Aperture Void Regions (as defined further below), for data combined from several replicate apertures. Within the profiles, distinct regions are identified according to their distance from the edge of the Aperture Void Regions and with regard to the relative values measured at characteristic distances. The Background Region is distal to the apertures' void region and is least affected by the apertures' presence. The Wall Region, when present, is immediately adjacent to the apertures' void region and can be depleted in local basis weight index versus that of the background region. The Transition Region, when present, is located between the wall region and the background region, and can exhibit an increased local basis weight index versus that of the background region. Several parameters are defined and calculated to characterize aspects of the relative basis weight index and the relative fiber orientation index between these regions. In total the aperture-related parameters determined include: Average Aperture Equivalent Diameter; Average Aperture Area; Aperture Frequency; Aperture Circularity; Average Fractional Open Area; Basis Weight Index Ratio; Basis Weight Index Transition Ratio; Wall Region Slope; Transition Region Slope; and Fiber Orientation Index Ratio.

Samples of the fibrous structure to be tested are imaged using a microCT X-ray scanning instrument capable of scanning a sample having dimensions of at least 16 mm×16 mm×3 mm as a single dataset with contiguous voxels. An isotropic spatial resolution of 6 μm is required in the datasets collected by microCT scanning One example of suitable instrumentation is the SCANCO Systems model μ50 microCT scanner (Scanco Medical AG, Brüttiselen, Switzerland) operated with the following settings: energy level of 45 kVp at 88 μA; 3000 projections; 20 mm field of view; 750 ms integration time; an averaging of 3; and a voxel size of 6 μm.

Fibrous structures to be tested are inspected visually to discern the presence, appearance, number and location of individual apertures. The inspections may be assisted by the use of a magnifying device to achieve clear and thorough observations. Test samples to be analyzed are prepared by punching sample discs of fibrous structure out of a fibrous structure, using a sharp circular punch tool of approximately 16 mm diameter. The punch tool is positioned such that at least one aperture is: present inside the punch disc, is located approximately centered over the central origin of the punch circle, and if possible is completely contained within the area of the sample disc being punched.

Fibrous structures to be tested are sampled by preparing a set of at least three sample discs from each material being tested. The three or more sample discs are carefully selected such that the collective set of all apertures present in the discs is representative of the variety of apertures present in the material being tested, and has the various apertures in approximately the same relative frequencies as present in the entire fibrous structure (i.e., different aperture varieties are number-weighted by their relative frequency, not area-weighted), as determined during the visual inspection. If three samples discs are insufficient to collectively provide such a representative sample of the entire fibrous structure, then additional sample discs are prepared in sufficient quantity for the set to collectively satisfy the specified requirements for a representative sample. All parameter value results specified in this test method are calculated and reported for the set of sample discs that are collectively representative of the entire fibrous structure.

Different classes of apertures and/or different zones of apertures may be visually discernible in the fibrous structure during the visual inspection. In one example, the fibrous structures of the present invention may comprise two or more classes of apertures such that the fibrous structure exhibits two or more different Average Aperture Equivalent Diameters as measured according to the Aperture Parameter Test Method described herein.

Different classes of apertures may be identified according to differences in the relative size of apertures, or by differences in the relative shape of the apertures, or by any other visually discernable and reoccurring characteristic(s) of the apertures. Different zones of apertures may be identified according to the relative frequency or density of apertures between areas of the fibrous structure, or by the relative shape(s) of the apertures between areas, or by the relative spatial arrangement or co-mingling of apertures between areas, or by any other visually discernable characteristic(s) of the apertures or their spatial arrangement. Zones may reoccur or repeat in any spatial arrangement on the fibrous structure, and as such may comprise areas within or between repeat patterns. Fibrous structures comprising different classes of apertures or different zones of apertures are visually assessed to determine if a 16 mm sample disc can be punched such that only a single class or zone is present in a single sample disc. For fibrous structures comprising more than one visually discernable class of apertures or zone of apertures and wherein the spatial arrangement of the apertures permits at least one class or zone to be sampled separately, then at least three replicate sample discs are prepared from each different class or zone that can be sampled separately (in addition to the set of sample discs that are collectively representative of the entire structure). For fibrous structures wherein different classes or zone of apertures can be sampled separately, all results specified in this test method (except for Aperture Frequency) are calculated and reported separately for each set of sample discs representative of a zone or class of apertures, in addition to the results reported for the set of sample discs representative of the entire structure.

The prepared sample discs are laid flat and may be mounted between discs (and/or annuli) of a low-attenuating sample preparation mounting foam, in alternating layers to form a stack. The use of foam annuli can provide regions within the scans where each sample disc is completely isolated from other solid material. The sample discs and any additional foam discs and/or annuli are mounted into a plastic cylindrical tube and secured inside the microCT scanner. The instrument's image acquisition settings are selected such that the image intensity contrast is sensitive enough to provide clear and reproducible discrimination of the fibrous structures from the air and the surrounding mounting foam. Image acquisition settings that are unable to achieve this contrast discrimination or the required spatial resolution are unsuitable for this method. Scans of the sample discs are captured such that the entire volume of all mounted sample discs is included in the dataset.

Software for conducting reconstructions of the dataset to generate 3D renderings is supplied by the scanning instrument manufacturer. Software suitable for subsequent image processing steps and quantitative image analysis includes programs such as Avizo Fire 8.0 (Visualization Sciences Group/FEI Company, Burlington, Mass., U.S.A.), and MATLAB 2013b with corresponding MATLAB Image Processing Toolbox (The Mathworks Inc. Natick, Mass., U.S.A.). MicroCT data collected with a gray level intensity depth of 16-bit is converted to a gray level intensity depth of 8-bit, taking care to ensure that the resultant 8-bit dataset maintains the maximum dynamic range and minimum number of saturated voxels feasible, while excluding extreme outlier values. The dataset is subsampled by a factor of two in all dimensions to produce a 3D dataset comprising 12 µm voxels, which is used in the subsequent image processing and analysis steps. Henceforth in this method, the Z dimension refers to the direction perpendicular to the plane of the sample disc, and the X and Y dimensions refer to two directions which are perpendicular to each other and which both lie parallel to the plane of the sample disc. The orientation of the perpendicular X and Y dimensions is determined arbitrarily by the rotational orientation of the mounted sample disc in relation to the instrument's scanning geometry. From a dataset comprising multiple scanned sample discs, a single and separate 3D Region of Interest (ROI) is created for each individual sample disc. The size of the 3D ROI for each sample disc is such that it comprises the entirety of that sample disc in the X, Y, and Z dimensions, and additionally comprises a significant volume of void air space/void voxels in the Z dimension above and/or below the plane of the disc. All extraneous solid material (e.g. sample mounting foam, sample holder) is digitally excluded from the data analyses.

Basis Weight Index Image

Gray level intensity values in the microCT dataset result from the attenuation of x-rays as they pass through the sample material during scanning. This x-ray attenuation is a function of the density of the sample material, such that materials of higher density result in higher gray level intensity values (brighter regions), and materials of lower density result in lower gray level intensity values (darker regions). This characteristic is used to determine localized basis weight index values, as represented at each pixel location in a 2D XY projection image termed the Basis Weight Index Image. To calculate the Basis Weight Index Image for each sample disc, a 2D XY cumulative projection image is created of each disc, via image math. In the Z stack of XY image slices that comprise the ROI for each sample disc, the gray level intensity value at each specific XY voxel location is summed with the intensity values corresponding to that same XY voxel location, across all XY slices in the Z stack, to create a new single 2D XY image comprising the cumulative floating-point gray level intensity value at each XY pixel location. The cumulative intensity values are then rescaled so that the gray level intensity values in the cumulative projection image fall within the 8-bit range, while preserving the majority of the dynamic range. The resulting 8-bit, 2D XY cumulative projection image is then referred to as the Basis Weight Index Image for that sample disc.

Average Aperture Equivalent Diameter; Average Aperture Area; Aperture Frequency; Average Fractional Open Area, and Aperture Circularity Aperture Void Regions are identified and defined within the Basis Weight Index Image of each sample disc, via a process of thresholding the gray level intensity values followed by region identification. These processes are used to classify each pixel in a Basis Weight Index Image as either being a component of a specific Aperture Void Region, or as being excluded from all Aperture Void Regions. The threshold intensity value is determined using Otsu's method (Nobuyuki Otsu (1979) "A threshold selection method from gray-level histograms" IEEE Trans. Sys., Man., Cyber. 9 (1): 62-66 doi:10.1109/TSMC.1979.4310076). Otsu's method is a commonly used method to determine an objective and reproducible threshold value for a gray scale image, and achieves this by identifying the threshold value which minimizes the sum of the variances within the two sets of intensity values (i.e., either side of the threshold value). Otsu's method is used to determine the threshold value for the Basis Weight Index Image, and that threshold value is then used to create a binary mask called the Image Mask. From the Basis Weight Index Image all pixel locations whose intensity value is greater than the threshold value are identified and given an intensity value of one in the binary Image Mask. Conversely, all pixel positions in Basis Weight Index Image whose gray level intensity value is less than the threshold value are given an intensity value of zero in the binary Image Mask. Aperture Void Regions are identified and defined as regions of contiguous pixels located within the sample disc, wherein all the pixels corresponding to that contiguous region have an intensity value of zero in the binary Image Mask, and where the region has a contiguous area of at least 100 pixels. Every region which satisfies the above criteria is defined as an Aperture Void Region and is deemed to correspond to the most central part of an aperture. All pixel locations within the sample disc that do not satisfy the criteria for identification as comprising an Aperture Void Region, are given an intensity value of one in the Image Mask. Aperture Void Regions that contact or intersect the circular perimeter of the sample disc are excluded from all calculations and measurements reported, unless doing so would result in zero Aperture Void Regions being measured within the sample disc, in which case the contacted or intersected Aperture Void Regions are to be included in the measurements reported.

The equivalent diameter for any Aperture Void Region is the diameter of a circle whose area is the same as the aperture void region's area. Each Aperture Void Region identified in the Image Mask is measured to determine its Area and Equivalent Diameter. Each of these individual measured values are recorded and reported after conversion from pixels to micrometers using the factor of 12 μm per pixel. For each fibrous structure material being tested, the values recorded for the area and for the equivalent diameter of each Aperture Void Region, are reported individually and are also averaged for each parameter respectively. The Average Aperture Equivalent Diameter and the Average Aperture Area are each calculated and reported across the set of sample discs representing the entire fibrous structure, as well as across the sample discs representing each class of apertures, and zone of apertures, for each individual parameter.

Circularity (also known as Roundness) is a common concept in image analysis that is used to measure the shape of a 2D object and indicates the degree of similarity between that object's shape and the shape of a perfect circle. In this approach, an object with the shape of a perfect circle has a unitless circularity value of one, while circularity values which diverge from the value of one correspond to shapes that diverge from a perfect circle, with higher values indicating increasingly less circular shapes. The circularity value of any given Aperture Void Region is termed Aperture Circularity and is calculated using the equation:

$$\text{Aperture Circularity} = (\text{perimeter})^2 / (4 \times \text{area} \times 3.1416)$$

where, perimeter=the length of the perimeter of the given Aperture Void Region, in units of mm area=the area of the given Aperture Void Region, in units of square mm.

Each Aperture Void Region identified in the Image Mask is measured to determine its Aperture Circularity. Each of these individual measured values are recorded and reported as an individual Aperture Circularity value. Aperture Circularity values are averaged and reported across the set of sample discs representing the entire fibrous structure, as well as across the sample discs representing each class of apertures, and zone of apertures. All of the resulting average values are recorded and reported for each fibrous structure material being tested.

Visually discernable repeat patterns of apertures (i.e., repeated two-dimensional spatial units containing regions both within and outside of Aperture Void Regions) may be present within the entire intact fibrous structure being tested. For fibrous structures wherein visually discernable repeat patterns are absent, the parameters described below which are required to determine the Average Fractional Open Area are calculated directly on the basis of Total Area of the entire intact fibrous structure. The Total Area of the fibrous structure is determined by multiplying the length and width of the entire intact fibrous structure. One skilled in the art will understand that when one or more repeat patterns of apertures is present in the fibrous structure being tested, then any parameters measured on the basis of the largest repeat pattern may be extrapolated to determine the values for those parameters on the basis of the Total Area of the entire intact fibrous structure.

For fibrous structures comprising a repeat pattern, the area of the largest visually discernable repeat pattern is determined and recorded by first measuring and then multiplying together, the pattern repeat distances. The pattern repeat distances are measured in the X and Y directions from the entire intact fibrous structure being tested, and are the two linear distances between locations where the pattern is identical again (i.e., repeats), in adjacent occurrences of the largest repeating pattern. Parameter values that are calculated on the basis of the largest repeat pattern are extrapolated to determine those parameter values for the entire intact fibrous structure. This extrapolation is achieved by multiplying the parameter values calculated for the repeat pattern by the number of times the pattern is repeated across the total fibrous structure. The number of times the pattern is repeated cross the total fibrous structure is determined by dividing the area of the Total Area of the fibrous structure by the area of the largest repeat pattern present.

The Total Number of Apertures is defined as the total number of apertures in all classes and in all zones in the entire intact fibrous structure. The Total Number of Apertures is determined by counting each visually discernable aperture within the entire fibrous structure, or is extrapolated from the count of all visually discernable apertures within the largest repeat pattern including all classes and all zones.

The Aperture Frequency is defined as the total number of all apertures in all classes and in all zones, calculated on the basis of the entire intact fibrous structure and expressed as the number of apertures per sq mm. The Aperture Frequency is calculated according to the following equation:

Aperture Frequency=Total Number of Apertures/
Total Area where the value for the Total Area is calculated for the entire intact fibrous structure, in units of square mm.

The Cumulative Area of Aperture Void Regions in the fibrous structure is determined by multiplying the number of visually discernable apertures counted in the fibrous structure or extrapolated from the count within the largest repeat pattern, by the Average Aperture Area measured. The Average Fractional Open Area is the percentage of the Total Area of the fibrous structure that comprises area within Aperture Void Regions and is calculated according to the following equation:

Average Fractional Open Area (%)=(Cumulative
Area of Aperture Void Regions/Total Area)×100 where the values for the Cumulative Area of Aperture Void Regions and the Total Area are each calculated for the entire intact fibrous structure, in units of square mm.

The Average Fractional Open Area value is reported across the set of sample discs representing the entire fibrous structure. Additionally, where possible the Average Fractional Open Area value is also calculated and reported across the sample discs representing each class of apertures, and zone of apertures. All of the resulting average values are recorded and reported for each fibrous structure material being tested.

Euclidean Distance Map Image

The Basis Weight Index Image is used to generate an Euclidian Distance Map (EDM), wherein the value at each pixel location is a distance value that represents the distance between that pixel and the nearest pixel contained within an Aperture Void Region (as defined above). To measure the distance away from the aperture void region, the Euclidean distance transform is employed to measure the minimum distance from each specific pixel location to the nearest Aperture Void Region pixel. For each sample disc, the binary Image Mask created previously to identify the aperture void regions is now inverted such that pixels in Aperture Void Regions have an intensity value of one and all other pixels have an intensity value of zero, thus creating a mask called the Inverted Image Mask. The Euclidian Distance Map (EDM) for each sample disc is the transform of the Inverted Image Mask, such that the distance value of each pixel location in the EDM is the floating-point Euclidean distance between that respective pixel location in the Inverted Image Mask and the location of its nearest non-zero intensity pixel in the Inverted Image Mask. To exclude data from the outer periphery of the sample disc, the EDM is then adjusted such that all pixel locations are given a distance value of zero if their position is located outside of a circle that is concentric with the perimeter of the sample disc and that has a diameter only 90% of the diameter of the sample disc.

Basis Weight Index Ratio; Basis Weight Index Transition Ratio; Wall Region Slope; and Transition Region Slope The Basis Weight Index Profile is calculated from both the Basis Weight Index Image and the EDM to elucidate the distance dependence of pixel values in the Basis Weight Index Image in proximity to Aperture Void Regions. Each pixel in the EDM has a distance value equal to its distance in pixels from the nearest Aperture Void Region pixel. All pixels in the EDM are allocated to bins according to their distance value, with each bin being defined as an integral number of pixels, i.e. an integer. For each set of pixels allocated within a distance bin, the average value of the Basis Weight Index Image intensity values corresponding to those pixels, is calculated and recorded. These average intensity values per distance bin are calculated across all the sample discs that are replicates, or that form a representative set of samples for a fibrous structure, and for each bin, the resulting value is called the Basis Weight Index Value. The EDM distance value of each distance bin is converted from pixels to micrometers using the scaling factor of 12 µm per pixel. The Basis Weight Index Profile is defined then as the Basis Weight Index Value for all measured distance bin values in micrometers. The Basis Weight Index Profile is readily plotted versus distance from the nearest Aperture Void Region and the resulting curve generally resembles curves such as the Basis Weight Index Profile Curve 60 shown in the Basis Weight Index Profile Plot (lacking a Transition Region) of FIG. 15.

The range of distances that define and comprise the Background Region 62, are all of the distance values corresponding to integer-valued bins in the EDM that are completely contained within the $50^{th}$ to $90^{th}$ percentiles ($100^{th}$ percentile being the greatest distance) of all nonzero distance values in the EDM. The Basis Weight Index Background is a value that is the arithmetic mean of the grey level intensity values found in the Basis Weight Index Image across all pixel positions corresponding to the set of distances comprising the Background Region 62. The Basis Weight Index Ratio is the defined as:

Basis Weight Index Ratio=Basis Weight Index Value
at Aperture Void/Basis Weight Index Background where the Basis Weight Index Value at Aperture Void, as shown by point 64, is the Basis Weight Index Value at the smallest measured distance plotted in the Basis Weight Index Profile Curve 60.

Figure 16:
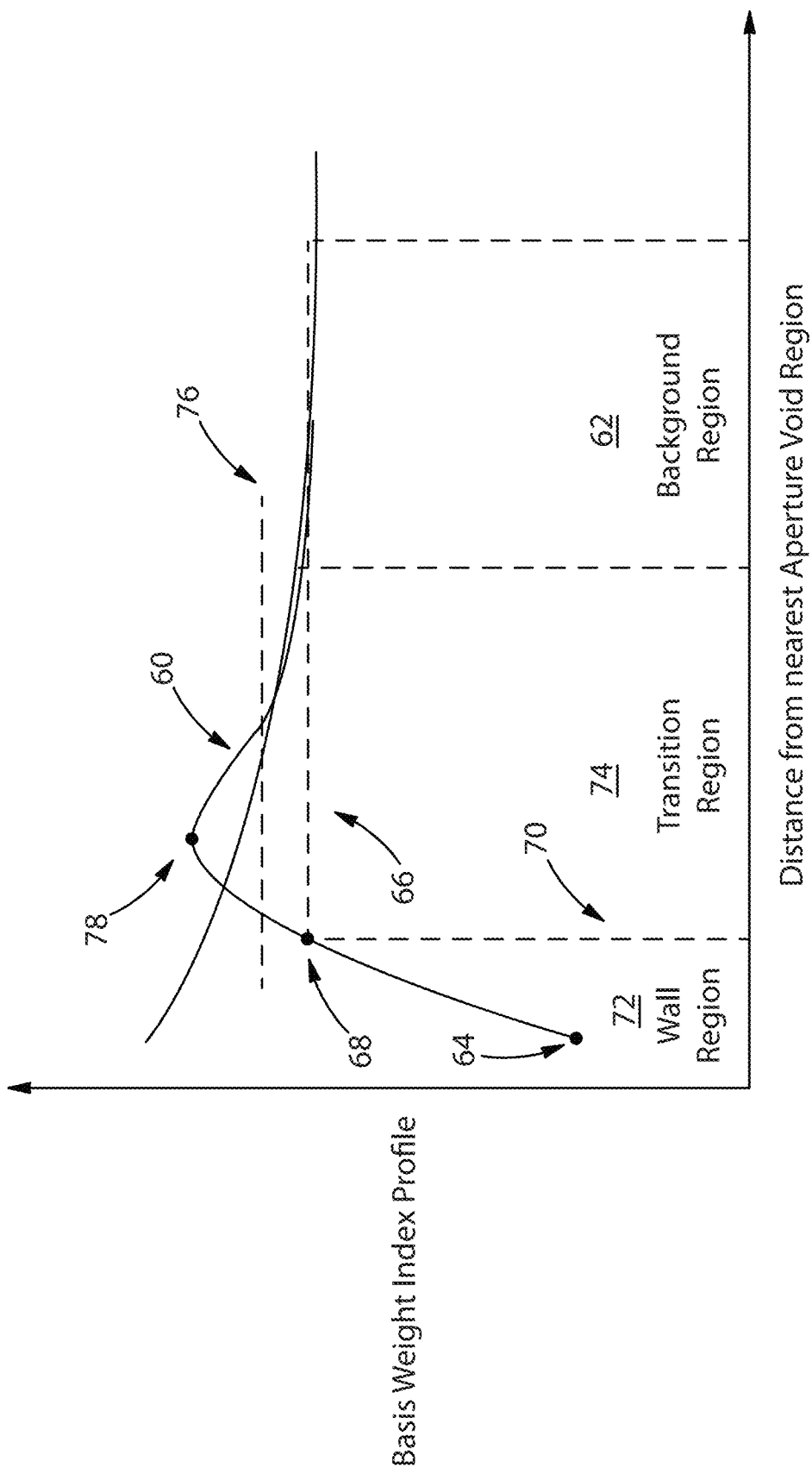
FIG. 16 is an example of a Basis Weight Index Profile Plot Comprising a Transition Region. The x-axis is the Distance from Nearest Aperture Void Region Pixel (in μm). The y-axis is the Basis Weight Index Value (in 8-bit Gray Level Intensity)

On the Basis Weight Index Profile Plots as shown in FIGS. 15 and 16, a horizontal line 66 is drawn at the value of the Basis Weight Index Background. If the line 66, does not cross the Basis Weight Index Profile Curve 60 at a distance that is less than the smallest distance in Background Region 62, then no further regions are defined, which is the case for the Basis Weight Index Profile Plot of FIG. 15. In this case, the Basis Weight Index Transition Ratio is defined as a value of one, the Wall Region Slope is defined as a value of zero, and the Transition Region Slope is defined as a value of zero.

On the Basis Weight Index Profile Plot (including a Transition Region) as shown in FIG. 16, if the line 66 crosses the Basis Weight Index Profile Curve 60 at a distance that is less than the smallest distance in the Background Region 62, then the intersection of the line 66 and the Basis Weight Index Profile Curve 60 is termed the Crossing Point 68. The data point having the lowest Basis Weight Index Value and also having a distance greater than the distance of Crossing Point 68 is identified, and the distance corresponding to this identified point is called the Wall Transition Boundary, as shown by line 70. The range of distances with distances less than or equal to the Wall Transition Boundary 70 is called the Wall Region 72, and the range of distances having distances greater than the Wall Transition Boundary 70 but less than the Background Region 62 is called the Transition Region 74. The average of the Basis Weight Index Values for all pixel positions corresponding to distances within the Transition Region 74, is called the Basis Weight Index Transition Average, as shown by line 76. The Basis Weight Index Transition Ratio is defined as:

Basis Weight Index Transition Ratio=Basis Weight
Index Transition Average/Basis Weight Index
Background.

The maximum Basis Weight Index Value occurring within the Transition Region is called the Basis Weight Index Profile Peak, as shown by point 78. If more than one data point possesses the maximum value, the Basis Weight Index Profile Peak is the maximum occurring at the smallest distance. The distance corresponding to the Basis Weight Index Profile Peak is called the Basis Weight Index Profile Peak Distance. The Basis Weight Peak Ratio is defined as:

Basis Weight Index Peak Ratio=Basis Weight Index Profile Peak/Basis Weight Index Background.

Further, the approximate slope of the Basis Weight Index Profile Curve 60 within the Wall Region 72 is called the Wall Region Slope and is defined as:

Wall Region Slope=(1−Basis Weight Index Ratio)/Wall Transition Boundary.

where the Wall Transition Boundary is in units of μm.

Still further, the approximate slope of the Basis Weight Index Profile Curve 60 at the start of the Transition Region is called the Transition Region Slope and is defined as:

Transition Region Slope=(Basis Weight Peak Ratio−1)/(Basis Weight Index Profile Peak Distance−Wall Transition Boundary).

where the Basis Weight Index Profile Peak Distance and Wall Transition Boundary are both in units of μm.

The Basis Weight Index Ratio, Basis Weight Index Transition Ratio, Wall Region Slope, and Transition Region Slope values are calculated, averaged and reported across the set of sample discs representing the entire fibrous structure, as well as across the sample discs representing each class of apertures, and each zone of apertures, for each individual parameter.

Fiber Orientation Index Image

The extent to which the orientation of the sample fibers are deflected from the XY plane of the sample disc and toward the Z direction perpendicular to the sample disc plane, is quantified at each XY pixel location in a sample disc. This quantification is achieved by measuring the approximate gradients of all fiber surfaces in the sample disc and then comparing the relative horizontal and vertical gradient magnitudes. When a fiber is deflected out of the XY plane of the sample disc, more of that individual fiber's surface is oriented vertically and this gives rise to a larger vertical gradient. The ratio of summed vertical and horizontal gradient magnitudes at each XY position is then interpreted as the tangent of some angle, and this angle is calculated to generate the Fiber Orientation Index Image.

The 2D Sobel gradient operator described in the book "Pattern Classification and Scene Analysis", (Duda, Hart Wiley & Sons, 1973), is an image analysis tool commonly available image analysis software programs and is widely used to calculate the orientation, magnitude, and location of edges (boundaries of different intensities) in images. When the Sobel operator is applied to an image, two 3×3 matrices are convolved with the entire image to give rise to two images of the same size as the original. One matrix (and resulting image) approximates the size and location of edges in the vertical direction and the other approximates size and location of edges in the horizontal direction.

To calculate the Fiber Orientation Index Image, 2D Sobel gradient operators are used to create four 3D gradient datasets. In each case, the 3D dataset is decomposed into 2D image planes, and a 2D Sobel gradient operator is applied along one of the two principal axes of the image plane to generate a gradient component image. These gradient component images are then restacked to create a 3D gradient dataset along that same principal axis.

For all XZ images planes of a sample disc, a 2D Sobel operator is used to produce a gradient component image with gradient in the Z direction. These images are then restacked to create a 3D dataset called XZ_vertical.

For all XZ image planes of a sample disc, a 2D Sobel operator is used to produce a gradient component image with gradient in the X direction. These images are then restacked to create a 3D dataset called XZ_horizontal.

For all YZ image planes of a sample disc, a 2D Sobel operator is used to produce a gradient component image with gradient in the Z direction. These images are then restacked to create a 3D dataset called YZ_vertical.

For all YZ image planes of a sample disc, a 2D Sobel operator is used to produce a gradient component image with gradient in the Y direction. These images are then restacked to create a 3D dataset called YZ_horizontal.

Three-dimensional data set Vertical Gradient Data is then created by calculating the square root of the sum of the squares (called the Norm) of corresponding voxels for each pair of corresponding voxels in XZ_vertical and YZ_vertical, Vertical Gradient Data is then summed along the Z dimension to create 2D image Vertical Gradient Projection. Three-dimensional data set Horizontal Gradient Data is created by calculating the Norm of corresponding voxels for each pair of corresponding voxels in XZ_horizontal and YZ_horizontal. Horizontal Gradient Data is then summed along the Z dimension to create 2D image Horizontal Gradient Projection. Each pixel value in the 2D Fiber Orientation Index Image is then defined according to the following equation, for all corresponding pairs of voxels ($vgp_{ij}$) in the Vertical Gradient Projection and ($hgp_{ij}$) in the Horizontal Gradient Projection:

FOI($i,j$)=(180/3.14159)×abs (arctan ($vgp_{ij}$/$hgp_{ij}$))

where,

FOI(i,j)=pixel in position i,j in the Fiber Orientation Index Image, abs denotes the Absolute Value Function, arctan denotes the inverse function of the Tangent Function, $vgp_{ij}$=pixel in position i,j of the Vertical Gradient Projection, $hgp_{ij}$=pixel in position i,j of the Horizontal Gradient Projection.

Fiber Orientation Index Ratio

Figure 17:
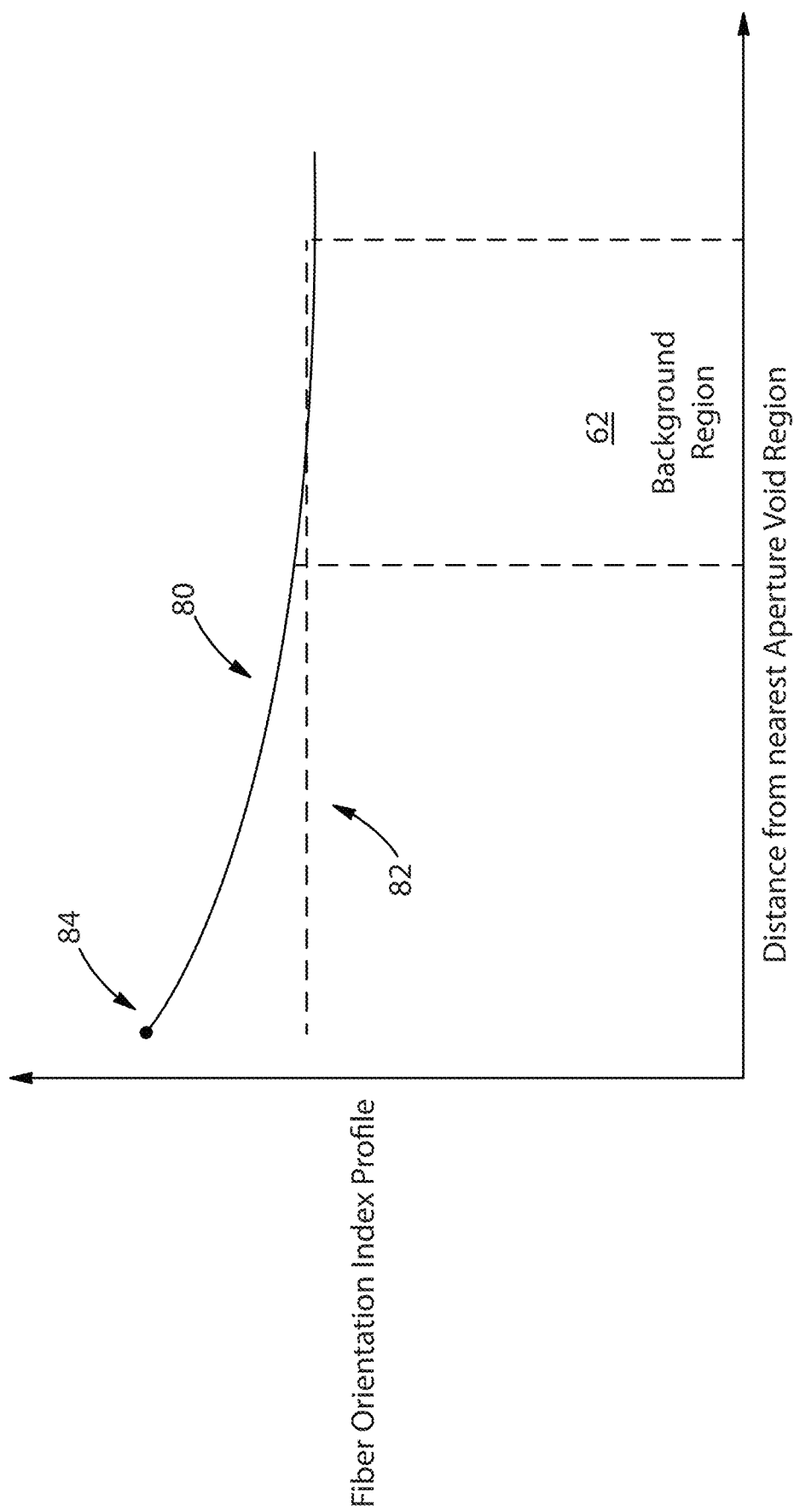
FIG. 17 is an example of a Fiber Orientation Index Profile Plot. The x-axis is the Distance from Nearest Aperture Void Region Pixel (in μm). The y-axis is the Fiber Orientation Index Value (in 8-bit Gray Level Intensity).

The Fiber Orientation Index Profile is calculated from both the Fiber Orientation Index Image and the EDM to elucidate the distance dependence of fiber deflection in proximity to Aperture Void Regions. Each pixel in the EDM has a distance value equal to its distance in pixels from the nearest Aperture Void Region pixel. All pixels in the EDM are allocated to bins according to their distance value, with each bin being defined as an integral number of pixels, i.e. an integer. For each set of pixels allocated within a distance bin, the average value of the Fiber Orientation Index Image intensity values corresponding to those pixels, is calculated and recorded. These average intensity values per distance bin are calculated across all the sample discs that are replicates, or that form a representative set of samples for a fibrous structure, and for each bin, the resulting value is called the Fiber Orientation Index Value. The EDM distance value of each distance bin is converted from pixels to micrometers using the scaling factor of 12 μm per pixel. The Fiber Orientation Index Profile is defined then as the Fiber Orientation Index Value for all measured distance bin values in micrometers. The Fiber Orientation Index Profile is readily plotted versus distance from the nearest Aperture Void Region and the resulting curve generally resemble curves such as the Fiber Orientation Index Profile Curve 80 shown in the Fiber Orientation Index Profile Plot of FIG. 17.

The range of distances that define and comprise the Background Region 62, are all of the distance values corresponding to integer-valued bins in the EDM that are completely contained within the $50^{th}$ to $90^{th}$ percentiles ($100^{th}$ percentile being the greatest distance) of all nonzero distance values in the EDM. The Background Region 62 as defined above, is also used with the Fiber Orientation Index Profile. The Fiber Orientation Index Background, as shown by line 82, is a value that is the arithmetic mean of the plotted Fiber Orientation Index grey level intensity values found in the Fiber Orientation Index Image across all pixel positions corresponding to the set of distances comprising the Background Region 62. The Fiber Orientation Index Ratio is the defined as:

Fiber Orientation Index Ratio=Fiber Orientation Index at Aperture Void/Fiber Orientation Index Background where, the Fiber Orientation Index at Aperture Void is the value of the Fiber Orientation Index Profile at the smallest measured distance, as shown by point 84.

The Fiber Orientation Index Ratio values are calculated, then averaged and reported across the set of sample discs representing the entire fibrous structure, as well as across the sample discs representing each class of apertures, and each zone of apertures.

Optical Aperture Characterization Test Method

Measurement of the Aperture Optical Circular Diameter (AOCD), the Aperture Optical Circular Area (AOCA), and the Aperture Optical Circular Percentage (AOC %) is achieved using an optical magnification device. The optical magnification device is capable of between 5× to 20× magnification and is combined with a measuring scale, wherein the scale divisions include intervals of 0.1 mm. One such suitable optical magnification device is the 10× Bausch & Lomb Hastings Triplet Measuring Magnifier Loupe (Bausch & Lomb Inc., Bridgewater, N.J., USA), outfitted with a measuring scale reticle. The measuring scale reticle in the loupe is located at the focal plane of the lens. The loupe is placed in direct contact with the sample, thus allowing for precise measurement of aperture dimensions without parallax error or distortion. The transparent body of the loupe allows incident light to illuminate the sample. The selection of magnification is determined by the size of the aperture openings to be measured, since smaller aperture openings may require higher magnification than larger aperture openings.

The AOCD is an average length value expressed in mm. The AOCA is an average area value expressed in square mm. The AOC % is a cumulative area value expressed as a percentage of the area of the planar surface which was inspected and in which the measured apertures were located.

For the purposes of this method, a representative sample of the fibrous structure to be tested is laid out flat against a contrasting background and is inspected with sufficient oblique incident light and sufficient magnification to enable clear observation and measurement through the magnifying device, of the openings of individual apertures. The openings of each aperture are measured at the upper most surface plane of both planar surfaces of the fibrous structure. This upper most surface plane is typically the location of the shoulder of the aperture opening, where the surface begins to dip downwards before forming the walls of the aperture. In some embodiments, the surrounding surface and shoulder of an aperture opening may occur at a plane which is elevated above (outward from) the generally planar surface of the fibrous structure, forming a volcano-like structure rising above the planar surface. In such cases, the aperture opening is measured at the outermost plane described by the perimeter of the aperture. Measurements are taken of the diameter of each individual aperture opening along two axes of that aperture. To conduct the two diameter measurements, a first diameter measurement is made along the major axis, which comprises the longest diameter length of the aperture opening. A second diameter measurement is then made along the axis which is perpendicular to the previously measured major axis.

For each aperture opening, the two perpendicular diameter measurements are averaged to yield the AOCD value of that aperture opening in that planar surface. For each aperture opening, the AOCD value in that planar surface is used to calculate the AOCA for that aperture in that planar surface, via the following equation for the area of a circle having the AOCD value as its diameter:

$$AOCA=\pi*r^2$$

where:
$\pi=3.1416$
* Denotes the multiplication operator, and
r=half the AOCD value.

For fibrous structures comprising a repeat pattern of apertures, the entire repeat pattern is inspected and all apertures with the inspected entire repeat pattern are measured as specified above. Sufficient replicates of the entire repeat pattern are inspected until all apertures within at least 10% of the total area of the entire fibrous structure have been measured. For fibrous structures which lack a repeat pattern of apertures, at least 10% of the total area of the entire fibrous structure is inspected and all apertures within the inspected area are measured. The area(s) for inspection are selected such that the set of apertures measured is representative of the variety of apertures present and representative of their relative frequency in the structure (i.e., different aperture varieties are number-weighted, not area-weighted). Additionally, the area of the planar surface which was inspected and in which the measured apertures were located is determined, and may be calculated from measurements obtained using a ruler.

All values calculated for the AOCD and AOCA parameters are averaged within each parameter and within each planar surface, to yield the mean value for each parameter on each planar surface, respectively. Within each of these two parameters, of the mean values calculated for each of the two planar surfaces, it is the larger of the two values that is reported for each parameter for that fibrous structure material.

To determine the AOC % value, all the AOCA values measured for each planar surface are summed together to determine the cumulative area of the measured aperture openings on that planar surface. This cumulative area value is divided by the area of that planar surface which was inspected and in which the measured apertures were located. The result of that division is multiplied by 100 to yield the AOC % value for that planar surface. Of the AOC % values calculated for each of the two planar surfaces, it is the larger of the two values that is reported as the AOC % value for that fibrous structure material.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

Every document cited herein, including any cross referenced or related patent or application, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A polar solvent-soluble fibrous structure comprising a plurality of polar solvent-soluble fibrous elements wherein at least one of the polar solvent-soluble fibrous elements comprises one or more fibrous element-forming materials selected from the group consisting of pullulan, hydroxypropylmethyl cellulose, hydroxyethyl cellulose, hydroxypropyl cellulose, hydroxymethyl cellulose, carboxymethyl cellulose, polyvinyl alcohol, starch, starch derivatives, polyethylene glycol, and mixtures thereof and one or more active agents present within the polar solvent-soluble fibrous element that are releasable from the polar solvent-soluble fibrous element when the polar solvent-soluble fibrous element solubilizes, the polar solvent-soluble fibrous structure further comprises a plurality of apertures wherein the apertures are arranged in a pattern within the polar solvent-soluble fibrous structure such that the polar solvent-soluble fibrous structure comprises the following structural characteristics:
   a. a Fiber Orientation Index Ratio of greater than 1 as measured according to the Aperture Parameter Test Method;
   b. an Average Aperture Equivalent Diameter of greater than 0.15 mm as measured according to the Aperture Parameter Test Method; and
   c. an Average Fractional Open Area of from about 0.005% to about 80% as measured according to the Aperture Parameter Test Method.

2. The polar solvent-soluble fibrous structure according to claim 1, wherein the polar solvent-soluble fibrous structure further exhibits a Basis Weight Index Transition Ratio of greater than 1 as measured according to the Aperture Parameter Test Method.

3. The polar solvent-soluble fibrous structure according to claim 1, wherein the polar solvent-soluble fibrous structure exhibits a Fiber Orientation Index Ratio of greater than 1.03 as measured according to the Aperture Parameter Test Method.

4. The polar solvent-soluble fibrous structure according to claim 1, wherein the polar solvent-soluble fibrous structure exhibits an Average Aperture Equivalent Diameter of greater than 0.3 mm as measured according to the Aperture Parameter Test Method.

5. The polar solvent-soluble fibrous structure according to claim 1, wherein the polar solvent-soluble fibrous structure further exhibits an Average Fractional Open Area of greater than about 0.01% to about 80% as measured according to the Aperture Parameter Test Method.

6. The polar solvent-soluble fibrous structure according to claim 1, wherein the polar solvent-soluble fibrous structure further exhibits an Average Aperture Area of greater than 0.05 mm$^2$ as measured according to the Aperture Parameter Test Method.

7. The polar solvent-soluble fibrous structure according to claim 1, wherein the polar solvent-soluble fibrous structure further exhibits a Wall Region Slope of greater than 0.01 to less than 0.08 as measured according to the Aperture Parameter Test Method.

8. The polar solvent-soluble fibrous structure according to claim 1, wherein the polar solvent-soluble fibrous structure further exhibits a Transition Region Slope of greater than 0.0003 to less than 0.1 as measured according to the Aperture Parameter Test Method.

9. The polar solvent-soluble fibrous structure according to claim 1, wherein the polar solvent-soluble fibrous structure comprises two or more classes of apertures such that the polar solvent-soluble fibrous structure exhibits two or more different Average Aperture Equivalent Diameters as measured according to the Aperture Parameter Test Method.

10. The polar solvent-soluble fibrous structure according to claim 1, wherein two or more of the apertures are spaced apart from one another at a distance of from about 0.2 mm to about 100 mm.

11. The polar solvent-soluble fibrous structure according to claim 1, wherein the at least one of the polar solvent-soluble fibrous elements further comprises a hydroxyl polymer selected from the group consisting of sodium alginate, xanthan gum, tragacanth gum, guar gum, acacia gum, Arabic gum, polyacrylic acid, dextrin, pectin, chitin, collagen, gelatin, zein, gluten, soy protein, casein, hemicellulose, hemicellulose derivatives, proteins, chitosan, chitosan derivatives, tetramethylene ether glycol, and mixtures thereof.

12. The polar solvent-soluble fibrous structure according to claim 1, wherein the active agent is selected from the group consisting of fabric care active agents, dishwashing active agents, hard surface active agents, hair care active agent, floor care active agents, skin care active agents, oral care active agents, medicinal active agents, carpet care active agents, surface care active agents, air care active agents, and mixtures thereof.

13. The polar solvent-soluble fibrous structure according to claim 1, wherein the active agent is present in the at least one of the polar solvent-soluble fibrous elements at a level of at least 20% by weight of the polar solvent-soluble fibrous element.

14. The polar solvent-soluble fibrous structure according to claim 1, wherein the polar solvent-soluble fibrous structure exhibits a basis weight of from about 1 g/m$^2$ to about 10,000 g/m$^2$.

15. The polar solvent-soluble fibrous structure according to claim 1, wherein the at least one of the polar solvent-soluble fibrous elements exhibits an average diameter of less than 50 µm as measured according to the Diameter Test Method.

16. The polar solvent-soluble fibrous structure according to claim 1, wherein the polar solvent-soluble fibrous structure exhibits an average disintegration time of about 60 seconds or less as measured according to the Dissolution Test Method.

17. The polar solvent-soluble fibrous structure according to claim 1, wherein the polar solvent-soluble fibrous structure exhibits an average dissolution time of about 600 seconds or less as measured according to the Dissolution Test Method.

18. The polar solvent-soluble fibrous structure according to claim 1, wherein the polar solvent-soluble fibrous structure exhibits an average disintegration time per gsm of about 1.0 seconds/gsm or less as measured according to the Dissolution Test Method.

19. The polar solvent-soluble fibrous structure according to claim 1, wherein the polar solvent-soluble fibrous structure exhibits an average dissolution time per gsm of about 10 seconds/gsm or less as measured according to the Dissolution Test Method.

20. The polar solvent-soluble fibrous structure according to claim 1, wherein the polar solvent-soluble fibrous structure exhibits a Geometric Mean (GM) Tensile Strength of greater than 200 g/cm as measured according to the Tensile Test Method.

21. The polar solvent-soluble fibrous structure according to claim 1, wherein the polar solvent-soluble fibrous structure exhibits a GM Peak Elongation of less than 1000% as measured according to the Tensile Test Method.

22. The polar solvent-soluble fibrous structure according to claim 1, wherein the polar solvent-soluble fibrous structure exhibits a GM Tangent Modulus of less than 5000 g/cm as measured according to the Tensile Test Method.

23. The polar solvent-soluble fibrous structure according to claim 1, wherein the polar solvent-soluble fibrous structure exhibits a GM Secant Modulus of less than 5000 g/cm as measured according to the Tensile Test Method.

24. The polar solvent-soluble fibrous structure according to claim 1, wherein the polar solvent-soluble fibrous structure exhibits a water content of from about 0% to about 20% as measured according to the Water Content Test Method.

25. A multi-ply polar solvent-soluble fibrous structure comprising a least one polar solvent-soluble fibrous structure according to claim 1.

26. The polar solvent-soluble fibrous structure according to claim 2, wherein the polar solvent-soluble fibrous structure exhibits a Basis Weight Index Transition Ratio of greater than 1.025 as measured according to the Aperture Parameter Test Method.

* * * * *